United States Patent [19]

Breu et al.

[11] Patent Number: 5,541,186
[45] Date of Patent: Jul. 30, 1996

[54] SULFONYLAMINOPYRIMIDINES

[75] Inventors: Volker Breu, Schliengen, Germany;
Kaspar Burri, Binningen, Switzerland;
Jean-Marie Cassal, Mulhouse, France;
Martine Clozel, Saint-Louis, France;
Georges Hirth, Huningue, France;
Bernd-Michael Löffler, Oberrimsingen, Germany; Marcel Müller, Frenkendorf, Switzerland; Werner Neidhart, Bartenheim, France; Henri Ramuz, Birsfelden, Switzerland

[73] Assignee: Hoffmann-La Roche Inc., Nutley, N.J.

[21] Appl. No.: 266,072

[22] Filed: Jun. 27, 1994

[30] Foreign Application Priority Data

Jun. 28, 1993 [CH] Switzerland ............... 1924/93
May 20, 1994 [CH] Switzerland ............... 1575/94

[51] Int. Cl.[6] ............ A61K 31/505; C07D 239/42; C07D 239/49; C07D 239/50
[52] U.S. Cl. ............ 514/256; 514/269; 514/272; 514/273; 514/274; 514/275; 514/212; 514/227.8; 514/232.2; 514/235.8; 514/236.5; 514/252; 514/262; 514/265; 514/266; 540/601; 544/295; 544/296; 544/58.2; 544/58.6; 544/60; 544/82; 544/122; 544/123
[58] Field of Search ............ 514/256, 269, 514/272, 273, 274, 275, 212, 235.8, 262; 544/309, 319, 327, 295, 58.6, 122, 277, 323; 540/601

[56] References Cited

U.S. PATENT DOCUMENTS 5,270,313  12/1993  Burri et al. ............... 514/252
5,292,740  3/1994   Burri et al. .

FOREIGN PATENT DOCUMENTS 0601386  11/1993  European Pat. Off. .

Primary Examiner—John M. Ford
Attorney, Agent, or Firm—George M. Gould; George W. Johnston; Robert A. Silverman

[57] ABSTRACT

A compound of the formula

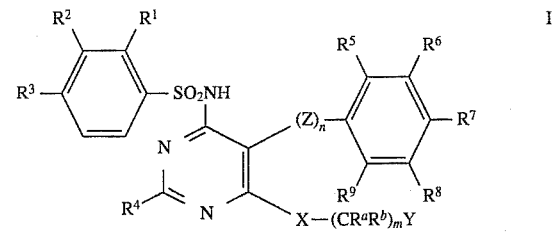

wherein $R^1$ to R, $R^a$, $R^b$X, Y, Z, m and n have the significance given in the description, can be used as medicaments, especially for the treatment and prophylaxix of conditions which are associated with endothelin activities.

23 Claims, No Drawings

SULFONYLAMINOPYRIMIDINES

The invention relates to sulfonylaminopyrimidines and their use as medicaments. In particular, the invention is concerned with sulfonyl-aminopyrimidines of the formula

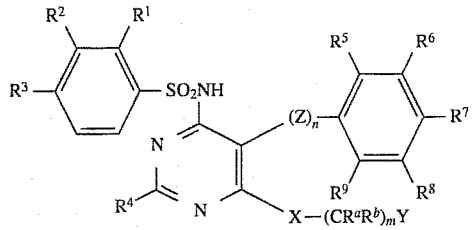

wherein
- $R^1$–$R^3$ each independently signify hydrogen, lower-alkyl, lower-alkoxy, lower-alkylthio, lower-alkenyl, halogen, trifluoro-methyl, hydroxy-lower-alkoxy, halo-lower-alkoxy, cyclo-lower-alkyl, hydroxy-lower-alkanoylamino-lower-alkoxy, alkanoylamino-lower-alkyl, carboxy-lower-alkoxy, carboxy-lower-alkyl, lower-alkoxycarbonyl-lower-alkyl, lower-alkoxycarbonyl-lower-alkoxy, alkanoyloxy-lower-alkoxy, alkanoyloxy-lower-alkyl, alkoxycarbonyl, carboxy, amino, mono- or di-(lower-alkyl)amino or a residue $(R^c,R^d)N$-$C(O)(CH_2)_{0-4}O$- or $(R^c, R^d)N$-$C(O)(CH_2)_{0-4}$-;
- $R^2$ and $R^3$ together signify butadienyl, methylenedioxy, ethylenedioxy or isopropylidenedioxy;
- $R^4$ signifies hydrogen, lower-alkyl, cyclo-lower-alkyl, trifluoro-methyl, lower-alkoxy, lower-alkinyloxy, lower-alkylthio, lower-alkylthio-lower-alkyl, lower-alkylthio-lower-alkoxy, hydroxy-lower-alkyl, hydroxy-lower-alkoxy, dihydroxy-lower-alkoxy, lower-alkoxy-lower-alkyl, hydroxy-lower-alkoxy-lower-alkyl, lower-alkoxy-lower-alkoxy, di(lower-alkoxy)-alkoxy, hydroxy-lower-alkoxy-lower-alkoxy, lower-alkylsulphinyl, lower-alkylsulphinyl-lower-alkoxy, lower-alkylsulphonyl, 2-methoxy-3-hydroxypropoxy, 2-hydroxy-3-phenylpropyl, amino-lower-alkyl, lower-alkylamino-lower-alkyl, di-lower-alkylamino-lower-alkyl, amino, lower-alkylamino, di-lower-alkylamino, arylamino, aryl, arylthio, aryloxy, aryl-lower-alkyl, aryl-lower-alkoxy-lower-alkyl, aryl-lower-alkyl-lower-alkoxy, heterocyclyl, heterocyclyl-lower-alkyl or heterocyclyl-lower-alkoxy;
- $R^5$ to $R^9$ each independently signify hydrogen, halogen, trifluoromethyl, lower-alkyl, lower-alkoxy, lower-alkylthio, lower-alkylsulphinyl or lower-alkylsulphonyl;
- $R^6$ and $R^5$ or $R^7$ together signify butadienyl, methylenedioxy, ethylenedioxy or isopropylidenedioxy;
- $R^a$ and $R^b$ each independently signify hydrogen, lower-alkyl, lower-alkoxy or lower-alkylthio;
- $R^c$ and $R^d$ each independently signify hydrogen, lower-alkyl or aryl; or $R^c$ and $R^d$ together with the N atom to which they are attached signify a 5–7-membered heterocyclic residue;
- Y signifies a residue -OC(O)$NR^{10}R^{11}$, -NHC(O)$NR^{10}R^{11}$, -OC(O)$OR^{10}$ or -NHC(O)$OR^{10}$;
- $R^{10}$ signifies lower-alkyl, cyclo-lower-alkyl, hydroxy-lower-alkyl, carboxy-lower-alkyl, lower-alkoxycarbonyl-lower-alkyl, lower-alkanoyloxy-lower-alkyl, aryl, aryl-lower-alkyl, arylcarbamoyl-lower-alkyl, heterocyclyl, heterocyclyl-lower-alkyl or a residue $(R^c,R^d)N$-$C(O)(CH_2)_{1-4}$-; and
- $R^{11}$ signifies hydrogen or a residue $R^{10}$; or
- $R^{10}$ and $R^{11}$ together with the N atom to which they are attached signify a 5–7 membered heterocyclic residue;
- Z signifies -O-, -S- or -CH$_2$-;
- X signifies -O-, -S- or -NH-;
- n signifies 0 or 1; and
- m signifies 1, 2 or 3, and pharmaceutically usable salts thereof.

The term "lower" used here denotes groups with 1–7 C atoms, preferably 1–4 C atoms. Alkyl, alkoxy and alkylthio groups as well as alkyl groups as components of alkanoyl groups can be straight-chain or branched. Methyl, ethyl, propyl, isopropyl, butyl, sec. and tert.butyl are examples of such alkyl groups. Halogen denotes fluorine, chlorine, bromine and iodine, with chlorine being preferred. Cycloalkyl residues contain 3 to 8 C atoms, such as cyclopropyl, cyclobutyl, cyclopentyl or cyclohexyl. Examples of aryl residues are phenyl and substituted phenyl residues, with especially halogen, lower-alkyl, lower-alkoxy, lower-alkylenedioxy, carboxyl and trifluoromethyl coming into consideration as substituents. Examples of heterocyclyl residues are mono- or bicyclic 5-, 6- and 7-membered heterocyclic residues which have oxygen, nitrogen or sulphur as the hetero atom, such as 2- and 3-furyl, 2-, 4- and 5-pyrimidinyl, 2-, 3- and 4-pyridyl and pyridyl N-oxide, 1,2- and 1,4-diazinyl, morpholino, thiomorpholino, thiomorpholino-4,4-dioxide, 2,2-dimethyl-1,3-dioxolanyl, 2- and 3-thienyl, isoxazolyl, oxazolyl, thiazolyl, imidazolyl, pyrrolyl, pyrrolidinyl, piperidinyl, azepanyl, benzofuranyl, benzothienyl, indolyl, purinyl, quinolyl, isoquinolyl and quinazolyl, which residues can be substituted, e.g. by 1 or 2 lower-alkyl or lower-alkoxy groups or halogen atoms.

A preferred group of compounds of formula I comprises those in which n=1 and of these there are preferred those in which Z=-O-. X is preferably -O-. Y is preferably -OC(O)$NR^{10}R^{11}$. Preferably, m is 2. Preferred residues $R^1$-$R^3$ are hydrogen, lower-alkyl, cyclo-lower-alkyl, lower-alkylthio, lower-alkoxy, lower-alkenyl, alkanoyloxy-lower-alkoxy, hydroxy-lower-alkoxy, lower-alkoxy-carbonyl-lower-alkoxy, halo-lower-alkoxy, di-(lower-alkyl)amino or the residues $(R^c,R^d)N$-$C(O)(CH_2)_{0-4}O$- and $(R^c,R^d)N$-$C(O)(CH_2)_{0-4}$- in which $R^c$ and $R^d$ together form a piperidino or morpholino residue. Furthermore, those compounds in which $R^2$ and $R^3$ together represent methylenedioxy are preferred.

Hydrogen, lower-alkyl, lower-alkylthio, phenyl-lower-alkyl-lower-alkyl, cyclo-lower-alkyl, lower-alkoxy-lower-alkyl; phenyl, lower-alkoxyphenyl, thienyl, pyrimidinyl and morpholino are preferred residues $R^4$.

Hydrogen, halogen and lower-alkoxy are preferred residues $R^5$-$R^9$. Compounds with $R^5$= halogen, $R^6$, $R^7$ and $R^9$= hydrogen and $R^8$= lower-alkoxy are especially preferred. Preferred residues $R^{10}$ are lower-alkyl, hydroxy-lower-alkyl, carboxy-lower-alkyl, lower-alkoxycarbonyl-lower-alkyl, lower-alkanoyloxy-lower-alkyl, phenyl, which can be substituted by halogen, hydroxy, lower-alkyl, lower-alkoxy, lower-alkoxycarbonyl, lower-alkanoyloxy, trifluoromethyl or methylenedioxy; phenyl-carbamoyl-lower-alkyl, cyclohexyl; heterocyclic residues such as pyridyl, pyridyl N-oxide, N-lower-alkyl-pyridyl, thienyl, furyl, N-lower-alkyl-pyrrolyl, 1,4-diazinyl; picolyl, picolyl N-oxide, furylmethyl, quinolyl, morpholino-carbonyl, morpholino-carbonyl-lower-alkyl, and pyrrolidino-carbonyl-lower-alkyl. $R^{11}$ is preferably hydrogen.

Examples of compounds of formula I wherein Y=-OC(O)$NR^{10}R^{11}$, $R^{10}$ is a pyridyl residue and $R^{11}$ is hydrogen are:

pyridin-2-ylcarbamic acid 2-[6-(1,3-benzodioxol-5-yl-sulfonylamino)-5-(2-chloro-5-methoxy-phenoxy)-pyrimidin-4-yloxy]-ethyl ester, pyridin-2-ylcarbamic acid 2-[6-(4-tert-butyl-phenyl -sulfonylamino)-5-(2-chloro-5-methoxy-phenoxy)-2-methoxymethyl -pyrimidin-4-yloxy]-ethyl ester, pyridin-2-ylcarbamic acid 2-[6-(1,3-benzodioxol-5 -ylsulfonylamino)-5-(2-chloro-5-methoxy-phenoxy)-2-methoxymethyl -pyrimidin-4-yloxy]-ethyl ester, pyridin-2-ylcarbamic acid 2-[6-(1,3-benzodioxol-5 -ylsulfonylamino)-5-(2-chloro-5 -methoxy-phenoxy)-2-(2-methoxyethyl) -pyrimidin-4-yloxy]-ethyl ester, pyridin-2-ylcarbamic acid 2-[6-(1,3-benzodioxol-5 -ylsulfonylamino)-5-(2-chloro-5-methoxy-phenoxy)-2-methylsulfanyl -pyrimidin-4-yloxy]-ethyl ester, pyridin-2-ylcarbamic acid 2-[6-(1,3-benzodioxol-5 -ylsulfonylamino)-5-(2-methoxy-phenoxy)-2-(4-methoxy-phenyl) -pyrimidin-4-yloxy]-ethyl ester, pyridin-2-ylcarbamic acid 2-[6-(1,3-benzodioxol-5 -ylsulfonylamino)-5-(2-methoxy-phenoxy)-2-phenyl-pyrimidin-4 -yloxy]-ethyl ester, pyridin-2-ylcarbamic acid 2-[6-(1,3-benzodioxol-5 -ylsulfonylamino )-5-(3,5-dimethoxy-phenoxy)-pyrimidin-4-yloxy] -ethylester, pyridin-2-ylcarbamic acid 2-[6-(4-tert-butylphenyl -sulfonylamino)-5-(2-chloro-5-methoxy-phenoxy)-pyrimidin-4 -yloxy]ethyl ester, 1-oxy-pyridin-2-ylcarbamic acid 2-[6-(4-tert-butyl-phenyl -sulfonylamino)-5-(2-chloro-5-methoxy-phenoxy)-pyrimidin-4-yloxy] -ethyl ester, pyridin-2-ylcarbamic acid 2-[6-(4-tert-butyl-phenylsulfonyl -amino)-5-(3-methoxy-phenoxy)-pyrimidin-4-yloxy]-ethyl ester, pyridin-2-ylcarbamic acid 2-[6-(4-tert-butyl -phenylsulfonylamino)-2-isopropyl-5-(2-methoxy-phenoxy)-pyrimidin -4-yloxy]-ethyl ester, pyridin-2-ylcarbamic acid 2-[6-(4-tert-butyl -phenylsulfonylamino)-5-(2-methoxy-phenoxy)-2-propyl-pyrimidin-4 -yloxy]-ethyl ester, pyridin-2-ylcarbamic acid 2-[2-tert-butyl-6-(4-tert-butyl -phenylsulfonylamino)-5-(2-methoxy-phenoxy)-pyrimidin-4-yloxy]-ethyl ester, pyridin-2-ylcarbamic acid 2-[6-(4-tert-butyl -phenylsulfonylamino)-2-cyclopropyl-5-(2-methoxy-phenoxy) -pyrimidin-4-yloxy]-ethyl ester, pyridin-2-ylcarbamic acid 2-[6-(4-tert-butyl-phenylsulfonyl -amino)-5-(2-methoxy-phenoxy)-2-thiophen-2-yl-pyrimidin-4-yloxy]-ethyl ester, pyridin-2-ylcarbamic acid 2-[6-(4-tert-butyl -phenylsulfonylamino)-5-(2-methoxy-phenoxy)-2-methyl-pyrimidin-4 -yloxy]-ethyl ester, pyridin-2-ylcarbamic acid-2-[6-(4-tert-butyl -phenylsulfonylamino)-5-(2-methoxy-phenoxy)-2,2'-bipyrimidin-4 -yloxy]-ethyl ester, pyridin-2-ylcarbamic acid-2-[6-(2-tert-butyl -phenylsulfonylamino )-5-(2-methoxyphenoxy)-2-morpholin-4-yl-pyrimidin-4-yloxy]-ethyl ester, pyridin-2-yl-carbamic acid 2-[6-(4-cyclopropyl-phenyl -sulfonylamino)-5-(2-methoxy-phenoxy)-2,2'-bipyrimidin-4-yloxy]-ethyl ester, pyridin-2-ylcarbamic acid 2-[5-(2-methoxy-phenoxy)-6-(4 -methylsulfanyl-phenylsulfonyl amino )- 2,2 '-bipyrimidin-4-yl oxy ] -ethyl ester, pyridin-2-ylcarbamic acid 2-[5-(2-methoxy-phenoxy)-6-(4-vinyl -phenylsulfonylamino)-2,2'-bipyrimidin-4-yloxy]-ethyl ester, pyridyl-2-ylcarbamic acid 2-[5-(2-bromo-5-methoxy-phenoxy)-6 -(4-tert-butyl-phenylsulfonylamino)-pyrimidin-4-yloxy]-ethyl ester, pyridin-2-ylcarbamic acid 2-[6-(4-tert-butyl -phenylsulfonylamino)-5-(3,4-dimethoxy-phenoxy)-pyrimidin-4-yloxy]-ethyl ester, pyridin-2-ylcarbamic acid 2-[5-(2-chloro-5-methoxy-phenoxy)-6 -(3,4-dimethoxy-phenylsulfonylamino)-pyrimidin-4-yloxy]-ethyl ester, acetic acid 2-[4-5-(2-methoxy-phenoxy)-6-(2-pyridin-2 -ylcarbamoyloxy-ethoxy)-pyrimidin-4-ylsulfamoyl]-phenoxy]-ethyl ester, pyridin-2-ylcarbamic acid 2-[6-[4-(2-hydroxy-ethoxy)-phenyl -sulfonylamino]-5-(2-methoxy-phenoxy)-pyrimidin-4-yloxy]-ethyl ester, pyridin-2-ylcarbamic acid 2-[6-[4-methoxy-3-[2-morpholin-4-yl -2-oxo-ethoxy)-phenylsulfonylamino]-5-(2-methoxy-phenoxy) -pyrimidin-4-yloxy]-ethyl ester, acetic acid 2-[4-[5-(2-chloro-5-methoxy-phenoxy)-6-(2-pyridin-2 -ylcarbamoyloxy-ethoxy)-pyrimidin-4-ylsulfamoyl]-phenoxy]-ethyl ester, pyridin-2-ylcarbamic acid 2-[5-(2-chloro-5-methoxy-phenoxy)-6 -[ 4-(2-hydroxy-ethoxy)-phenylsulfonylamino ] -pyrimidin-4-yl oxy] -ethyl ester, pyridin-2-ylcarbamic acid 2-[5-(2-chloro-5-methoxy-phenoxy)-6 -[4-methoxy-3-(2-morpholin-4-yl-2-oxo-ethoxy)-phenylsulfonyl-amino]-pyrimidin-4-yloxy]-ethyl ester, pyridin-2-ylcarbamic acid 2'-[5-(2-chloro-5-methoxy-phenoxy)-6 -[4-(2-morpholin-4-yl-2-oxo-ethoxy]-phenyl-sulfonylamino]-pyrimidin-4 -yloxy]-ethyl ester, pyridin-2-ylcarbamic acid 2-[5-(2-methoxy-phenoxy)-6-[4-(2 -morpholin-4-yl-2-oxo-ethoxy)-phenylsulfonylamino] -pyrimidin-4 -yloxy]-ethyl ester, pyridin-2-ylcarbamic acid 2-[5-(2-methoxy-phenoxy)-6-[4-(3 -morpholin-4-yl-3-oxo-propyl)-phenylsulfonylamino] -pyrimidin-4 -yloxy]-ethyl ester, pyridin-2-ylcarbamic acid 2-[5-(2-chloro-5-methoxy-phenoxy)-6 -4-(3-morpholin-4-yl-3-oxo-propyl)-phenylsulfonylamino ]-pyrimidin-4 -yloxy]-ethyl ester, pyridin-2-ylcarbamic acid 2-[6-[4-methoxy-3-(3-morpholin-4-yl -3-oxo-propyl)-phenylsulfonylamino]-5-(2-methoxy-phenoxy) -pyrimidin-4-yloxy]-ethyl ester, pyridin-2-ylcarbamic acid 2-[5-(2-chloro-5-methoxy-phenoxy)-6 -[ 4-methoxy-3-(3-morpholin-4-yl-3-oxo-propyl)-phenylsulfonylamino]-pyrimidin-4-yloxy]-ethyl ester, pyridin-2-ylcarbamic acid 2-[5-(4-methoxy-phenoxy)-6-[4 -methoxy- 3 -(3 -piperidin-1-yl-3-oxo-propyl)-phenylsulfonylamino] -pyrimidin-4-yloxy]-ethyl ester, pyridin-2-ylcarbamic acid 2-[5-(2-methoxy-phenoxy)-6-[4 -methoxy-3-(3-piperidin-1-yl-3-oxo-propyl)-phenylsulfonylamino]-2,2'-bipyrimidin-4-yloxy]-ethyl ester, pyridin-2-ylcarbamic acid 2-[6-[4-methoxy-2-(3-morpholin-4-yl -3 -oxo-propyl)-phenylsulfonylamino ] -5 -(2-methoxy-phenoxy) -pyrimidin-4-yloxy]-ethyl ester, pyridin-2-ylcarbamic acid 2-[6-[4-(2-bromo-ethoxy) -phenylsulfonylamino]-5-(2-methoxy-phenoxy)-pyrimidin-4-yloxy]-ethyl ester, acetic acid 3-[4-[5-(2-methoxy-phenoxy)-6-(2-pyridin-2 -ylcarbamoyloxy-ethoxy)-pyrimidin-4-ylsulfamoyl]-phenoxy]-propyl ester, pyridin-2-ylcarbamic acid 2-[6-[4-(3-hydroxy-propoxy)-phenyl -sulfonylamino]-5-(2-methoxy-phenoxy)-pyrimidin-4-yloxy]-ethyl ester, pyridin-2-ylcarbamic acid 2-[6-[4-methoxy-3-(2-morpholin-4-yl -2-oxo-ethyl)-phenylsulfonylamino]-5-(2-methoxy-phenoxy)-pyrimidin -4-yloxy]-ethyl ester, pyridin-2-ylcarbamic acid 2-[6-(1,3-benzodioxol-5 -ylsulfonylamino)-2-(2-benzyloxy-ethyl]-5-(2-chloro-5-methoxy -phenoxy)-pyrimidin-4-yloxy]-ethyl ester, pyridin-2-ylcarbamic acid 2-[5-(2-chloro-5-methoxy-phenoxy)-6 -(3-isopropyl-4-methoxy-phenylsulfonylamino)-pyrimidin-4-yloxy]-ethyl ester, pyridin-2-ylcarbamic acid 2-[6-(1,3-benzodioxol-5-ylsulfonylamino)-5-(2-chloro-5-methoxy-phenoxy)-2-(3-methoxy-propyl)-pyrimidin-4-yloxy]-ethyl ester, pyridin-2-ylcarbamic acid 2-[6-(4-dimethylaminophenyl-sulfonylamino)-5-(2-methoxy-phenoxy)-2-morpholin-4-yl-pyrimidin-4-yloxy]ethyl ester, pyridin-3-ylcarbamic acid 2-[5-(2-chloro-5-methoxy-phenoxy]-6-(2,3-dihydro-1,4-benzodioxin-6-ylsulfonylamino)-pyrimidin-4-yl oxy]-ethyl ester, pyridin-4-ylcarbamic acid 2-[6-(1,3-benzodioxol-5-ylsulfonylamino)-5-(2-chloro-5-methoxy-phenoxy)-pyrimidin-4-yloxy]-ethyl ester, pyridin-3-ylcarbamic acid 2-[6-(1,3-benzodioxol-5-ylsulfonylamino)-5-(2-chloro-5-methoxy-phenoxy)-pyrimidin-4-yloxy)-ethyl ester, pyridin-3-ylcarbamic acid 2-[6-(4-tert-butyl-phenylsulfonylamino)-5-(2-chloro-5-methoxy-phenoxy)-2-methoxy-methyl-pyrimidin-4-yloxy]-ethyl ester, pyridin-3-ylcarbamic acid 2-[6-(4-tert-butylphenylsulfonylamino)-5-(2-chloro-5-methoxy-phenoxy)-pyrimidin-4-yloxy]ethyl ester, pyridin-4-ylcarbamic acid 2-[6-(4-tert-butylphenylsulfonylamino)-5-(2-chloro-5-methoxy-phenoxy)-pyrimidin-4-yloxy]ethyl ester, 1-oxy-pyridin-4-ylcarbamic acid 2-[6-(4-tert-butyl-phenylsulfonylamino)-5-(2-chloro-5-methoxyphenoxy)-pyrimidin-4-yloxy]-ethyl ester, 3-[2-[5-(2-chloro-5-methoxy-phenoxy)-6-(2,3-dihydro-1,4-benzodioxin-6-ylsulfonylamino)-pyrimidin-4-yloxy]-ethoxycarbonylamino]-1-methyl-pyridinium iodide, N-[5-(2-chloro-5-methoxy-phenoxy)-6-[2-(1-methyl-pyridin-3-ylcarbamoyloxy)-ethoxy]-pyrimidin-4-yl]-1,3-benzodioxol-5-sulfonamide, pyridin-4-ylcarbamic acid 2-[6-(4-tert-butyl-phenylsulfonylamino)-5-(3-methoxy-phenoxy)-pyrimidin-4-yloxy]ethyl ester, 4-[2-[6-(4-tert-butyl-phenylsulfonylamino)-5-(2-chloro-5-methoxy-phenoxy-pyrimidin-4-yloxy]-ethoxycarbonylamino]-1-methyl-pyridinium iodide, pyridin-4-ylcarbamic acid 2-[6-(4-tert-butyl-phenylsulfonylamino)-2-isopropyl-5-(2-methoxy-phenoxy)-pyrimidin-4-yloxy]-ethyl ester, pyridin-4-ylcarbamic acid 2-[6-(4-tert-butyl-phenylsulfonylamino)-5-(2-methoxy-phenoxy)-2-propyl-pyrimidin-4-yloxy]-ethyl ester, pyridin-4-ylcarbamic acid 2-[2-tert-butyl-6-(4-tert-butylphenylsulfonylamino)-5-(2-methoxy-phenoxy)-pyrimidin-4-yloxy]-ethyl ester, pyridin-4-ylcarbamic acid 2-[6-(4-tert-butyl-phenylsulfonylamino)-2-cyclopropyl-5-(2-methoxy-phenoxy)-pyrimidin-4-yloxy]-ethyl ester, pyrimidin-4-ylcarbamic acid 2-[6-(4-tert-butyl-phenylsulfonylamino)-5-(2-methoxy-phenoxy)-2-thiophen-2-yl-pyrimidin-4-yloxy]-ethyl ester, pyridin-4-ylcarbamic acid 2-[6-(4-tert-butyl-phenylsulfonylamino)-5-(2-methoxy-phenoxy)-2-methyl-pyrimidin-4-yloxy]-ethyl ester, pyridin-4-ylcarbamic acid 2-[6-(4-tert-butyl-phenylsulfonylamino)-5-(2-methoxy-phenoxy)-2,2'-bipyrimidin-4-yloxy]-ethyl ester, pyridin-4-ylcarbamic acid 2-[6-(2-tert-butyl-phenylsulfonylamino)-5-(2-methoxy-phenoxy)-2-morpholin-4-yl-pyrimidin-4-yloxy]-ethyl ester, pyridin-3-ylcarbamic acid 2-[6-(2-tert-butyl-phenylsulfonylamino)-5-(2-methoxy-phenoxy)-2-morpholin-4-yl-pyrimidin-4-yloxy]-ethyl ester, pyridin-4-ylcarbamic acid 2-[6-(4-tert-butyl-phenylsulfonylamino)-5-(3,4-dimethoxy-phenoxy)-pyrimidin-4-yloxy]-ethyl ester, acetic acid 2-[4-5-(2-methoxy-phenoxy)-6-(2-pyridin-4-ylcarbamoyloxy-ethoxy)-pyrimidin-4-ylsulfamoyl]-phenoxy]-ethyl ester, acetic acid 2-[4-[5-(2-methoxy-phenoxy)-6-(2-pyridin-4-ylcarbamoyloxy-ethoxy)-pyrimidin-4-ylsulfamoyl]-phenoxy]-ethyl ester, pyridin-4-ylcarbamic acid 2-[6-[4-(2-hydroxy-ethoxy)-phenyl-sulfonylamino]-5-(2-methoxy-phenoxy)-pyrimidin-4-yloxy]-ethyl ester, pyridin-3-ylcarbamic acid 2-[6-[4-(2-hydroxy-ethoxy)-phenylsulfonylamino]-5-(2-methoxy-phenoxy)-pyrimidin-4-yloxy]-ethylester, pyridin-4-ylcarbamic acid 2-[6-[4-methoxy-3-[2-morpholin-4-yl 2-oxo-ethoxy)-phenylsulfonylamino]-5-(2-methoxy-phenoxy)-pyrimidin-4-yl oxy]-ethylester, pyridin-4-ylcarbamic acid 2-[5-(2-chloro-5-methoxy-phenoxy)-6-[4-methoxy-3-(2-morpholin-4-yl-2-oxo-ethoxy)-phenylsulfonylamino]-pyrimidin-4-yloxy]-ethyl ester, pyridin-4-ylcarbamic acid 2-[5-(2-methoxy-phenoxy)-6-[4-(2-morpholin-4-yl-2-oxo-ethoxy)-phenylsulfonylamino]-pyrimidin-4-yloxy]-ethyl ester.

Examples of compounds of formula I wherein Y=-OC(O)NR$^{10}$R11, R$^{10}$ is heterocyclyl and R$^{11}$ is hydrogen are:

1-methyl-pyrrol-2-ylcarbamic acid 2-[6-(1,3-benzodioxol-5-ylsulfonylamino)-5-(2-chloro-5-methoxy-phenoxy)-pyrimidin-4-yloxy]-ethyl ester, thiophen-3-ylcarbamic acid 2-[6-(4-tert-butyl-phenylsulfonylamino)-5-(2-chloro-5-methoxy-phenoxy)-pyrimidin-4-yloxy]-ethyl ester, thiophen-3-ylcarbamic acid 2-[6-(1,3-benzodioxol-5-ylsulfonylamino)-5-(2-chloro-5-methoxy-phenoxy)-pyrimidin-4-yloxy]-ethyl ester, thiophen-3-ylcarbamic acid 2-[6-(1,3-benzodioxol-5-ylsulfonylamino)-5-(2-chloro-5-methoxy-phenoxy)-2-methoxymethyl-pyrimidin-4-yloxy]-ethyl ester, thiophen-2-ylcarbamic acid 2-[6-(1,3-benzodioxol-5-ylsulfonylamino)-5-(2-chloro-5-methoxy-phenoxy)-pyrimidin-4-yloxy]-ethyl ester, thiophen-3-ylcarbamic acid 2-[6-(1,3-benzodioxol-5-ylsulfonylamino)-5-(2-chloro-5-methoxy-phenoxy)-2-(2-methoxy-ethyl)-pyrimidin-4-yloxy]-ethyl ester, pyrazin-2-ylcarbamic acid 2-[6-(4-tert-butylphenylsulfonylamino)-5-(2-chloro-5-methoxy-phenoxy)-pyrimidin-4-yloxy]ethyl ester, quinolin-2-ylcarbamic acid 2-[6-(4-tert-butyl-phenylsulfonylamino)-5-(3-methoxy-phenoxy)-pyrimidin-4-yloxy]-ethyl ester, furan-3-ylcarbamic acid 2-[6-(1,3-benzodioxol-5-ylsulfonylamino)-5-(2-chloro-5-methoxy-phenoxy)-pyrimidin-4-yloxy]-ethyl ester, furan-2-ylcarbamic acid 2-[6-(4-tert-butyl-phenylsulfonylamino)-5-(2-methoxy-phenoxy)-2-morpholin-4-yl-pyrimidin-4-yloxy]-ethyl ester, 3-methyl-isoxazol-5-ylcarbamic acid 2-[6-(4-tert-butyl-phenylsulfonylamino)-5-(2-methoxy-phenoxy)-2-morpholin-4-yl-pyrimidin-4-yloxy]-ethyl ester, 3-methyl-isoxazol-5-ylcarbamic acid 2-[5-(2-methoxy-phenoxy)-6-(4-methylsulfanyl-phenylsulfonylamino)-2,2'-bipyrimidin-4-yloxy-ethyl ester, pyrazin-2-ylcarbamic acid 2-[6-[4-methoxy-3-[2-morpholin-4-yl-2-oxo-ethoxy)-phenylsulfonylamino]-5-(2-methoxy-phenoxy)-pyrimidin-4-yloxy]-ethyl ester, pyrazin-2-ylcarbamic acid 2-[5-(2-chloro-5-methoxy-phenoxy)-6-[4-methoxy-3-(2-morpholin-4-yl-2-oxo-ethoxy)-phenylsulfonylamino]-pyrimidin-4-yloxy]-ethyl ester, pyrazin-2-ylcarbamic acid 2-[5-(2-chloro-5-methoxy-phenoxy)-6 -[4-(2-morpholin-4-yl-2-oxo-ethoxy]-phenylsulfonylamino]-pyrimidin-4 -yloxy]-ethyl ester, pyrimidin-2-ylcarbamic acid 2-[5-(2-chloro-5-methoxy-phenoxy) -6-[4-methoxy-3-(3-morpholin-4-yl-3-oxo-propyl) -phenylsulfonylamino]-pyrimidin-4-yloxy]-ethyl ester.

Examples of compounds of formula I wherein Y= -OC(O)NR$^{10}$R$^{11}$, R$^{10}$ is aryl or cyclo-lower-alkyl and R$^{11}$ is hydrogen are:

1,3-benzodioxol-5-ylcarbamic acid 2-[6-(4-tert-butyl -phenylsulfonylamino)-5-(2-chloro-5-methoxy-phenoxy)-pyrimidin-4 -yloxy]-ethyl ester, 3-fluorophenylcarbamic acid 2-[6-(4-tert -butylphenylsulfonylamino)-5-(2-chloro-5-methoxy-phenoxy) -pyrimidin-4-yloxy]-ethyl ester, 2-fluorophenylcarbamic acid 2-[(6-(4-tert-butyl-phenyl -sulfonylamino)-5-(2-chloro-5-methoxy-phenoxy)-pyrimidin-4-yloxy]-ethyl ester, phenylcarbamic acid 2-[6-(4-tert-butyl-phenylsulfonylamino)-5 -(2-chloro-5-methoxy-phenoxy)pyrimidin-4-yloxy]-ethyl ester, 4-chloro-phenylcarbamic acid 2-[6-(4-tert-butyl-phenyl -sulfanoylamino)-5-(2-chloro-5-methoxy-phenoxy)-pyrimidin-4-yloxy] -ethyl ester, 3-methoxy-phenylcarbamic acid 2-[6-(4-tert-butyl-phenyl -sulfonylamino)-5-(2-chloro-5-methoxy-phenoxy)-pyrimidin-4-yloxy]-ethyl ester, 4-trifluoromethyl-phenylcarbamic acid 2-[6-(4-tert-butyl -phenylsulfonylamino)-5-(2-chloro-5-methoxy-phenoxy)-pyrimidin-4 -yloxy]-ethyl ester, 2-[2-[6-(4-tert-butyl-phenylsulfonylamino)-5-(2-chloro-5 -methoxy)-pyrimidin-4-yloxy]-ethoxycarbonylamino]-benzoic acid methyl ester, 3-tolylcarbamic acid 2-(6-(4-tert-butyl-phenylsulfonylamino)-5 -(2-chloro-5-methoxy-phenoxy)-pyrimidin-4-yloxy]-ethyl ester, 2-methoxy-phenoxycarbamic acid 2-[6-(4-tert-butyl -phenylsulfonylamino)- 5 -(2-chloro- 5 -methoxy-phenoxy)-pyrimidin-4 -yloxy]-ethyl ester, acetic acid 2-[2-[(6-tert-butyl-phenylsulfonylamino)-5-(2-chloro -5-methoxy)-pyrimidin-4-yloxy]-ethoxycarbonylamino]-phenyl ester, 2-hydroxy-phenylcarbamic acid 2-[6-(4-tert-butylphenylsulfonyl -amino)-5-(2-chloro-5-methoxy-phenoxy)-pyrimidin-4-yloxy]-ethyl ester, benzylcarbamic acid 2-[6-(4-tert-butylphenylsulfonylamino)-5-(2 -chloro-5-methoxy-phenoxy)pyrimidin-4-yloxy]-ethyl ester, phenylcarbamic acid 2-[6-(4-tert-butyl-phenylsulfonylamino)-5 -(3-methoxy-phenoxy)-pyrimidin-4-yloxy]-ethyl ester, (R)-1-phenyl-ethylcarbamic acid-2-[6-(4-tert-butyl-phenyl -sulfonylamino)-5-(3-methoxy-phenoxy)-pyrimidin-4-yloxy]-ethyl ester, cyclohexylcarbamic acid 2-[6-(4-tert-butyl-phenylsulfonylamino) -5-(3-methoxy-phenoxy)-pyrimidin-4-yloxy]-ethyl ester, acetic acid 2-[4-[5-(2-methoxy-phenoxy)-6-(2-phenyl -carbamoyloxy-ethoxy)-pyrimidin-4-ylsulfamoyl]-phenoxy]-ethyl ester, acetic acid 2-[4-[6-[2-(2-fluoro-phenylcarbamoyloxy)-ethoxy]-5 -(2-methoxy-phenoxy)-pyrimidin-4-ylsulfamoyl] -phenoxy]-ethyl ester, phenylcarbamic acid 2-[6-[4-(2-hydroxy-ethoxy)-phenyl -sulfonylamino]-5-(2-methoxy-phenoxy)-pyrimidin-4-yloxy]-ethyl ester, 2-fluoro-phenylcarbamic acid 2-[6-[4-(2-hydroxy-ethoxy) -phenylsulfonylamino]-5-(2-methoxy-phenoxy)-pyrimidin-4-yloxy]-ethyl ester, 2-fluoro-phenylcarbamic acid 2-[6-[4-methoxy-3-(2-morpholin-4 -yl-2-oxo-ethoxy)-phenylsulfonylamino]-5-(2-methoxy-phenoxy) -pyrimidin-4-yloxy]-ethyl ester, acetic acid 2-[4-[5-(2-chloro-5-methoxy-phenoxy)-6-[2-(2-fluoro -phenylcarbamoyloxy)-ethoxy]-pyrimidin-4-ylsulfamoyl]-phenoxy]-ethyl ester, 2-fluoro-phenylcarbamic acid 2-[5-(2-chloro-5-methoxy -phenoxy)-6-[4-(2-hydroxy-ethoxy)-phenylsulfonylamino]-pyrimidin-4 -yloxy]-ethyl ester, 2-fluoro-phenylcarbamic acid 2-[5-(2-chloro-5-methoxy -phenoxy)-6-[4-methoxy-3-(2-morpholin-4-yl-2-oxo-ethoxy) -phenylsulfonylamino]-pyrimidin-4-yloxy]-ethyl ester, phenylcarbamic acid 2-[6-[4-methoxy-3-(2-morpholin-4-yl-2-oxo -ethoxy)-phenylsulfonylamino]-5-(3-methoxy-phenoxy)-pyrimidin-4 -yloxy]-ethyl ester,

[ 5-[ 5-(2-chloro-5-methoxy-phenoxy)-6-[ 2-(2 -fluorophenylcarbamoyloxy)-ethoxy ]-pyrimidin-4-ylsulfamoyl ] -2 -methoxy-phenoxy]-acetic acid ethyl ester, 5-[ 5-(2-chloro-5-methoxy-phenoxy)-6-[ 2-(2-fluoro-phenyl -carbamoyloxy)-ethoxy]-pyrimidin-4-ylsulfamoyl]-2-methoxy-phenoxy]-acetic acid, 2-fluoro-phenylcarbamic acid 2-[6-[4-methoxy-3-(2-oxo-2 -piperidin- 1-yl-ethoxy)-phenylsulfonylamino ] - 5 -(2-methoxy-phenoxy) -pyridin-4-yloxy]-ethyl ester.

Examples of compounds of formula I wherein Y= -OC(O)NR$^{10}$R$^{11}$ are:

isopropylcarbamic acid 2-[6-(4-tert-butyl-phenylsulfonylamino) -5-(2-chloro-5-methoxy-phenoxy)-pyrimidin-4-yloxy]-ethyl ester, ethylcarbamic acid 2-[6-(4-tert-butyl-phenylsulfonylamino)-5-(2 -chloro-5-methoxy-phenoxy)-pyrimidin-4-yloxy]-ethyl ester,

[2-[6-(4-tert-butyl-phenylsulfonylamino)-5-(3-methoxy -phenoxy)-pyrimidin-4-yloxy]-ethoxycarbonylamino]-acetic acid ethyl ester, 2-[6-(4-tert-butyl-phenylsulfonylamino)-5-(3-methoxy-phenoxy) -pyrimidin-4-yloxy]-ethoxycarbonylaminoacetic acid, 2-hydroxy-ethylcarbamic acid 2-[6-(4-tert-butyl-phenyl-sulfonyl -amino)-5-(3-methoxy-phenoxy)-pyrimidin-4-yloxy]-ethyl ester, morpholine-4-carboxylic acid 2-[6-(4-tert-butyl-phenyl-sulfonyl -amino)-5-(3-methoxy-phenoxy)-pyrimidin-4-yloxy]-ethyl ester, 2-morpholin-4-yl-2-oxo-ethylcarbamic acid 2-[6-(4-tert-butyl -phenylsulfonylamino)-5-(3-methoxy-phenoxy)-pyrimidin-4-yloxy]-ethyl ester, 2-oxo-2-pyrrolidin-1-yl-ethylcarbamic acid 2-[6-(4-tert-butyl -phenylsulfonylamino)-5-(3-methoxy-phenoxy)-pyrimidin-4-yloxy]-ethyl ester, phenylcarbamoylmethylcarbamic acid 2-[6-(4-tert-butyl -phenylsulfonylamino)- 5 -(3 -methoxy-phenoxy)-pyrimidin-4- yloxy ] ethyl ester, 2-[2-[6-(4-tert-butyl-phenylsulfonylamino)-5-(3-methoxy -phenoxy)-pyrimidin-4-yloxy]-ethoxycarbonylamino]-4-methyl -pentanoic acid ethyl ester.

Examples of compounds of formula I wherein Y= -NHC(O)NR$^{10}$R$^{11}$ are:

4-tert-Butyl-N-[ 5-(2-chloro-5-methoxy-phenoxy)-6-[ 2-(3-phenyl -ureido)-ethoxy]-pyrimidin-4-yl ] -benzenesulfonamide, 4-tert-butyl-N-[ 5-(2-chloro-5 -methoxy-phenoxy)-6-[ 2-[ 3 -(2 -fluoro-phenyl)-ureido]-ethoxy]-pyrimidin-4-yl]-benzenesulfonamide, 4-tert-butyl-N-[ 5-(2-chloro-5-methoxy-phenoxy)-6-[ 2-(3-pyridin -2-yl-ureido)-ethoxy]-pyrimidin-4-yl]-benzenesulfonamide 4-tert-butyl-N-[ 5-(2-chloro-5-methoxy-phenoxy)-6-[2-(3-pyridin -4-yl-ureido )-ethoxy ]-pyrimidin-4-yl ]-benzenesulfonamide, 4-tert-butyl-N-[ 5-(2-chloro-5-methoxy-phenoxy)-6-[2-(3-pyridin -3-yl-ureido)-ethoxy]-pyrimidin-4-yl]-benzenesulfonamide, 4-tert-butyl-N-[ 5-(2-chloro-5-methoxy-phenoxy)-6-[2-(3-1 -oxy -pyridin-4-yl)-ureido]-ethoxy]-pyrimidin-4-yl] -benzenesulfonamide, 4-tert-butyl-N-[ 5-(2-methoxy-phenoxy)- 2-methyl-6-[2-(3 -pyridin-2-yl-ureido)-ethoxy]-pyrimidin-4-yl]-benzenesulfonamide.

Examples of compounds of formula I wherein Y= -OC(O)COR$^{10}$ are:

carboxylic acid 2-[6-(1,3-benzodioxol-5-ylsulfonylamino)-5-(3,5 -dimethoxy-phenoxy)-pyrimidin-4-yloxy]-ethyl ester pyridin-3-ylmethyl ester, carboxylic acid 2-[6-(1,3-benzodioxol-5-sulfonylamino)-5-(2 -chloro-5-methoxy-phenoxy)-pyrimidin-4-yloxy]-ethyl ester pyridin-2 -ylmethyl ester, carboxylic acid 2-[6-(1,3-benzodioxol-5-ylsulfonylamino)-5-(2 -chloro-5-methoxy-phenoxy)-pyrimidin-4-yloxy]-ethyl ester pyridin-2 -ylmethyl ester, carboxylic acid 2-[6-(4-tert-butyl-benzenesulfonylamino)-5-(2 -chloro-5-methoxy-phenoxy)-pyrimidin-4-yloxy]-ethyl ester pyridin-2 -ylmethyl ester, carboxylic acid 2-[6-(1,3-benzodioxol-5-ylsulfonylamino)-5-(2 -chloro-5-methoxy-phenoxy)-pyrimidin-4-yloxy]-ethyl ester furan-3 -ylmethyl ester, carboxylic acid 2-[6-(4-tert-butyl-phenylsulfonylamino)-5-(2 -chloro-5-methoxy-phenoxy)-2-methyl-pyrimidin-4-yloxy]-ethyl ester pyridin-3-ylmethyl ester, carboxylic acid 2-[6-(4-tert-butyl-phenylsulfonylamino)-5-(2 -chloro-5-methoxy-phenoxy)-2-methyl-pyrimidin-4-yloxy] -ethyl ester pyridin-2-ylmethyl ester, carboxylic acid 2-[6-(4-tert-butyl-phenylsulfonylamino)-5-(2 -chloro-5-methoxy-phenoxy)-2-methyl-pyrimidin-4-yloxy]-ethyl ester pyrimidin-4-ylmethyl ester, carboxylic acid 2-[6-(4-tert-butyl-phenylsulfonylamino)-5-(2 -methoxy-phenylsulfanyl)-2,2'-bipyrimidin-4-yloxy]-ethyl ester-pyridin -3 -ylmethyl ester, carboxylic acid 2-[6-(4-tert-butyl-phenylsulfonylamino)-5-(2 -methoxy-phenylsulfanyl)-2-methyl-pyrimidin-4-yloxy]-ethyl ester pyridin-3-ylmethyl ester.

Examples of compounds of formula I wherein n=1 and Z=-S- are:

pyridin-2-ylcarbamic acid 2-[6-(4-tert-butyl-phenylsulfonyl -amino)-5-(2-methoxy-phenylsulfanyl)-pyrimidin-4-yloxy)-ethyl ester, pyridin-3-ylcarbamic acid 2-[6-tert-butyl-phenylsulfonylamino) -5-(2-methoxy-phenylsulfanyl)-2,2'-bipyrimidin-4-yloxy]-ethyl ester, pyridin-4-ylcarbamic acid 2-[6-(4-tert-butyl-phenyl -sulfonylamino )- 5-(2-methoxy-phenylsulfanyl)-2-methyl-pyrimidin-4 -yloxy]-ethyl ester.

The compounds of formula I given above are inhibitors of endothelin receptors. They can accordingly be used for the treatment of disorders which are associated with endothelin activities, especially circulatory disorders such as hypertension, ischaemia, vasospasms and angina pectoris.

The invention therefore includes the use of the compounds of formula I and their salts for the treatment of the aforementioned disorders their use as active ingredients in the manufacture of medicaments for the aforementioned indications as well as pharmaceutical compositions which contain the compounds of formula I or their salts.

The compounds of formula I can be prepared in accordance with the invention by reacting a compound of the formula wherein R$^1$-R$^9$, R$^a$, R$^b$, X, Z, m and n have the significance given above and A is hydroxy or amino, a) with an isocyanate of the formula R$^{10}$NCO or a carbamoyl chloride of the formula (R$^{10}$R$^{11}$)NCOCl, wherein R$^{10}$ and R$^{11}$ have the significance given earlier or b) with phosgene and thereafter with an alcohol of the formula R$^{10}$OH; or with a chloroformate of the formula R$^{10}$OC(O)Cl, and, if desired, modifying substituents present in the thus-obtained compound of formula I and, if desired, converting a compound of formula I into a pharmaceutically usable salt.

The reaction according to process variant a) can be effected in a manner known per se for the manufacture of carbamates and ureas from alcohols and, respectively, amines. Thus, a compound of formula II in which A is hydroxy can be reacted with an isocyanate of the formula R$^{10}$NCO in a suitable anhydrous organic solvent, for example, a hydrocarbon such as toluene, conveniently while heating, to give a compound of formula I in which Y is -OC(O)NHR$^{10}$. The isocyanate can be produced in situ, for example, from an azide of the formula R$^{10}$CON$_3$ by thermal decomposition. Compounds of formula I with Y =-NH-C(O)NR$^{10}$ can be obtained in a corresponding manner using compounds of formula II in which A is amino. Alternatively, compounds of formula II in which A is hydroxy can be reacted with compound of the formula R$^{10}$R$^{11}$NC(O)Cl under analogous reaction conditions to give compounds of formula I in which Y is a residue -OC(O)NR$^{10}$R$^{11}$ and compounds of formula II in which A is amino can be converted into compounds of formula I in which Y is a residue -NHC(O)NR$^{10}$R$^{11}$.

According to process variant b), a compound of formula II in which A is hydroxy can be reacted with phosgene and thereafter with an alcohol of the formula R$^{10}$OH to give a compound of formula I in which Y is a residue -OC(O)OR$^{10}$. A phosgene salt such as diphosgene (Cl -COOCCl$_3$) or triphosgene (CO(OCC$_3$)$_2$) can be used in place of phosgene. Compounds of formula I with Y = -NHC(O)OR$^{10}$ are obtained analogously starting from compounds of formula II with A=amino. The phosgene is conveniently used as a solution in an inert anhydrous organic solvent, for example, a hydrocarbon such as toluene. The reaction with phosgene can be performed at room temperature. The acid chloride which is obtained as an intermediate is reacted immediately with the alcohol R$^{10}$OH, conveniently while heating.

Substituents present in the thus-obtained compounds of formula I can be modified. For example, ester groups can be saponified or reduced to alcohol groups; N-heterocyclic residues such as pyridyl residues can be oxidized to N-oxides or N-alkylated; carboxylic acid groups can be converted into esters or amides. Finally, the compounds of formula I can be converted into salts, for example, alkali salts such as Na and K salts or alkaline earth metal salts such as Ca or Mg salts. All of these operations can be performed in a known manner.

The compounds which are used as starting materials are generally known, for example, from European Patent Publications EP-A-0526708 and EP-A-510526, or, insofar as they are not individually known or their preparation is not described hereinafter, can be prepared in analogy to known methods or methods described hereinafter.

The inhibitory activity of the compounds of formula I on endothelin receptors can be demonstrated using the test procedures described hereinafter:

I: Inhibition of endothelin binding to recombinant $ET_A$ receptors

A cDNA coding for human ETA receptors of human placenta was cloned (M. Adachi, Y.-Y. Yang, Y. Furuichi and C. Miyamoto, BBRC 180, 1265–1272) and expressed in the baculovirus-insect cell system. Baculovirus-infected insect cells from a 23 l fermenter are centrifuged off (3000×g, 15 minutes, 4° C.) 60 hours after the infection, re-suspended in Tris buffer (5 mM, pH 7.4, 1 mM $MgCl_2$) and again centrifuged. After a further re-suspension and centrifugation the cells are suspended in 800 ml of the same buffer and freeze-dried at −120° C. The cells disintegrate when the suspension in this hypotonic buffer mixture is thawed. After a repeated freeze-drying/thawing cycle the suspension is homogenized and centrifuged (25000 ×g, 15 minutes, 4° C.). After suspension in Tris buffer (75 mM, pH 7.4, 25 mM $MgCl_2$, 250 mM saccharose) 1 ml aliquots (protein content about 3.5 mg/ml) are stored at −85° C.

For the binding assay, the freeze-dried membrane preparations are thawed and, after centrifugation at 20° C. and 25000 g for 10 minutes, re-suspended in assay buffer (50 mM Tris buffer, pH 7.4, containing 25 mM $MnCl_2$, 1 mM EDTA and 0.5% bovine serum albumin). 100 ml of this membrane suspension containing 70 mg of protein are incubated with 50ml of $^{125}I$-endothelin (specific activity 2200 Ci/mMol) in assay buffer (25000 cpm, final concentration 20 pM) and 100 ml of assay buffer containing varying concentrations of test compound. The incubation is carried out at 20° C. for 2 hours or at 4° C. for 24 hours. The separation of free and membrane-bound radio-ligands is carried out by filtration over a glass fiber filter.

The inhibitory activity of compounds of formula I determined in this test procedure is given in Table 1 as the $IC_{50}$, i.e. as the concentration [mM] which is required to inhibit 50% of the specific binding of $^{125}I$-endothelin.

TABLE 1

| Compound of Example | $IC_{50}$ [mM] |
|---|---|
| 10 | 0.001 |
| 70 | 0.006 |
| 75 | 0.003 |
| 120 | 0.007 |
| 134 | 0.044 |
| 140 | 0.009 |

II. Inhibition of endothelin-induced contractions in isolated rat aorta rings

Rings with a length of 5 mm were cut out from the thorax aorta of adult Wistar-Kyoto rats. The endothelium was removed by lightly rubbing the internal surface. Each ring was immersed at 37° C. in 10 ml of Krebs-Henseleit solution in an isolated bath while gassing with 95% $O_2$ and 5% $CO_2$. The isometric stretching of the tings was measured. The rings were stretched to a pre-tension of 3 g. After incubation for 10 minutes with the test compound or vehicle cumulative dosages of endothelin-1 were added. The activity of the test compound was ascertained by the observed shift to the right of the dosage-activity curve of endothelin-1 in the presence of different concentrations of antagonist. This shift to the right (or "dose ratio", DR) corresponds to the quotient from the $EC_{50}$ values of endothelin-1 in the presence and in the absence of antagonist, with the $EC_{50}$ value denoting the endothelin concentration required for a half-maximum contraction.

The corresponding $PA_2$ value, which is a measure of the activity of the test compound, was calculated using a computer programme according to the following equation from the "dose ratio" DR for each individual dosage-activity curve.

$$pA_2 = \log(DR-1) - \log(\text{antagonist-concentration})$$

The $EC_{50}$ of endothelin in the absence of test compounds is 0.3 nM. The $pA_2$ values obtained with compounds of formula I are given in Table 2.

TABLE 2

| Compound of Example | Dose ratio (switch to the right) |
|---|---|
| 10 | 8.2 |
| 70 | 9.0 |
| 75 | 7.3 |
| 120 | 7.2 |
| 134 | 7.3 |
| 140 | 7.0 |

III. The in vivo activity of the compounds of formula I can be demonstrated as follows in a pathophysiologically relevant rat model:

A telemetric system (PA-C40 implant) was implanted into "stroke-prone", spontaneously hypertensive rats under anaesthesia in order that the arterial blood pressure and the heart rate could be measured continuously. The animals were left to recover for 2 weeks after the operation.

Telemetric measurements showed that the average arterial blood pressure of the animals had increased and was about 190 mm Hg. The corresponding test compound (30 mg/kg in gum arabic) was finally administered using a probe and the blood pressure was registered continuously. It became evident that compounds of formula I caused a fall in blood pressure, the administration of gum arabic alone (placebo control) having no significant effect on the blood pressure.

The result obtained with one compound of formula I is given in Table 3.

TABLE 3

| Compound of Example | % Decrease in the average arterial blood pressure (mm Hg) |
|---|---|
| 70 | 30 |

On the basis of their capability of inhibiting endothelin binding, the compounds of formula I can be used as medicaments for the treatment of disorders which are associated with vasoconstriction of increasing occurrences. Examples of such disorders are high blood pressure, coronary disorders, cardiac insufficiency, renal and myocardial ischaemia, renal insufficiency, dialysis, cerebral ischaemia, cerebral infarct, migraine, subarachnoid haemorrhage, Raynaud syndrome and pulmonary high pressure. They can also be used in atherosclerosis, the prevention of restenosis after balloon-induced vascular dilation, inflammations, gastric and duodenal ulcers, ulcus cruris, gram-negative sepsis, shock, glomerulonephtritis, renal colic, glaucoma, asthma, in the therapy and prophylaxis of diabetic complications and complications in the administration of cyclosporin, as well as other disorders associated with endothelin activities.

The compounds of formula I can be administered orally, rectally, parentally, for example, intravenously, intramuscularly, subcutaneously, intrathecally or transdermally; or sublingually or as opththalmological preparations, or as an areosol. Capsules, tablets, suspensions or solutions for oral administration, suppositories, injection solutions, eye drops, salves or spray solutions are examples of administration forms.

Intravenous, intramuscular or oral administration is preferred. The dosages in which the compounds of formula I are administered in effective amounts depend on the nature of the specific active ingredient, the age and the requirements of the patient and the mode of administration. In general, dosages of about 0.1–100mg/kg body weight per day come into consideration. The preparations containing the compounds of formula I can contain inert or also pharmacodynamically active additives. Tablets or granulates for example, can contain a series of binders, fillers, carriers or diluents. Liquid preparations can be present, for example, in the form of a sterile water-miscible solution. Capsules can contain a filler or thickener in addition to the active ingredient. Furthermore, flavor-improving additives as well as substances usually used as preserving, stabilizing, moisture-retaining and emulsifying agents as well as salts for varying the osmotic pressure, buffers and other additives can also be present.

The previously mentioned carrier materials and diluents can comprise organic or inorganic substances, for example, water, gelatine, lactose, starch, magnesium stearate, talc, gum arabic, polyalkylene glycols and the like. It is a prerequisite that all adjuvants used in the manufacture of the preparations are non-toxic.

The following Examples illustrate the invention in more detail. Of the abbreviations used therein THF is tetrahydrofuran; DMSO is dimethyl sulfoxide; MeOH is methanol; b.p. is boiling point; and m.p. is melting point.

Example 1 a) 57 mg of 3-pyridyl isocyanate were added to 121.5 mg of N-[5-(2-chloro-5-methoxy-phenoxy)-6-(2-hydroxyethoxy)-pyrimidin-4-yl]-2,3-dihydro-1,4-benzodioxin-6-sulfonamide dissolved in 1 ml of dry toluene. The reaction mixture was stirred at 100° C. for 1 hour. Then, the solution was added to a silica gel column and it was eluted with EtOAc. There was obtained pyridin-3-ylcarbamic acid 2-[5-(2-chloro-5-methoxy-phenoxy)-6-(2,3-dihydro-1,4-benzodioxin-6-ylsulfonylamino)-pyrimidin-4-yloxy]-ethyl ester, white powder, MS: m/e = 630.4 (M+H)$^+$.

Preparation of the starting material b) 3-Methoxyphenol was converted into 2-chloro-5-methoxyphenol using sulfuryl chloride according to the procedure of M. Julia and I. de Rosnay, Chimie Therapeutique 5 (1969), 334.

c) 18.2 g of 2-chloro-5-methoxyphenol were dissolved in 150ml of dry methanol. 9.3 g of MeONa followed by 25 g of dimethyl chloromalonate were added. The reaction mixture was stirred at 50° C. for 2 hours. After distillation of the solvent the residue was partitioned between toluene and H$_2$O in a separating funnel and washed neutral. After crystallization in ethanol there was obtained dimethyl (2-chloro-5-methoxy)phenoxy-malonate, white crystals with m.p. 68°–69° C.

d) 1.43 g of Na were dissolved in 70 ml of MeOH. Then, 5.8 g of dimethyl (2-chloro-5-methoxy)phenoxy-malonate and 2.29 g of formamidine acetate were added; the reaction mixture was stirred under reflux for 1.5 hours. Then, the solvent was distilled off, the residue was taken up in H$_2$O, the aqueous phase was extracted with ethyl acetate, the organic phase was discarded and the aqueous phase was acidified to pH 4 with acetic acid, whereby 5-(2-chloro-5-methoxy)phenoxy-4,6(1H,5H)-pyrimidinedione separated as a white powder. MS: m/e = 268 (M).

e) A mixture of 3.75 g of 5-(2-chloro-5-methoxy)phenoxy-4,6(1H,5H)-pyrimidinedione, 5.4 g of N-ethyldiisopropylamine and 12.5 ml of POCl$_3$ in 20 ml of dioxane was stirred under reflux for 18 hours. After distilling off the volatile components the residue was partitioned between ethyl acetate and H$_2$O and washed neutral. After distilling off the solvent the compound was purified on silica gel with CH$_2$Cl$_2$ as the eluent. After crystallization from EtOH there was obtained 4,6-dichloro-5-(2-chloro-5-methoxy-phenoxy)-pyrimidine as white crystals with m.p. 88°–89° C.

f) A Vilsmeier reagent was prepared by adding 29 g of sulfuryl chloride dropwise to 15.7 g of DMF. Subsequently, 27.3 g of 1,2-ethylenedioxy-benzene were added dropwise. After termination of the addition the reaction mixture was stirred at 100° C. for one hour. Then, the solution was poured on to ice and the sulfochloride formed was extracted with CH$_2$Cl$_2$. After distilling off the dichloromethane the residue was taken up in THF. 10 ml of 25% NH$_4$OH solution were added and the mixture was stirred for 0.5 hour. The 1,4-benzodioxan-6-sulfonamide formed was crystallized from ethyl acetate. Pale yellow crystals were obtained. The sulfonamide was converted into the K salt by addition of the stoichiometric amount of KOH.

g) 917 mg of 4,6-dichloro-5-(2-chloro-5-methoxy-phenoxy)-pyrimidine and 1.29 g of the 1,4-benzodioxane-6-sulfonamide salt from 1 f) were dissolved in 4 ml of DMSO. The reaction had finished after 1 hour at 100 ° C. After distilling off the solvent the residue was partitioned between 1N HCl and ethyl acetate. After isolating the reaction product the N-[6-chloro-5-(2-chloro-5-methoxy-phenoxy)-pyrimidin-4-yl]-2,3-dihydro-1,4-benzodioxane-6-sulfonamide was crystallized from propanol. M.p. 185°–186° C.

h) 485 mg of N-[6-chloro-5-(2-chloro-5-methoxy-phenoxy)-pyrimidin-4-yl]-2,3-dihydro-1,4-benzodioxane-6-sulfonamide were added to a Na glycolate solution (115 mg of Na in 2 g of ethylene glycol). The mixture was left to react at 100 ° C. for 1 hour. After isolating the reaction product it was chromatographed on silica gel with dichloromethane-diethyl ether (1:1 in vol.) as the eluent. Crystallization was carried out from diisopropyl ether and there was obtained N-[5-(2-chloro-5-methoxy-phenoxy)-6-(2-hydroxyethoxy)-pyrimidin-4-yl]-2,3-dihydro-1,4-benzodioxane-6-sulfonamide as white crystals with m.p. 180°–181° C.

Example 2 a) A solution of 100 mg of 4-pyridylcarboxylic acid azide in 2 ml of absolute toluene was held at 100° C. for 1 hour, whereby the corresponding isocyanate was formed. Then, 100 mg of N-[5-(2-chloro-5-methoxy-phenoxy)-6-(2-hydroxy-ethoxy)-pyrimidin-4-yl]-1,3-benzodioxol-5-sulfonamide were added and the mixture was left to react at this temperature for 2 hours. Then, the reaction solution was added to a silica gel column and it was eluted with ethyl acetate. The resulting pyridin-4-ylcarbamic acid 2-[6-(1,3-benzodioxol-5-ylsulfonylamino)-5 -(2-chloro-5-methoxy-phenoxy)-pyrimidin-4-yloxy]-ethyl ester was crystallized from CHCl$_3$. M.p. 230° C. (dec.).

Preparation of the starting material b) (1,3-Benzodioxol-5-sulfonamide) K was prepared from 1,3 -benzodioxol according to the procedure of Example 1, part f).

c) 458 mg of 4,6-dichloro-5-(2-chloro-5-methoxy-phenoxy) -pyrimidine and 574 mg of (1,3-benzodioxol-5-sulfonamide) K were converted into N-[6-chloro-5-(2-chloro-5-methoxy-phenoxy)-pyrimidin -4-yl]-1,3-benzodioxol-5-sulfonamide. White crystals (from MeOH). M.p. 230° C.

d) 470.3 mg of the compound from 2c) were converted with Na glycolate in ethylene glycol into N-[5-(2-chloro-5-methoxy-phenoxy)-6 -(2-hydroxy-ethoxy)-pyrimidin-4-yl]-1,3-benzodioxol-5-sulfonamide. White crystals, m.p. 164° C.

e) 6.15 g of isonicotinic acid and 5.55 g of triethylamine were dissolved in 50 ml of acetone. 6 g of ethyl chloroformate were added dropwise to this solution which had been cooled to −10° C. After 2 hours a solution of 5 g of NaN$_3$ dissolved in 20 ml of H$_2$O was added dropwise at 0° C. After 1 hour at room temperature the solid was filtered off and discarded. The solution was distilled at room temperature and the residue was extracted with dichloromethane. After drying over MgSO$_4$ the solvent was distilled off and the liquid remaining behind was filtered over silica gel with dichloromethane as the eluent. There was obtained 4-pyridylcarboxylic acid azide as a colorless liquid which crystallized in a deep freezer (−18° C.). IR: 2141, 2190 cm$^{-1}$ (N$_3$).

Example 3 a) In analogy to Example 2, from 100 mg of N-[5-(2-chloro-5 -methoxy-phenoxy)-6-(2-hydroxy-ethoxy)-pyrimidin-4-yl]- 1,3 -benzodioxol-5-sulfonamide and 100 mg of 3-pyridylcarboxylic acid azide there was obtained pyridine-3-carbamic acid 2-[6-(1,3-benzodioxol-5 -ylsulfonylamino)-5-(2-chloro-5-methoxy-phenoxy)-pyrimidin-4-yloxy) -ethyl ester. M.p. 114°–115° C. (dec.).

Preparation of the starting material b) 3-Pyridylcarboxylic acid azide was prepared from nicotinic acid according to the procedure of Example 2, part c). IR: 2137, 2179 cm$^{-1}$ (N$_3$).

Example 4 a) In analogy to Example 2, from 250 mg of N-[5-(2-chloro-5 -methoxy-phenoxy)-6-(2-hydroxy-ethoxy)-pyrimidin-4-yl]- 1,3 -benzodioxol-5-sulfonamide and 225 mg of 2-pyridylcarboxylic acid azide there was obtained pyridine-2-carbamic acid 2-[6-(1,3-benzodioxol-5 -ylsulfonylamino)-5-(2-chloro-5-methoxy-phenoxy)-pyrimidin-4-yloxy]-ethyl ester. M.p. 206° C. (dec.).

Preparation of the starting material b) 2-Pyridylcarboxylic acid azide was prepared from picolinic acid according to the procedure of Example 2, part e).

Example 5 a) In analogy to Example 2, from 100 mg of 4-tert-butyl-N-[5-(2 -chloro-5-methoxy-phenoxy)-6-(2-hydroxy-ethoxy)-2-methoxymethyl]-benzenesulfonamide and 100 mg of 3-pyridylcarboxylic acid azide there was obtained pyridine-3-carbamic acid 2-[6-(4-tert-butyl -phenylsulfonylamino)-5-(2-chloro-5-methoxy-phenoxy)-2 -methoxymethyl-pyrimidin-4-yloxy]-ethyl ester. MS: m/e = 672.6 (M+H$^+$).

Preparation of the starting material b) 16 g of methoxyacetonitrile and 11.45 g of ethanol were dissolved in 50 ml of diethyl ether. The solution was saturated with dry HCl at 0° C. The solution was left to stand at room temperature for 3 days. Then, the solvent was distilled off, whereby crystallization occurred. M.p. 122° C. (dec.).

c) 15.3 g of the imidoester hydrochloride from b) were dissolved in 25 ml of methanol. 15.4 ml of a 6.5N NH$_3$ solution in methanol were poured in in one portion, whereby the precipitate which formed dissolved rapidly. The solution was left to stand at room temperature for 24 hours. Then, the solvent was distilled off, whereby crystallization occurred gradually.

d) In analogy to Example 1, part d), from 5.1 g of methoxymethyl -amidine hydrochloride and 11.2 g of dimethyl (2-chloro-5-methoxy -phenoxy)-malonate there was obtained 2-methoxymethyl-5-(2-chloro -5-methoxy-phenoxy-4,6(1H,5H)-pyrimidinedione as a white powder. MS: 312 (M).

e) In analogy to Example 1, part e), there was obtained 4,6-dichloro -2-methoxymethyl-5-(2-chloro-5-methoxy-phenoxy)-pyrimidine, m.p. 105° C. (from EtOH).

f) In analogy to Example 1, part g), from the dichloride from e) and (4-tert-butyl-benzenesulfonamide) K there was obtained 4-tert-butyl-N -[ 6-chloro-5-(2-chloro-5-methoxy-phenoxy)-2-methoxymethyl -pyrimidin-4-yl]-benzenesulfonamide. MS: 526 (M+H$^+$).

g) In analogy to Example 1, part h), from 0.3 g of the compound from Example 5, part f), there was obtained 4-tert-butyl-N-[5-(2-chloro-5 -methoxy-phenoxy)-6-(2-hydroxy-ethoxy)-2-methoxymethyl-pyrimidin -5-yl]-benzenesulfonamide. MS: 551 (M).

Example 6

In analogy to Example 2, from 100 mg of 4-tert-butyl-N-[5-(2 -chloro-5-methoxy-phenoxy)-6-(2-hydroxy-ethoxy)-2-methoxymethyl -pyrimidin-4-yl]-benzenesulfonamide and 100mg of 2-pyridylcarboxylic acid azide there was obtained pyridine-2-carbamic acid 2-[6-(4-tert -butyl-phenylsulfonylamino)-5 -(2-chloro-5-methoxy-phenoxy)-2 -methoxymethyl-pyrimidin-4-yloxy]-ethyl ester. M.p. 174°–175° C. (from EtOH).

Example 7 a) In analogy to Example 2, from 200 mg of N-[5-(2-chloro-5 -methoxy-phenoxy)-6-(2-hydroxy-ethoxy)-2-methoxymethyl-pyrimidin -4-yl]-1,3-benzodioxol-5-sulfonamide and 165 mg of 2-pyridylcarboxylic acid azide there was obtained pyridine-2-carbamic acid 2-[6-(1,3 -benzodioxol-5-ylsulfonylamino)-5-(2-chloro-5-methoxy-phenoxy)-2 -methoxymethyl-pyrimidin-4-yloxy]-ethyl ester. M.p. 160°–162° C.

Preparation of the starting material b) In analogy to Example 1, part g), from 700 mg of 4,6-dichloro-2 -methoxymethyl-5-(2-chloro-5-methoxy-phenoxy)-pyrimidine and 766 mg of (1,3-benzodioxol-5-sulfonamide) K there was obtained N-[6 -chloro-5-(2-chloro-5-methoxy-phenoxy)-2-methoxymethyl-pyrimidin -4-yl]-1,3-benzodioxol-5-sulfonamide. M.p. 114°–116° C. (from EtOH).

c) This compound was converted into N-[5-(2-chloro-5-methoxy -phenoxy)-6-(2-hydroxy-ethoxy)-2-methoxymethyl-pyrimidin-4-yl]- 1,3 -benzodioxol-5-sulfonamide in analogy to Example 1, part h).

Example 8

In analogy to Example 2, from 125 mg of N-[5-(2-chloro-5 -methoxy-phenoxy)-6-(2-hydroxy-ethoxy)-pyrimidin-4-yl]- 1,3 -benzodioxol-5-sulfonamide and 90 mg of 1-methyl-pyrrole-2-carboxylic acid azide there was obtained 1-methyl-pyrrole-2-carbamic acid 2-[6 -(1,3-benzodioxol-5-ylsulfonylamino)-5-(2-chloro-5-methoxy-phenoxy) -pyrimidin-4-yloxy]-ethyl ester. MS: 618.3 (M+H$^+$).

The 1-methyl-pyrrole-2-carboxylic acid azide was obtained as a colourless liquid, IR: 2132 cm$^{-1}$ (N$_3$), from 1-methyl-pyrrole-2 -carboxylic acid using the process of Example 2c).

Example 9

In analogy to Example 2, from 95 mg of 4-tert-butyl-N-[5-(2 -chloro-5-methoxy-phenoxy)-6-(2-hydroxy-ethoxy)-pyrimidin-4-yl]-benzenesulfonamide and 90 mg of 1,3-benzodioxol-5-carboxylic acid azide there was obtained 1,3-benzodioxol-5-ylcarbamic acid 2-[6-(4 -tert-butyl-phenylsulfonylamino)-5-(2-chloro-5-methoxy-phenoxy) -pyrimidin-4-yloxy]-ethyl ester. MS: 671.4 (M+H$^+$).

The 1,3-benzodioxol-5-carboxylic acid azide was obtained starting from the corresponding carboxylic according to the procedure of Example 2e). IR: 2144 cm$^{-1}$ (N$_3$).

Example 10 a) In analogy to Example 2, from 100 mg of N-[5-(2-chloro-5 -methoxy-phenoxy)-6-(2-hydroxy-ethoxy)-2-(2-methoxyethyl) -pyrimidin-4-yl]-1,3-benzodioxol-5-sulfonamide and 80 mg of 2 -pyridylcarboxylic acid azide there was obtained pyridine-2-ylcarbamic acid 2-[6-(1,3-benzodioxol-5-ylsulfonylamino)-5-(2-chloro-5-methoxy -phenoxy)-2-(2-methoxyethyl)-pyrimidin-4-yloxy]-ethyl ester. M.p. a 156° C. (from EtOH).

Preparation of the starting material b) In analogy to Example 5, part b), from methoxypropionitrile, HCl and ethanol there was obtained methoxyethyl-imidoethyl ester hydrochloride. MS: 116 (M-CH$_3$).

c) Methoxyethyl-amidine hydrochloride was obtained in analogy to Example 5, part c).

d) In analogy to Example 1, part d), from 4.16 g of amidine hydrochloride from 10c) and 8.66 g of dimethyl (2-chloro-5-methoxy -phenoxy)malonate there was obtained (2-chloro-5-methoxy-phenoxy) -2-methoxyethyl-4,6(1H, 5H)-pyrimidinedione. MS: 326 (M).

e) According to the procedure of Example 1, part e), the pyrimidine -dione was converted into 4,6-dichloro-5-(2-chloro-5-methoxy-phenoxy) -2-methoxyethyl-pyrimidine. M.p. 66.5°–67.5° C. (from EtOH).

f) From 727 mg of the dichloride from 10e) and 718 mg of (1,3 -benzodioxol-5-sulfonamide) K there was obtained N-[6-chloro-5-(2 -chloro-5-methoxy-phenoxy)-2-(2-methoxy-ethyl)-pyrimidin-4-yl]- 1,3 -benzodioxol-5-sulfonamide. M.p. 154°–155° C. (from MeOH).

g) In analogy to Example 1, part h), the compound from 10f) was converted into N-[5-(2-chloro-5-methoxy-phenoxy)-6-(2-hydroxy -ethoxy)-2-(2-methoxy-ethyl)-pyrimidin-4-yl]- 1,3-benzodioxol-5 -sulfonamide. M.p. 135°–136° C. (from diethyl ether).

Example 11

In analogy to Example 2, from 100 mg of 4-tert-butyl-N-[(2 -chloro-5-methoxy-phenoxy)-6-(2-hydroxy-ethoxy)-pyrimidin-4-yl]-benzenesulfonamide and 122 mg of thiophene-3-carboxylic acid azide there was obtained thiophen-3-ylcarbamic acid 2-[6-(4-tert-butyl -phenylsulfonylamino)-5-(2-chloro-5-methoxy-phenoxy)-pyrimidin-4 -yloxy]-ethyl ester. MS: 633.2 (M+H$^+$).

The thiophene-3-carboxylic acid azide was obtained from thiophene-3-carboxylic acid according to the procedure of Example 2, part e), as a colorless liquid which crystallized in a deep freezer (−18° C.). IR: 2139, 2273 cm$^{-1}$ (N$_3$).

Example 12

In analogy to Example 2, from 100 mg of N-[(2-chloro-5-methoxy -phenoxy)-6-(2-hydroxy-ethoxy)-pyrimidin-4-yl]-1,3-benzodioxol-5 -sulfonamide and 122 mg of thiophene-3-carboxylic acid azide there was obtained thiophen-3-yl-carbamic acid 2-[6-(1,3-benzodioxol-5 -ylsulfonylamino)-5-(2-chloro-5-methoxy-phenoxy)-pyrimidin-4-yloxy]-ethyl ester. MS: 621.2 (M+H$^+$).

Example 13 a) In analogy to Example 2, from 100 mg of N-[5-(2-chloro-5 -methoxy-phenoxy)-6-(2-hydroxy-ethoxy)-2-methylsulfanyl-pyrimidin -4-yl]-1,3-benzodioxol-5-sulfonamide and 82 mg of 2-pyridylcarboxylic acid azide there was obtained pyridine-2-ylcarbamic acid 2-[6-(1,3 -benzodioxol-5-ylsulfonylamino)-5-(2-chloro-5-methoxy-phenoxy)-2 -methylsulfanyl-pyrimidin-4-yloxy]-ethyl ester. White crystals. M.p. 173°–174° C. (from EtOH).

b) A solution of 230 mg of Na methylate in 15 ml of methanol, 1.45 g of dimethyl (2-chloro-5-methoxy-phenoxy)-malonate and 381 mg of thiourea was held at reflux for 5 hours. Then, the solvent was distilled off and the residue was dissolved in 10 ml of H$_2$O. 630 mg of dimethyl sulfate were added to this solution and it was stirred at room temperature for 2 hours. 300 mg of acetic acid were then added, whereby the 5-(2-chloro-5-methoxy-phenoxy)-4,6-dihydroxy-2 -methylsulfanyl-pyrimidine which formed separated. MS: 314 (M).

c) This 4,6-dihydroxypyrimidine was converted into the 4,6-dichloro compound in analogy to Example 1e). M.p. 113°–114° C.

d) In analogy to Example 1, part g), from 500 mg of the dichloro compound and 547 mg of (1,3-benzodioxol-5-sulfonamide) K there was obtained N-[6-chloro-5-(2-chloro- 5-methoxy-phenoxy)-2 -methylsulfanyl-pyrimidin-4-yl]-1,3-benzodioxol-5-sulfonamide. M.p. 110°–112° C. (from EtOH).

e) In analogy to Example 1, part h), from 350 mg of the compound from 13d) and Na glycolate in ethylene glycol there was obtained N-[5 -(2-chloro-5-methoxy-phenoxy)-6-(2-hydroxy-ethoxy)-2 -methylsulfanyl-pyrimidin-4-yl]-1,3-benzodioxol-5-sulfonamide. MS: 542 (M).

Example 14

In analogy to Example 2, from 90 mg of N-[(2-chloro-5-methoxy -phenoxy)-6-(2-hydroxy-ethoxy)-2-methoxymethyl-pyrimidin-4-yl]- 1,3 -benzodioxol-5-sulfonamide and 89 mg of thiophene-3-carboxylic acid azide there was obtained thiophen-3-ylcarbamic acid 2-[6-(1,3 -benzodioxol-5-ylsulfonylamino)-5-(2-chloro-5-methoxy-phenoxy) -2-methoxymethyl-pyrimidin-4-yloxy]-ethyl ester. MS: 665.1 (M+H$^+$).

Example 15 a) In analogy to Example 2, from 150 mg of N-[(2-chloro-5-methoxy -phenoxy)-6-(2-hydroxy-ethoxy)-pyrimidin-4-yl]- 1,3-benzodioxol-5 -sulfonamide and 139 mg of thiophene-2-carboxylic acid azide there was obtained thiophene-2-ylcarbamic acid 2-[6-(1,3-benzodioxol-5 -ylsulfonylamino)-5-(2-chloro-5-methoxy-phenoxy)-pyrimidin-4-yloxy]-ethyl ester. MS: 621.3 (M+H$^+$), m.p. 175° C. (dec.).

b) The thiophene-2-carboxylic acid azide was prepared according to the procedure of Example 2, part e), from thiophene-2-carboxylic acid.

Example 16

In analogy to Example 2, from 125 mg of N-[(2-chloro-5-methoxy -phenoxy)-6-(2-hydroxy-ethoxy)-2-(methoxyethyl)-pyrimidin-4-yl]- 1,3 -benzodioxol-5-sulfonamide and 103 mg of thiophene-3-carboxylic acid azide there was obtained thiophen-3-ylcarbamic acid 2-[6-(1,3 -benzodioxol-5-ylsulfonylamino )-5-(2-chloro-5 -methoxy-phenoxy)-2-(2 -methoxy-ethyl)-pyrimidin-4-yloxy]-ethyl ester. MS: 679.3 (M+H$^+$).

Example 17 a) In analogy to Example 2, from 200 mg of N-[6-(2-hydroxy -ethoxy)-5-(2-methoxy-phenoxy)-2-(4-methoxyphenyl)-pyrimidin-4 -yl]- 1,3-benzodioxol-5-sulfonamide and 195 mg of 2-pyridyl-carboxylic acid azide there was obtained pyridin-2-ylcarbamic acid 2-[6-(1,3 -benzodioxol-5-ylsulfonylamino)-5-(2-methoxy-phenoxy)-2-(4-methoxy -phenyl)-pyrimidin-4-yloxy]-ethyl ester. M.p. 217°–218° C. (from EtOH).

Preparation of the starting material b) In analogy to Example 5, part b), from 4-methoxyphenyl cyanide, methanol and HCl there was obtained 4-methoxyphenyl-methylimido ester hydrochloride. MS: 165 (M).

c) This compound was converted with NH$_3$ into 4-methoxy-phenylamidine hydrochloride. MS: 150 (M).

d) In analogy to Example 1, part d), from 7.63 g of dimethyl (2-methoxy-phenoxy)-malonate and 5.6 g of (4-methoxy-phenyl) -amidine hydrochloride there was obtained 2-(4-methoxyphenyl)-5-(2 -methoxy-phenoxy)-4,6(1H,5H)-pyrimidinedione. MS: 340 (M).

e) In analogy to Example 1, part c), there was obtained 4,6-dichloro -2-(4-methoxy-phenyl)-5-(2-methoxy-phenoxy)-pyrimidine. M.p. 113°– 114° C. (from EtOH).

f) In analogy to Example 1, part g), from 755 mg of the compound from 17e) and 765 mg of (1,3-benzodioxol-5-sulfonamide) K there was obtained N-[6-chloro-5-(2-methoxy-phenoxy)-2-(4-methoxy-phenyl) -pyrimidin-4-yl]- 1,3-benzodioxol-5-sulfonamide. M.p. 187°–188° C. (from EtOH).

g) In analogy to Example 1, part h), from 542 mg of the compound from 17f) and Na glycolate there was obtained N-[6-(2-hydroxy-ethoxy) -5-(2-methoxy-phenoxy)-2-(4-methoxy-phenyl)-pyrimidin-4-yl]- 1,3 -benzodioxol-5-sulfonamide. MS: 567 (M).

Example 18 a) In analogy to Example 2, from 200 mg of N-[6-(2-hydroxy -ethoxy)-5-(2-methoxy-phenoxy)-2-phenyl-pyrimidin-4-yl]-1,3-benzo -dioxol-5-sulfonamide and 165 mg of 2-pyridylcarboxylic acid azide there was obtained pyridin-2-ylcarbamic acid 2-[6-(1,3-benzodioxol-5 -ylsulfonylamino)-5-(2-methoxy-phenoxy)-2-phenyl-pyrimidin-4 -yloxy]-ethyl ester. M.p. 187° C. (from EtOH).

Preparation of the starting material b) In analogy to Example 1, part g), from 1.4 g of 4,6-dichloro-5-(2 -methoxy-phenoxy)-2-phenyl-pyrimidine and 1.9 g of (1,3-benzodioxol -5-sulfonamide) K there was obtained N-[6-chloro-5-(2-methoxy -phenoxy)-2-phenyl-pyrimidin-4-yl ]- 1,3-benzodioxol-5-sulfonamide. M.p. 185°–186° C.

c) In analogy to Example 1, part h), from 1.5 of the compound from 18b) and Na glycolate there was obtained N-[6-(2-hydroxy-ethoxy)-5 -(2-methoxy-phenoxy)-2-phenyl-pyrimidin-4-yl]- 1,3-benzodioxol-5 -sulfonamide. M.p. 159.5°–160° C.

Example 19 a) In analogy to Example 2, from 125 mg of N-[6-(2-hydroxy -ethoxy)-5-(3,5-dimethoxyophenoxy)-pyrimidin-4-yl]- 1,3-benzodioxol-5 -sulfonamide and 75 mg of 2-pyridylcarboxylic acid azide there was obtained pyridin-2-ylcarbamic acid 2-[6-(1,3-benzodioxol-5 -ylsulfonylamino)-5-(3,5-dimethoxy-phenoxy)-pyrimidin-4-yloxy]-ethyl ester. MS: 612.3 (M+H$^+$), m.p. 212° C. (dec.).

Preparation of the starting material b) In analogy to Example 1, part g), from 1.2 g 4,6-dichloro-5-(3,5 -dimethoxy-phenoxy)-pyrimidine and 1.45 g of (1,3-benzodioxol-5 -sulfonamide) K there was obtained N-[6-chloro-5-(3,5-dimethoxy -phenoxy)-pyrimidin-4-yl]- 1,3-benzodioxol-5-sulfonamide. M.p. 167°–168° C.

c) In analogy to Example 1, part h), from 0.31 g of the compound from19b) there was obtained N-[6-(2-hydroxy-ethoxy)-5-(3,5 -dimethoxy-phenoxy)-pyrimidin-4-yl]- 1,3-benzodioxol-5-sulfonamide. M.p. 182° C. (from ethyl acetate).

Example 20 a) In analogy to Example 1, part a), from 0,044 ml of 3-fluorophenyl isocyanate and 100 mg of p-tert-butyl-N-[5-(2-chloro-5-methoxy -phenoxy)-6-(2-hydroxyethoxy)-4-pyrimidinyl]benzenesulfonamide there was obtained 3-fluorophenylcarbamic acid 2-[6-(4-tert -butylphenylsulfonylamino)-5-(2-chloro-5-methoxy-phenoxy) -pyrimidin-4-yloxy]-ethyl ester. MS: 644 (M).

Preparation of the starting materials b) In analogy to Example 1g), from 4 g of 4,6-dichloro-5-(2-chloro-5 -methoxy-phenoxy)pyrimidine from Example 1e) and 7.1 g of (4-tert -butylbenzenesulfonamide) K there was obtained p-tert-butyl-N-[(6 -chloro-5-(2-chloro-5-methoxyphenoxy)-4-pyrimidinyl ]benzene -sulfonamide. M.p. 152°–153 ° C.

c) In analogy to Example 1h), from 2.55 g of the chloride from Example 20b) and 0.85 g of sodium in 30 ml of ethylene glycol there was obtained p-tert-butyl-N-[5-(2-chloro-5-methoxyphenoxy)-6-(2 -hydroxyethoxy)-4-pyrimidinyl]benzenesulfonamide. M.p. 140° C.

Example 21

In analogy to Example 1, part a), from 0.044 ml of 2-fluorophenyl isocyanate and 100 mg of p-tert-butyl-N-[5-(2-chloro-5 -methoxyphenoxy)-6-(2-hydroxyethoxy)-4-pyrimidinyl]benzene -sulfonamide there was obtained 2-fluorophenylcarbamic acid 2-[(6-(4 -tert-butyl-phenylsulfonylamino)-5-(2-chloro-5-methoxy-phenoxy) -pyrimidin-4-yloxy]-ethyl ester. MS: 644 (M).

Example 22

In analogy to Example 1, part a), from 0.042 ml of phenyl isocyanate and 100 mg of p-tert-butyl-N-[5-(2-chloro-5 -methoxyphenoxy)-6-(2-hydroxyethoxy)-4-pyrimidinyl] benzene -sulfonamide there was obtained phenylcarbamic acid 2-[6-(4-tert-butyl -phenylsulfonylamino)-5-(2-chloro-5-methoxy-phenoxy)pyrimidin-4 -yloxyl-ethyl ester. MS: 627.4 (M+H).

Example 23

In analogy to Example 1, part a), from 60 mg of 4-chlorophenyl isocyanate and 100 mg of p-tert-butyl-N-[5-(2-chloro-5 -methoxyphenoxy)-6-(2-hydroxyethoxy)-4-pyrimidinyl]benzene -sulfonamide there was obtained 4-chlorophenylcarbamic acid 2-[6-(4 -tert-butyl-phenylsulfanoylamino)-5-(2-chloro-5-methoxy-phenoxy) -pyrimidin-4-yloxy]-ethyl ester. MS: 661.3 (M+H).

Example 24

In analogy to Example 1, part a), from 50 mg of 3-methoxyphenyl isocyanate and 100 mg of p-tert-butyl-N-[5-(2-chloro-5 -methoxyphenoxy)-6-(2-hydroxyethoxy)-4-pyrimidinyl] benzene -sulfonamide there was obtained 3-methoxy-phenylcarbamic acid 2-[6 -(4-tert-butyl-phenylsulfonylamino )-5-(2-chloro-5-methoxy-phenoxy) -pyrimidin-4-yloxy]-ethyl ester. MS: 657.3 (M+H).

Example 25

In analogy to Example 1, part a), from 0,056 ml of 4-trifluoro -methylphenyl isocyanate and 100 mg of p-tert-butyl-N-[5-(2-chloro-5 -methoxyphenoxy)-6-(2-hydroxyethoxy)-4-pyrimidinyl ]benzene -sulfonamide there was obtained 4-trifluoromethyl-phenylcarbamic acid 2-[ 6-(4-tert-butyl-phenylsulfonylamino )- 5-(2-chloro-5-methoxy -phenoxy)-pyrimidin-4-yloxy]ethyl ester. MS: 695.3 (M+H).

Example 26

In analogy to Example 1, part a), from 69 mg of 2-carbo -methoxyphenyl isocyanate and 100 mg of p-tert-butyl-N-[5-(2-chloro-5 -methoxyphenoxy)-6-(2-hydroxyethoxy)-4-pyrimidinyl]benzene -sulfonamide there was obtained 2-[2-[6-(4-tert-butyl -phenylsulfonylamino)- 5 -(2-chloro- 5 -methoxy)-pyrimidin-4-yloxy] -ethoxycarbonylamino]-benzoic acid methyl ester. MS: 685.3 (M+H).

Example 27

In analogy to Example 1, part a), from 0.05 ml of 3-methylphenyl isocyanate and 100 mg of p-tert-butyl-N-[5-(2-chloro-5-methoxy -phenoxy)-6-(2-hydroxyethoxy)-4-pyrimidinyl]benzenesulfonamide there was obtained 3-tolylcarbamic acid 2-(6-(4-tert-butyl -phenylsulfonylamino)-5-(2-chloro-5-methoxy-phenoxy)-pyrimidin-4 -yloxy]-ethyl ester. MS: 640 (M).

Example 28

In analogy to Example 2, part a), from 58 mg of 2-pyridyl -carboxylic acid azide and 100 mg of p-tert-butyl-N-[5-(2-chloro-5 -methoxyphenoxy)-6-(2-hydroxyethoxy)-4-pyrimidinyl]benzene -sulfonamide there was obtained pyridin-2-ylcarbamic acid 2-[6-(4-tert -butylphenylsulfonylamino)-5-(2-chloro-5-methoxy-phenoxy) -pyrimidin-4-yloxy]-ethyl ester. MS: 628.4 (M+H).

Example 29

In analogy to Example 2, part a), from 59 mg of 2-pyrazine -carboxylic acid azide and 100 mg of p-tert-butyl-N-[5-(2-chloro-5 -methoxyphenoxy)-6-(2-hydroxyethoxy)-4-pyrimidinyl]benzene -sulfonamide there was obtained pyrazin-2-ylcarbamic acid 2-[6-(4-tert -butylphenylsulfonylamino)-5-(2-chloro-5-methoxy-phenoxy) -pyrimidin-4-yloxy]-ethyl ester. MS: 408 (M-$C_5H_4N_3O_3SCl$).

Example 30

In analogy to Example 2, part a), from 58 mg of 3-pyridyl -carboxylic acid azide and 100 mg of p-tert-butyl-N-[5-(2-chloro-5 -methoxyphenoxy)-6-(2-hydroxyethoxy)-4-pyrimidinyl]benzene -sulfonamide there was obtained pyridin-3-ylcarbamic acid 2-[6-(4-tert -butylphenylsulfonylamino)-5-(2-chloro-5-methoxy-phenoxy) -pyrimidin-4-yloxy]-ethyl ester. MS: 628.4 (M+H).

Example 31

In analogy to Example 2, part a), from 58 mg of 4-pyridyl -carboxylic acid azide and 100 mg of p-tert-butyl-N-[5-(2-chloro-5 -methoxyphenoxy)-6-(2-hydroxyethoxy)-4-pyrimidinyl]benzene -sulfonamide there was obtained pyridin-4-ylcarbamic acid 2-[6-(4-tert -butylphenylsulfonylamino)-5-(2-chloro-5-methoxy-phenoxy) -pyrimidin-4-yloxy]-ethyl ester.

Example 32

In analogy to Example 1, part a), from 0.052 ml of 2-methoxy -phenyl isocyanate and 100 mg of p-tert-butyl-N-[5-(2-chloro-5 -methoxyphenoxy)-6-(2-hydroxyethoxy)-

4-pyrimidinyl]benzene -sulfonamide there was obtained 2-methoxy-phenoxycarbamic acid 2-[6 -(4-tert-butylphenylsulfonylamino )-5-(2-chloro-5-methoxy-phenoxy) -pyrimidin-4-yloxy]-ethyl ester. MS: 656 (M).

Example 33

In analogy to Example 2, part a), from 2-acetoxyphenylcarboxylic acid azide and 100 mg of p-tert-butyl-N-[5-(2-chloro-5-methoxy -phenoxy)-6-(2-hydroxyethoxy)-4-pyrimidinyl ]benzenesulfonamide there was obtained acetic acid 2-[2-[(6-tert-butyl-phenylsulfonylamino) -5-(2-chloro-5-methoxy)-pyrimidin-4-yloxy]-ethoxycarbonylamino]-phenyl ester. MS: 642 (M-$C_2H_2O$).

Example 34

90 mg of the compound from Example 33 were dissolved in 5 ml of ethanol, treated with 1 ml of 6N HCl and heated at reflux for 6 hours. The solvent was removed, the crude product was partitioned between ethyl acetate and water. The organic phase was dried, the solvent was removed on a rotary evaporator and the residue was chromatographed on silica gel with $CH_2Cl_2$/ethyl acetate (6:1) as the eluent. There was thus obtained 2-hydroxy-phenylcarbamic acid 2-[6-(4-tert -butylphenylsulfonylamino)-5-(2-chloro-5-methoxy-phenoxy) pyrimidine-4-yloxy]-ethyl ester. MS: 428 (M-$C_7H_5NO_4$SCl).

Example 35

In analogy to Example 1, part a), from 0.048 ml of benzyl isocyanate and 100 mg of p-tert-butyl-N-[5-(2-chloro-5-methoxy -phenoxy)-6-(2-hydroxyethoxy)-4-pyrimidinyl] benzenesulfonamide there was obtained benzylcarbamic acid 2-[6-(4-tert -butylphenylsulfonylamino)-5-(2-chloro-5-methoxy-phenoxy)pyrimidin -4-yloxy]-ethyl ester. MS: 641 (M+H).

Example 36

In analogy to Example 1, part a), from 0.038 ml of Isopropyl isocyanate and 100 mg of p-tert-butyl-N-[5-(2-chloro-5-methoxy -phenoxy)-6-(2-hydroxyethoxy)-4-pyrimidinyl ]benzenesulfonamide there was obtained isopropylcarbamic acid 2-[6-(4-tert-butyl -phenylsulfonylamino)-5-(2-chloro-5-methoxy-phenoxy)-pyrimidin-4 -yloxy]-ethyl ester. MS: 592 (M).

Example 37

In analogy to Example 1, part a), from 0,025 ml of ethyl isocyanate and 75 mg of p-tert-butyl-N-[5-(2-chloro-5-methoxyphenoxy)-6-(2 -hydroxyethoxy)-4-pyrimidinyl] benzenesulfonamide there was obtained ethylcarbamic acid 2-[6-(4-tert-butyl-phenylsulfonylamino)-5-(2 -chloro-5-methoxy-phenoxy)-pyrimidin-4-yloxy]-ethyl ester. MS: 579 (M).

Example 38

100 mg of the compound from Example 28 were dissolved in 15 ml of $CH_2Cl_2$, treated with 60 mg of 3-chloroperbenzoic acid and subsequently heated at reflux for 12 hours. Subsequently, the mixture was poured into water and extracted with $CH_2Cl_2$. The organic phase was dried and subsequently removed on a rotary evaporator. The residue was chromatographed on silica gel with $CH_2Cl_2$/MeOH (20:1) as the eluent. There was thus obtained 1-oxy-pyridin-2-ylcarbamic acid 2 -[ 6-(4-tert-butyl-phenyl-sulfonylamino)-5-(2-chloro-5-methoxy -phenoxy)-pyrimidine-4-yloxy]-ethyl ester. MS: 644.4 (M+H).

Example 39

In analogy to Example 38, from 60 mg of the compound prepared in Example 31 and 33 mg of of 3-chloroperbenzoic acid there was obtained 1 -oxy-pyridin-4-ylcarbamic acid 2-[6-(4-tert-butyl -phenylsulfonylamino)-5-(2-chloro-5-methoxyphenoxy)-pyrimidin-4 -yloxy]-ethyl ester. MS: 644.5 (M+H).

Example 40

By alkylating the compound from Example 1, part a), with methyl iodide there was obtained 3-[2-[5-(2-chloro-5-methoxy-phenoxy)-6 -(2,3-dihydro- 1,4-benzodioxin-6-ylsulfonylamino)-pyrimidin-4-yloxy]-ethoxycarbonylamino]-1 -methyl-pyridinium iodide.

Example 41

By deprotonizing the compound in Example 40 with sodium methylate as the base there was obtained N-[5-(2-chloro-5-methoxy -phenoxy)-6-[2-(1-methyl-pyridin-3-yliocarbamoyloxy)-ethoxy]-pyrimidin-4-yl ] - 1,3 -benzodioxol-5 -sulfonamide.

Example 42

In analogy to Example 1, part a), from 0.05 ml of phenyl isocyanate and 100 mg of p-tert-butyl-No[6-(2-hydroxyethoxy)-5-(m-methoxy -phenoxy)-4-pyrimidinyl]benzenesulfonamide (see EP-A-526708) there was obtained phenylcarbamic acid 2-[6-(4-tert-butyl -phenylsulfonylamino)-5-(3-methoxy-phenoxy)-pyrimidin-4-yloxy]-ethyl ester. MS: 593.4 (M+H).

Example 43

In analogy to Example 2, part a), from 62 mg of 2-pyridyl -carboxylic acid azide and 100 mg of p-tert-butyl-N-[6-(2 -hydroxyethoxy)-5-(m-methoxyphenoxy)-4-pyrimidinyl] -benzenesulfonamide there was obtained pyridin-2-ylcarbamic acid 2-[6 -(4-tert-butyl-phenylsulfonylamino)-5-(3-methoxy-phenoxy)-pyrimidin -4-yloxy]-ethyl ester. MS: 594.5 (M+H).

Example 44

In analogy to Example 2, part a), from 62 mg of 4-pyridyl -carboxylic acid azide and 100 mg of p-tert-butyl-N-[6-(2 -hydroxyethoxy)-5-(m-methoxyphenoxy)-4-pyrimidinyl]-benzenesulfonamide there was obtained pyridin-4-ylcarbamic acid 2-[6 -(4-tert-butyl-phenylsulfonylamino)-5 -(3 -methoxy-phenoxy)-pyrimidin -4-yloxy]-ethyl ester. MS: 594.5 (M+H).

Example 45

In analogy to Example 2, part a), from 84 mg of quinaldic acid azide and 100 mg of p-tert-butyl-N-[6-(2-hydroxyethoxy)-5-(m -methoxyphenoxy)-4-pyrimidinyl]benzenesulfonamide there was obtained quinolin-2-ylcarbamic acid 2-[6-(4-tert-butyl -phenylsulfonylamino)-5-(3-methoxyphenoxy)-pyrimidin-4-yloxy]-ethyl ester. MS: 644.3 (M+H).

Example 46

In analogy to Example 1, part a), from 0,062 ml of (R)-1-phenylethyl isocyanate and 100 mg of p-tert-butyl-N-[6-(2-hydroxyethoxy)-5-(m-methoxyphenoxy)-4-pyrimidinyl]-benzenesulfonamide there was obtained (R)-1-phenylethylcarbamic acid 2-[ 6-(4-tert-butyl-phenylsulfonylamino )-5-(3-methoxy-phenoxy) -pyrimidin-4-yloxy]-ethyl ester. MS: 621 (M+H).

Example 47

In analogy to Example 1, part a), from 0.05 ml of cyclohexyl isocyanate and 100 mg of p-tert-butyl-No[6-(2-hydroxyethoxy)-5-(m -methoxyphenoxy)-4-pyrimidinyl]benzenesulfonamide there was obtained cyclohexylcarbamic acid 2-[6-(4-tert-butyl -phenylsulfonylamino)-5-(3-methoxy-phenoxy)-pyrimidin-4-yloxy]-ethyl ester. MS: 599.4 (M+H).

Example 48

In analogy to Example 1, part a), from 0.24 ml of ethyl isocyanatoacetate and 500 mg of p-tert-butyl-N-[6-(2-hydroxyethoxy) -5-(m-methoxyphenoxy)-4-pyrimidinyl]benzenesulfonamide there was obtained [2-[6-(4-tert-butyl-phenylsulfonylamino)-5-(3-methoxy -phenoxy)-pyrimidin-4-yloxy]-ethoxycarbonylamino]-acetic acid ethyl ester. MS: 603.5 (M+H).

Example 49

410 mg of [2-[6-(4-tert-butyl-phenylsulfonylamino)-5-(3-methoxy-phenoxy)-pyrimidin-4-yloxy] -ethoxycarbonylamino]-acetic acid ethyl ester in 20 ml of ethanol were treated with 1.36 ml of 1N NaOH and the reaction solution was heated at 60° C. for 2 hours. Subsequently, the mixture was treated with 1.36 ml of 1N HCl and concentrated on a rotary evaporator. The residue was chromatographed on silica gel with $CH_2Cl_2$/MeOH (10:1) as the eluent. There were thus obtained 300 mg of 2-[6-(4-tert-butyl-phenylsulfonylamino)-5-(3 -methoxy-phenoxy)-pyrimidin-4-yloxy] -ethoxycarbonylamino-acetic acid. MS: 573.3 (M–H).

Example 50

100 mg of [2-[6-(4-tert-butyl-phenylsulfonylamino)-5-(3-methoxy-phenoxy)-pyrimidin-4-yloxy]-ethoxycarbonylamino]-acetic acid ethyl ester were dissolved in 3 ml of ethanol, treated with 3 ml of THF and 36 mg of $CaCl_2$ and then 25 mg of $NaBH_4$ were added at room temperature. The mixture was stirred at room temperature for 2 hours, concentrated on a rotary evaporator and the residue was distributed between dilute citric acid and ethyl acetate. The organic phase was dried, the solvent was removed and the residue was chromatographed on silica gel with $CH_2Cl_2$ (20:1) as the eluent. There were thus obtained 78 mg of 2-hydroxy-ethylcarbamic acid 2-[6-(4-tert-butyl -phenylsulfonylamino)-5-(3-methoxy-phenoxy)-pyrimidin-4-yloxy]-ethyl ester. MS: 561 (M+H).

Example 51

In analogy to Example 1, part a), from 0.15 ml of morpholine-4 -carbonyl chloride and 200 mg of p-tert-butyl-N-[6-(2-hydroxy-ethoxy) -5-(m-methoxyphenoxy)-4-pyrimidinyl]benzenesulfonamide with the addition of 154 mg of dimethylaminopyridine at a reaction period of 12 hours there was obtained morpholine-4-carboxylic acid 2-[6-(4-tert -butyl-phenylsulfonylamino)-5-(3-methoxy-phenoxy)-pyrimidin-4 -yloxy]-ethyl ester. MS: 587.4 (M+H).

Example 52

100 mg of 2-[6-(4-tert-butyl-phenylsulfonylamino)-5-(3-methoxy-phenoxy)-pyrimidin-4-yloxy]-ethoxycarbonylamino-acetic acid in 15 ml of $CH_2Cl_2$ were treated with 0.015 ml of morpholine, 22 mg of dimethylaminopyridine, 33 mg of N-ethyl-N'-(3-dimethylaminopropyl) -carbodiimide hydrochloride and the solution was stirred at room temperature overnight. Subsequently, it was concentrated on a rotary evaporator, the residue was partitioned between ethyl acetate and $H_2O$. After drying the organic phase the solvent was removed on a rotary evaporator and the residue was chromatographed on silica gel with $CH_2Cl_2$/MeOH (40:1) as the eluent. There were thus obtained 80 mg of 2-morpholin-4-yl-2-oxo-ethylcarbamic acid 2-[6-(4-tert-butyl -phenylsulfonylamino)-5-(3-methoxy-phenoxy)-pyrimidine-4-yloxy]-ethyl ester. MS: 644.5 (M+H).

Example 53

In analogy to Example 52, from 100 mg of 2-[6-(4-tert-butyl -phenylsulfonylamino)-5-(3-methoxy-phenoxy)-pyrimidin-4-yloxy]-ethoxycarbonylamino-acetic acid and 0.014 ml of pyrrolidine there was obtained 2-oxo-2-pyrrolidin-1-yl-ethylcarbamic acid 2-[6-(4-tert-butyl -phenylsulfonylamino)-5-(3-methoxy-phenoxy)-pyrimidin-4-yloxy]-ethyl ester. MS: 628.5 (M+H).

Example 54

In analogy to Example 52, from 100 mg of 2-[6-(4-tert-butyl -phenylsulfonylamino)-5-(3-methoxy-phenoxy)-pyrimidin-4-yloxy]-ethoxycarbonylamino-acetic acid and 0.016 ml of aniline there was obtained phenylcarbamoylmethylcarbamic acid 2-[6-(4-tert-butyl -phenylsulfonylamino)-5-(3-methoxy-phenoxy)-pyrimidin-4-yloxy]-ethyl ester. MS: 650.5 (M+H).

Example 55

In analogy to Example 1, part a), from 100 mg of p-tert-butyl-N -[ 6-(2-hydroxyethoxy)-5-(m-methoxyphenoxy)-4-pyrimidinyl]benzene -sulfonamide and 78 mg of ethyl 2-isocyanato-4-methyl-valerate there was obtained 2-[2-[6-(4-tert-butyl-phenylsulfonylamino)-5-(3 -methoxyphenoxy)-pyrimidin-4-yloxy]-ethoxycarbonylamino]-4 -methyl-pentanoic acid ethyl ester. MS: 659 (M+H).

Example 56

By alkylating pyridin-4-ylcarbamic acid 2-[6-(4-tert-butylphenyl -sulfonylamino)- 5 -(2-chloro-5 -methoxy-phenoxy)-pyrimidin-4 -yloxy]ethyl ester with methyl iodide there was obtained 4-[2-[6-(4-tert -butyl-phenylsulfonylamino)-5-(2-chloro-5-methoxy-phenoxy -pyrimidin-4-yloxy]-ethoxycarbonylamino]- 1-methyl-pyridinium iodide.

Example 57

Analogously to Example 2, part a), from 3-furyl isocyanate and N -[ 5-(2-chloro-5-methoxy-phenoxy)-6-(2-hydroxy-ethoxy)-pyrimidin-4 -yl]-1,3-benzodioxol-5-sulfonamide there was obtained furan-3 -ylcarbamic acid 2-[6-(1, 3-benzodioxol-5-ylsulfonylamino)-5-(2-chloro -5-methoxy-phenoxy)-pyrimidin-4-yloxy]-ethyl ester.

Example 58

In analogy to Example 2, part a), from 2-pyridylcarboxylic acid azide and 4-tert-butyl-N-[6-(2-hydroxyethoxy)-2-isopropyl-5-(2-methoxy-phenoxy)-pyrimidin-4-yl]-benzenesulfonamide (see EP-A -526708) there was obtained pyridin-2-ylcarbamic acid 2-[6-(4-tert-butyl-phenylsulfonylamino)-2-isopropyl-5-(2-methoxy-phenoxy)-pyrimidin-4-yloxy]-ethyl ester. M.p. 119°–120° C.

Example 59

In analogy to Example 2, part a), from 4-pyridylcarboxylic acid azide and the starting compound of Example 58 there was obtained pyridin-4-ylcarbamic acid 2-[6-(4-tert-butyl-phenylsulfonylamino)-2-isopropyl-5-(2-methoxy-phenoxy)-pyrimidin-4-yloxy]-ethyl ester.

Example 60

In analogy to Example 2, part a), from 2-pyridylcarboxylic acid azide and p-tert-butyl-N-[6-(2-hydroxyethoxy)-5-(o-methoxy-phenoxy)-2-propyl-4-pyrimidinyl]benzenesulfonamide (see EP-A-526708) there was obtained pyridin-2-ylcarbamic acid 2-[6-(4-tert-butyl-phenylsulfonylamino)-5-(2-methoxy-phenoxy)-2-propyl-pyrimidin-4-yloxy]-ethyl ester. M.p. 147°–149° C.

Example 61

In analogy to Example 2, part a), from 4-pyridylcarboxylic acid azide and the starting compound of Example 60 there was obtained pyridin-4-ylcarbamic acid 2-[6-(4-tert-butyl-phenylsulfonylamino)-5-(2-methoxy-phenoxy)-2-propyl-pyrimidin-4-yloxy]-ethyl ester.

Example 62

In analogy to Example 2, part a), from 2-pyridylcarboxylic acid azide and p-tert-butyl-N-[2-tert-butyl-6-(2-hydroxyethoxy)-5-(o-methoxyphenoxy)-4-pyrimidinyl]benzenesulfonamide (see. EP-A -526708) there was obtained pyridin-2-ylcarbamic acid 2-[2-tert-butyl -6-(4-tert-butyl-phenylsulfonylamino)-5-(2-methoxy-phenoxy)-pyrimidin-4-yloxy]-ethyl ester.

Example 63

In analogy to Example 2, part a), from 4-pyridylcarboxylic acid azide and the starting compound of Example 62 there was obtained pyridin-4-ylcarbamic acid 2-[2-tert-butyl-6-(4-tert-butylphenyl sulfonylamino )-5-(2-methoxy-phenoxy)-pyrimidin-4-yloxy]-ethyl ester.

Example 64

In analogy to Example 2, part a), from 2-pyridylcarboxylic acid azide and 4-tert-butyl-N-[2-cyclopropyl-6-(2-hydroxy-ethoxy)-5-(2-methoxy-phenoxy)-pyrimidin-4-yl]benzenesulfonamide (see EP-A -526708) there was obtained pyridin-2-ylcarbamic acid 2-[6-(4-tert-butyl-phenylsulfonylamino)-2-cyclopropyl-5-(2-methoxy-phenoxy)-pyrimidin-4-yloxy]-ethyl ester.

Example 65

In analogy to Example 2, part a) from 4-pyridylcarboxylic acid azide and the starting compound of Example 64 there was obtained pyridin-4-ylcarbamic acid 2-[6-(4-tert-butyl-phenylsulfonylamino)-2-cyclopropyl-5-(2-methoxy-phenoxy)-pyrimidin-4-yloxy]-ethyl ester.

Example 66

In analogy to Example 2, part a), from 2-pyridylcarboxylic acid azide and 4-tert-butyl-N-[6-(2-hydroxy-ethoxy)-5-(2-methoxy-phenoxy)-2-(thiophen-2-yl)-pyrimidin-4-yl]benzenesulfonamide (see EP-A-526708) there was obtained pyridin-2-ylcarbamic acid 2-[6-(4-tert-butyl-phenylsulfonylamino)-5-(2-methoxy-phenoxy)-2-thiophen-2-yl-pyrimidin-4-yloxy]-ethyl ester. M.p. 175°–180° C.

Example 67

In analogy to Example 2, part a), from 4-pyridylcarboxylic acid azide and the starting compound of Example 66 there was obtained pyrimidin-4-ylcarbamic acid 2-[6-(4-tert-butyl-phenylsulfonylamino)-5-(2-methoxy-phenoxy)-2-thiophen-2-yl-pyrimidin-4-yloxy]-ethyl ester. M.p. 188°–192° C.

Example 68

In analogy to Example 2, part a), from 2-pyridylcarboxylic acid azide and p-tert-butyl-N-[6-(2-hydroxyethoxy)-5-(o-methoxy-phenoxy)-2-methyl-4-pyrimidinyl]benzenesulfonamide (see EP-A -526708) there was obtained pyridin-2-ylcarbamic acid 2-[6-(4-tert-butyl-phenylsulfonylamino)-5-(2-methoxy-phenoxy)-2-methyl-pyrimidin-4-yloxy]-ethyl ester. M.p. 169°–170° C.

Example 69

In analogy to Example 2, part a), from 4-pyridylcarboxylic acid azide and the starting compound of Example 68 there was obtained pyridin-4-ylcarbamic acid 2-[6-(4-tert-butyl-phenylsulfonylamino)-5-(2-methoxy-phenoxy)-2-methyl-pyrimidin-4-yloxy]-ethyl ester. M.p. 155°–158° C.

Example 70 a) In analogy to Example 2, part a), from 2-pyridylcarboxylic acid azide and 4-tert-butyl-N-[6-(2-hydroxyethoxy)-5-(2-methoxy-phenoxy)-2,2'-bipyrimidin-4-yl]-benzenesulfonamide (see EP-A -526708) there was obtained pyridin-2-ylcarbamic acid 2-[6-(4-tert-butyl-phenylsulfonylamino)-5-(2-methoxy-phenoxy)-2,2'-bipyrimidin-4-yloxy]-ethyl ester. M.p. 203°–204° C.

Preparation of the sodium salt b) 414 mg of the above compound were dissolved in dioxane. The solution was subsequently treated with the stoichiometric amount of sodium methylate in 2 ml of methanol, whereby the corresponding sodium salt separated. The salt was subsequently filtered off under suction and carefully dried at 60° C.

Calc. C 57.14 H 4.65 N 14.13 S 4.62

Found C 56.85 H 4.85 N 13.94 S 4.60

Preparation of the hydrochloride c) 414 mg of the compound prepared in Example 70a) were dissolved in absolute dioxane and treated with an excess of hydrogen chloride in absolute dioxane. An amorphous precipitate formed and this was filtered off under suction and dried to constant weight at 30° C. in a water-jet vacuum.

Example 71

In analogy to Example 2, part a), from 4-pyridylcarboxylic acid azide and the starting compound of Example 70, part a), there was obtained pyridin-4-ylcarbamic acid 2-[6-(4-tert-butyl -phenylsulfonylamino)-5-(2-methoxy-phenoxy)-2,2'-bipyrimidin-4 -yloxy]-ethyl ester. M.p. 138°–141° C.

Example 72 a) In analogy to Example 2, part a), from 2-pyridinecarboxylic acid azide and 4-tert-butyl-N-[6-(2-hydroxy-ethoxy)-5-(2-methoxy -phenoxy)-2-(morpholin-4-yl)-pyrimidin-4-yl]-benzenesulfonamide there was obtained pyridin-2-ylcarbamic acid 2-[6-(2-tert-butyl -phenylsulfonylamino)-5-(2-methoxyphenoxy)-2-morpholin-4-yl -pyrimidin-4-yloxy]-ethyl ester. MS: 679.3 (M+H); IR: 1735 (KBr, carbamate).

Preparation of the starting material b) In analogy to Example 1, part d), from dimethyl (2-methoxy -phenoxy)-malonate (EP-A-526708) and morpholino-formamidine there was prepared 5-(2-methoxy-phenoxy)-2-(morpholin-4-yl)-4,6(1H,5H) -pyrimidinedione. Therefrom with POCl$_3$ there was obtained 4,6 -dichloro-5-(2-methoxy-phenoxy)-2-(morpholin-4-yl)pyrimidine, therefrom with (4-tert-butylbenzenesulfonamide) K there was obtained [ 4-tert-butyl-N-[ 6-chloro-5-(2-methoxyphenoxy)-2-(morpholin-4-yl) -pyrimidin-4-yl]-benzenesulfonamide] and finally with Na ethylene glycolate there was obtained 4-tert-butyl-N-[6-(2-hydroxy-ethoxy)-5 -(2-methoxy-phenoxy)-2-(morpholin-4-yl)-benzenesulfonamide.

Example 73

In analogy to Example 2, part a), from 4-pyridylcarboxylic acid azide and 4-tert-butyl-N-[6-(2-hydroxy-ethoxy)-5-(2-methoxy -phenoxy)-2-(morpholin-4-yl-pyrimidin-4-yl ]-benzenesulfonamide there was obtained pyridin-4-ylcarbamic acid 2-[6-(2-tert-butyl -phenylsulfonylamino)-5-(2-methoxy-phenoxy)-2-morpholin-4-yl -pyrimidin-4-yloxy]-ethyl ester. MS: 679.5 (M+H); IR: 1739 (KBr, carbamate).

Example 74

In analogy to Example 2, part a), from 3-pyridylcarboxylic acid azide and 4-tert-butyl-N-[6-(2-hydroxy-ethoxy)-5-(2-methoxy -phenoxy)-2-(morpholin-4-yl-pyrimidin-4-yl]-benzenesulfonamide there was obtained pyridin-3-ylcarbamic acid 2-[6-(2-tert-butyl -phenylsulfonylamino)-5-(2-methoxy-phenoxy)-2-morpholin-4-yl -pyrimidin-4-yloxy]-ethyl ester. MS: 679.7 (M+H); IR: 1735 (KBr, carbamate).

Example 75

In analogy to Example 2, part a), from 2-furancarboxylic acid azide and 4-tert-butyl-N-[6-(2-hydroxy-ethoxy)-5-(2-methoxy-phenoxy)-2 -(morpholin-4-yl-pyrimidin-4-yl]-benzenesulfonamide there was obtained furan-2-ylcarbamic acid 2-[6-(4-tert-butyl -phenylsulfonylamino )-5-(2-methoxy-phenoxy)-2-morpholin-4-yl -pyrimidin-4-yloxy]-ethyl ester. MS: 668.2 (M+H); IR: 1718 (KBr, carbamate).

Example 76

In analogy to Example 2, part a), from 3-methylisoxazol-5-yl -carboxylic acid azide and 4-tert-butyl-N-[6-(2-hydroxy-ethoxy)-5-(2 -methoxy-phenoxy)-2-(morpholin-4-yl-pyrimidinyl-4-yl]-benzenesulfonamide there was obtained 3-methyl-isoxazol-5-yl -carbamic acid 2-[6-(4-tert-butyl-phenylsulfonylamino)-5-(2-methoxy -phenoxy)-2-morpholin-4-yl-pyrimidin-4-yloxy]-ethyl ester. M.p. 103°–107° C.

The carboxylic acid azide used was obtained from 3-methyl-isoxazol-5-yl-carboxylic acid (Tetrahedron Letters, 327, 1967) and NaN3 in analogy to Example 2, part e).

Example 77 a) In analogy to Example 2, part a), from 2-pyridylcarboxylic acid azide and 4-cyclopropyl-N-[6-(2-hydroxy-ethoxy)-5-(2-methoxy -phenoxy)-2,2'-bipyrimidin-4-yl]-benzenesulfonamide there was obtained pyridin-2-yl-carbamic acid 2-[6-(4-cyclopropyl -phenylsulfonylamino)-5-(2-methoxy-phenoxy)-2,2'-bipyrimidin-4 -yloxy]-ethyl ester. MS: 656 (M+H); IR: 1732 (carbamate).

Preparation of the starting material:

b) 4-cyclopropylaniline (Bull. Soc. Chim. Belg. 1975, 84, 1197) was diazotized and converted with SO$_2$/Cu$_2$Cl$_2$ (3 hours, room temperature) into the corresponding 4-cyclopropylbenzenesulfonyl chloride. Subsequent aminolysis with ammonium hydroxide yielded the corresponding 4-cyclopropylbenzenesulfonamide, m.p. 158°–168° C., which was finally converted with KOH in EtOH in to the potassium salt.

From (4-cyclopropylbenzenesulfonamide) K and 4,6-dichloro-5-(2 -methoxy-phenoxy)-2,2'-bipyrimidine (see EP-A-526708) [there was obtained] 4-cyclopropyl-N-[6-chloro-5-(2-methoxy-phenoxy)-2 -(pyrimidin-2-yl)-pyrimidin-4-yl]-benzenesulfonamide which was finally reacted with sodium ethylene glycolate.

Example 78 a) In analogy to Example 2, part a), from 2-pyridylcarbonyl azide and 4-methylsulfanyl-N-[ 6-(2-hydroxy-ethoxy)-5 -(2-methoxy-phenoxy) -2,2'-bipyrimidin-4-yl]-benzenesulfonamide there was obtained pyridin-2-ylcarbamic acid 2-[5-(2-methoxy-phenoxy)-6-(4-methylsulsulfanyl -phenylsulfonylamino)-2,2'-bipyrimidin-4-yloxy]-ethyl ester. M.p. 175°–178° C.

Preparation of the starting material:

b) In analogy to Example 1, part g), from (p-methylthiobenzene -sulfonamide) K and 4,6-dichloro-5-(2-methoxy-phenoxy)-2,2'-bipyrimidine there was obtained 4-methylsulfanyl-N-[6-chloro-5-(2 -methoxy-phenoxy)-2-(pyrimidin-2-yl)-pyrimidin-4-yl]-benzene -sulfonamide and therefrom with sodium ethylene glycolate there was obtained 4-methylsulfonyl-N-[6-(2-hydroxy-ethoxy)-5-(2-methoxy -phenoxy)-2,2'-bipyrimidin-4-yl]-benzenesulfonamide. M.p. 194°–195° C.

Example 79

In analogy to Example 2, part a), from 4-methylsulfanyl-N-[6-(2 -hydroxy-ethoxy)-5-(2-methoxy-phenoxy)-2-(pyrimidin-2-yl) -pyrimidin-4-yl]-benzenesulfonamide and 3-methyl-isoxazol-5-yl -carboxylic acid azide there was obtained 3-methyl-isoxazol-5-ylcarbamic acid 2-[5-(2- methoxy-phenoxy)-6-(4-methylsulfanyl -phenylsulfonylamino)-2,2'-bipyrimidin-4-yloxy-ethyl ester. M.p. 187°–189° C.

Example 80 a) In analogy to Example 2, part a), from 2-pyridylcarboxylic acid azide and 4-vinyl-N-[6-(2-hydroxy-ethoxy)-5-(2-methoxy-phenoxy) -2,2'-bipyrimidin-4-yl]-benzenesulfonamide there was obtained pyridin -2-ylcarbamic acid 2-[5-(2-methoxy-phenoxy)-6-(4-vinyl -phenylsulfonylamino)-2,2'-bipyrimidin-4-yloxy]-ethyl ester. M.p. 166°–173° C.

The starting compound was prepared by converting (p-vinyl -benzenesulfonamide) K and 4,6-dichloro-5-(2-methoxy-phenoxy)-2,2'-bipyrimidine into 4-vinyl-N-[6-chloro-5-(2-methoxy-phenoxy-2 -pyrimidin-2-yl)-pyrimidin-4-yl]-benzenesulfonamide and reacting this compound with sodium ethylene glycolate. M.p. 182°–184° C.

Example 81 a) In analogy to Example 2, part a), from 4-tert-butyl-N-[6-(2 -hydroxyethoxy)- 5 -(2-chloro-5-methoxybenzyl)-2-(morpholin-4-yl) -pyrimidin-4-yl]-benzenesulfonamide and 3-methyl-isoxazol-5-yl -carboxylic acid azide there was obtained 3-methyl-isoxazol-5-ylcarbamic acid 2-[6-(4-tert-butyl-phenylsulfonylamino)-5-(2-chloro-5-methoxy -benzyl)-2-morpholin-4-yl-pyrimidin-4-yloxy]-ethyl ester. MS: 715.5 (M).

The starting material was synthesized as follows:

b) 4-Chloro-m-cresol was methylated with dimethyl sulfate to give 1 -chloro-4-methoxy-2-methylbenzene. This was converted with N -bromosuccinimide into 2-bromomethyl- 1-chloro-4-methoxybenzene. Subsequent alkylation with diethyl malonate yielded diethyl (2-chloro -5-methoxybenzyl)-malonate. This was condensed with morpholine -formamidine in analogy to Example 1, part d), to give 5-(2-chloro-5 -methoxy-benzyl)-2-(morpholin-4-yl)-4, 6(1H,5H)-pyrimidinedione. Subsequent chlorination with POCl$_3$ analogously to Example 1e) gave 4,6 -dichloro-5-(2-chloro-5-methoxy-benzyl)-2-(morpholin-4-yl)-pyrimidine which was reacted further with (4-tert.butylbenzenesulfonamide) K analogously to Example 1 g) to give 4-tert-butyl-N-[6-chloro-5-(2-chloro -5 -methoxy-benzyl)-2-(morpholin-4-yl)-pyrimidin-4 -yl]benzenesulfonamide. Subsequent reaction with sodium ethylene glycolate analogously to Example 1h) finally gave 4-tert-butyl-N-[6-(2 -hydroxyethoxy)-5-(2-chloro-5-methoxybenzyl)-2-(morpholine-4 -yl)pyrimidin-4-yl]-benzenesulfonamide. M.p. 159°–162° C.

Example 82

0.1 g of 4-tert-butyl-N-[6-(2-hydroxy-ethoxy)-5-(2 -methoxyphenyl-sulfanyl)-pyrimidin-4-yl]-benzenesulfonamide and 0.1 g of 2-pyridylcarboxylic acid azide in 20 ml of toluene were stirred at 110° C. for 3 hours and concentrated. The residue was partitioned between water and chloroform, the organic phase was dried and concentrated. The residue was purifed over silica gel with chloroform and recrystallized from chloroform-ether. There was obtained 0.09 g of pyridin-2-ylcarbamic acid 2-[6-(4-tert-butyl-phenylsulfonylamino)-5 -(2-methoxy-phenylsulfanyl)-pyrimidine-4-yloxy)-ethyl ester. M.p. 193 ° C., MS: 609.

The starting material was prepared as follows:

a) 0.86 g of formamidine acetate and 2 g of dimethyl (2-methoxy -phenylsulfanyl)-malonate (J. Org. Chem. 55, 33–38 [1990]) were added to a sodium methylate solution from 40 ml of MeOH and 0.54 g of sodium. The reaction mixture was stirred at 80° C. for 4 hours and concentrated. The residue was partitioned between toluene and water and the aqueous phase was adjusted to pH 3. The precipitate was filtered off under suction, washed with ether and dried. There was obtained 0.4 g of 6 -hydroxy-5-(2-methoxy-phenylsulfanyl)-3,4-dihydro-pyrimidin-4-one. M.p. 291 ° C.

b) 0.35 g of 6-hydroxy-5-(2-methoxy-phenylsulfanyl)-3, 4-dihydro -pyrimidin-4-one in 10 ml of dioxane was treated with 0.7 ml of Hünig base and 0.65 ml of POCl$_3$. The orange reaction mixture was stirred at 80° C. for 20 hours, thereafter the excess reagent and dioxane were distilled off. The residue was taken up in dichloromethane and washed with water, saturated NaHCO$_3$ and water. The organic phase was dried, concentrated and the residue was purified over silica gel with dichloromethane. There was obtained 0.27 g of 4,6-dichloro-5-(2 -methoxy-phenylsulfanyl)-pyrimidine. M.p. 103° C.

c) 0.24 g of 4,6-dichloro-5-(2-methoxy-phenylsulfanyl)-pyrimidine and 0.415 g of (p-t-butyl-sulfonamide) potassium in 5 ml of dry dimethyl sulfoxide were heated to 120° C. under argon for 1 hour. Thereafter, the reation mixture was treated with 50 ml of water and adjusted to pH 1. The precipitate was filtered off under suction, washed with water and partitioned between ethyl acetate and water. The organic phase was dried, the solvent was evaporated and the residue was purified over silica gel with dichloromethane and chloroform. There was obtained 0.26 g of 4-tert-butyl-N-[6-chloro-5-(2-methoxy -phenylsulfanyl)-pyrimidin-4-yl]-benzenesulfonamide- M.p. 186° C.

d) 0.1 g of 4-tert-butyl-N-[6-chloro-5-(2-methoxy-phenylsulfanyl) -pyrimidin-4-yl]-benzenesulfonamide was added to a sodium glycolate solution from 0,015 g of sodium and 0,326 g of ethylene glycol. The reaction mixture was stirred at 60° C. under argon for 2 hours and partitioned between 1N hydrochloric acid and ethyl acetate. The organic phase was washed with water, dried over sodium sulfate and the solvent was distilled off. The residue was chromatographed over silica gel with chloroform. There was obtained 0,077 g of 4-tert-butyl-N-[6-(2 -hydroxy-ethoxy)-5-(2-methoxy-phenylsulfanyl)-pyrimidin-4-yl ] -benzenesulfonamide as a foam. MS: 489 (M).

Example 83

In analogy to Example 82, from 4-tert-butyl-N-[6-(2-hydroxy -ethoxy)-5 -(2-methoxy-phenylsulfanyl)- 2,2'-bipyrimidin-4- yl ] -benzenesulfonamide there was obtained pyridin-3-ylcarbamic acid 2-[6 -tert-butyl-phenylsulfonylamino)-5-(2-methoxy-phenylsulfanyl)-2,2'-bipyrimidin-4-yloxy]-ethyl ester. M.p. 115° C.

The starting material was prepared as follows:

a) In analogy to Example 82, part a), from dimethyl (2-methoxy -phenylsulfanyl)-malonate and 2-amidinpyrimidine there was obtained 6-hydroxy-5-(2-methoxy-phenylsulfanyl)-3,4-dihydro-2,2'-bipyrimidin-4-one as an oil which was reacted with POCl$_3$ in analogy to Example 82, part b). There was obtained 4,6-dichloro-5-(2-methoxy -phenylsulfanyl)-2,2'-dipyrimidine which was reacted in analogy to Example 82, part c), with (p-t-butyl-benzenesulfonamide) potassium. There was obtained 4-tert-butyl-N-[6-chloro-5-(2-methoxy -phenylsulfanyl)-2,2'-bipyrimidin-4-yl]-benzenesulfonamide which was converted with sodium glycolate in analogy to Example 82, part d), into 4-tert-butyl-N-[6-(2-hydroxy-ethoxy)-5-(2-methoxy-phenylsulfanyl) -2,2'-bipyrimidin-4-yl ]-benzenesulfonamide.

Example 84 a) In analogy to Example 82, from 4-tert-butyl-N-[6-(2-hydroxy -ethoxy)-5-(2-methoxy-phenylsulfanyl)-2-methyl-pyrimidin-4-yl]-benzenesulfonamide and 2-pyridylcarboxylic acid azide there was obtained pyridin-4-ylcarbamic acid 2-[6-(4-tert-butyl -phenylsulfonylamino)-5-(2-methoxy-phenylsulfanyl)-2-methyl -pyrimidin-4-yloxy]-ethyl ester. M.p. 157° C.

b) The sulfonamide used above was synthesized according to the synthesis sequence of Example 82a)-d), with formamidine acetate in part a) being replaced by acetamidine hydrochloride.

Example 85 a) In analogy to Example 2, part a), from p-tert-butyl-N-[5-(2-bromo -5-methoxyphenoxy)-6-(2-hydroxy-ethoxy)-4-pyrimidinyl] -benzene -sulfonamide and 2-pyridylcarboxylic acid azide there was obtained pyridyl-2-ylcarbamic acid 2-[5-(2-bromo-5-methoxy-phenoxy)-6-(4 -tert-butyl-phenylsulfonylamino)-pyrimidin-4-yloxy]-ethyl ester.

Preparation of the starting material:

b) By brominating 4,6-dichloro-5-(3-methoxyphenoxy)-pyrimidine with N-bromosuccinimide in acetic acid/acetic anhydride at 100° C. there was obtained 4,6-dichloro-5-(2-bromo-5-methoxyphenoxy)pyrimidine; therefrom with p-tert-benzenesulfonamide K there was obtained N-[5 -(2-bromo-5-methoxyphenoxy)-6-chloropyrimidin-4-yl]-4-tert-butyl -benzenesulfonamide and therefrom with Na ethylene glycolate there was obtained p-tert-butyl-N-[5-(2-bromo-5-methoxyphenoxy)-6-(2 -hydroxyethoxy)-4-pyrimidinyl]-benzenesulfonamide.

Example 86 a) In analogy to Example 2, part a), from p-tert-butyl-N-[5-(3,4 -dimethoxy-phenoxy)-6-(2-hydroxyethoxy)-4-pyrimidinyl ]benzenesulfonamide there was obtained pyridin-4-ylcarbamic acid 2-[6 -(4-tert-butyl-phenylsulfonylamino)-5 -(3,4-dimethoxy-phenoxy)pyrimidin- 4-yloxy]-ethyl ester.

Preparation of the starting material:

b) By condensing 2-(3,4-dimethoxy-phenoxy)-propane-1, 3-dione acid with formamidine acetate there was obtained 5-(3,4-dimethoxyphenoxy)-pyrimidine- 4,6-diol, therefrom with $POCl_3$ there was obtained 4,6-dichloro-5-(3,4-dimethoxy-phenoxy)-pyrimidine, therefrom with p-tert-butylbenzenesulfonamide K there was obtained 4-tert-butyl-N-[6 -chloro-5-(3,4-dimethoxy-phenoxy)-pyrimidin-4-yl]-benzenesulfonamide and therefrom with Na ethylene glycolate there was obtained p-tert-butyl-N-[5-(3,4-dimethoxy-phenoxy)-6-(2-hydroxyethoxy)-4-pyrimidinyl]-benzenesulfonamide.

Example 87

In analogy to Example 2, part a), from 2-pyridylcarboxylic acid azide and 4-tert-butyl-N-[5-(3,4-dimethoxyphenoxy)-6-(2 -hydroxyethoxy)-4-pyrimidinyl]-benzenesulfonamide there was obtained pyridin-2-ylcarbamic acid 2-[6-(4-tert-butyl-phenylsulfonylamino)-5 -(3,4-dimethoxy-phenoxy)-pyrimidin-4-yloxy]-ethyl ester. MS: 624.2 (M+H).

Example 88 a) In analogy to Example 2, part a), from 2-pyridylcarboxylic acid azide and 3,4-dimethoxy-N-[5-(2-chloro-5-methoxyphenoxy)-6-(2 -hydroxy-ethoxy)-4-pyrimidinyl]-benzenesulfonamide there was obtained pyridin-2-ylcarbamic acid 2-[5-(2-chloro-5-methoxyphenoxy)- 6-(3,4-dimethoxy-phenylsulfonylamino)-pyrimidin-4-yloxy]-ethyl ester. MS: 632.5 (M+H).

b) The starting material was obtained starting from the compound from Example 1e) analogously to the process of Example 1g) and 1h) using (3,4-dimethoxybenzenesulfonamide) K as the component. MS: 412 (M-$SO_2$Cl).

Example 89 a) In analogy to Example 1, part a), from phenyl isocyanate and acetic acid 2-[4-[6-(2-hydroxy-ethoxy)-5-(2-methoxy-phenoxy)-pyrimidin-4 -ylaminosulfonyl]-phenoxy]-ethyl ester there was obtained acetic acid 2 -4-[5-(2-methoxy-phenoxy)-6-(2-phenylcarbamoyloxy-ethoxy)-pyrimidin- 4-ylsulfamoyl]-phenoxy]-ethyl ester. MS: 639.4 (M+H).

Preparation of the starting material:

b) 9 g of 2-phenoxy-ethyl acetate were dissolved in 75 ml of methylene chloride and the solution was subsequently added dropwise to 11 ml of ice-cold chlorosulfonic acid. The mixture was left to react at room temperature for 1 hour, partitioned between ice-water and $CH_2Cl_2$, the organic phase was dried and the solvent was finally removed on a rotary evaporator. The residue was crystallized from ethyl acetate-hexane. There were thus obtained 4.3 g of 2-(4-chlorosulfonylphenoxy)ethyl acetate.

c) A solution of 0.783 g of 6-[2-(t-butyl-dimethylsilyloxy) ethoxy]-5 -(2-methoxy-phenoxy)pyrimidin-4-ylamine (described in EP 526708) in 30 ml of tetrahydrofuran was treated with 0.436 g of NaH (60%) and stirred at room temperature for 1 hour. Thereafter, 0.7 g of 2-(4 -chlorosulfonylphenoxy)-ethyl acetate was added. The reaction mixture was stirred at room temperature for 3.5 hours, poured on to ice, extracted with ethyl acetate and the organic phase was dried. After as removing the solvent and chromatography on silica gel with $CH_2Cl_2$/ethyl acetate (10:1) there were obtained 460 mg of the still silyl-protected product as a white foam. This was treated slowly in 20 ml of acetonitrile at 0° C. with 3 ml of 40% HF. The reaction mixture was stirred at 0° C. for 30 minutes and at room temperature for 90 minutes, then poured into ice/2N $KHCO_3$ solution, extracted $CH_2Cl_2$ and the organic phase was dried. After removing the solvent the residue was chromatographed on silica gel with $CH_2Cl_2$/MeOH (30:1) as the eluent. There were thus obtained 319 mg of the desired product. MS: 520 (M+H).

Example 90

In analogy to Example 2, part a), from 2-pyridylcarboxylic acid azide and acetic acid 2-[4-[6-(2-hydroxyethoxy)-5-(2-methoxyphenoxy)pyrimidin- 4-ylaminosulfonyl]phenoxy]-ethyl ester there was obtained acetic acid 2-[4-5-(2-methoxy-phenoxy)-6-(2-pyridin-2-ylcarbamoyloxy-ethoxy)-pyrimidin- 4-ylsulfamoyl]-phenoxy]-ethyl ester. MS: 640.5 (M+H).

Example 91

In analogy to Example 2, part a), from 4-pyridylcarboxylic acid azide and acetic acid 2-[4-[6-(2-hydroxyethoxy)-5-(2-methoxyphenoxy)pyrimidin- 4-ylaminosulfonyl]phenoxy]ethyl ester there was obtained acetic acid 2-[4-5-(2-methoxy-phenoxy)-6-(2-pyridin-4 -ylcarbamoyloxy-ethoxy)-pyrimidin-4-ylsulfamoyl]-phenoxy]-ethyl ester. MS: 640.5 (M+H).

Example 92

In analogy to Example 2, part a), from 3-pyridylcarboxylic acid azide and acetic acid 2-[4-[6-(2-hydroxyethoxy)-5-(2-methoxyphenoxy)pyrimidin- 4-ylaminosulfonyl]phenoxy]-ethyl ester there was obtained acetic acid 2-[4-[5-(2-methoxy-phenoxy)-6-(2-pyridin-4 -ylcarbamoyloxy-ethoxy)-pyrimidin-4-ylsulfamoyl]-phenoxy]-ethyl ester. MS: 640.4 (M+H).

Example 93

In analogy to Example 1, part a), from 2-fluorophenyl isocyanate and acetic acid 2-[4-[6-(2-hydroxyethoxy)-5-(2-methoxyphenoxy)pyrimidin- 4-ylaminosulfonyl]phenoxy]-ethyl ester there was obtained acetic acid 2-[4-[6-[2-(2-fluoro-phenylcarbamoyloxy)-ethoxy]-5-(2 -methoxy-phenoxy)-pyrimidin-4-ylsulfamoyl]-phenoxy]-ethyl ester. MS: 657.4 (M+H).

Example 94

By basic saponification of the compound of Example 89 there was obtained phenylcarbamic acid 2-[6-[4-(2-hydroxy-ethoxy)-phenylsulfonylamino]-5-(2-methoxy-phenoxy)-pyrimidin-4-yloxy]-ethyl ester. MS: 597.3 (M+H).

Example 95

By basic saponification of the compound prepared in Example 90 there was obtained pyridin-2-ylcarbamic acid 2-[6-[4-(2-hydroxy-ethoxy)-phenylsulfonylamino]-5-(2-methoxy-phenoxy)-pyrimidin-4-yloxy]-ethyl ester. MS: 598.6 (M+H).

Example 96

By basic saponification of the compound prepared in Example 91 there was obtained pyridin-4-ylcarbamic acid 2-[6-[4-(2-hydroxy-ethoxy)-phenylsulfonylamino]-5-(2-methoxy-phenoxy)-pyrimidin-4-yloxy]-ethyl ester. MS: 596.6 (M–H).

Example 97

By basic saponification of the compound prepared in Example 92 there was obtained pyridin-3-ylcarbamic acid 2-[6-[4-(2-hydroxy-ethoxy)-phenylsulfonylamino]-5-(2-methoxy-phenoxy)-pyrimidin-4-yloxy]-ethyl ester. MS: 598.4 (M+H).

Example 98

By basic saponification of the compound prepared in Example 93 there was obtained 2-fluoro-phenylcarbamic acid 2-[6-[4-(2-hydroxy-ethoxy)-phenylsulfonylamino]-5-(2-methoxy-phenoxy)-pyrimidin-4-yloxy]-ethyl ester. MS: 615.4 (M+H).

Example 99

In analogy to Example 1, part a), from N-[6-(2-hydroxyethoxy)-5 -(2-methoxy-phenoxy)-pyrimidin-4-yl]-4-methoxy-3-(2-morpholin-4-yl- 2-oxo-ethoxy)-benzenesulfonamide and 2-fluoro isocyanate there was obtained 2-fluorophenylcarbamic acid 2-[6-[4-methoxy-3-(2 -morpholin-4-yl-2-oxo-ethoxy)-phenylsulfonylamino]-5-(2-methoxy-phenoxy)-pyrimidin- 4-yloxy]-ethyl ester. MS: 728.5 (M+H).

For the preparation of the starting material, 2-(2-methoxyphenoxy)- 1-(morpholin-4-yl)-ethane was reacted with chlorosulfonic acid to give 4-methoxy-3-(2-morpholin-4-yl-2-oxo-ethoxy)-benzenesulfonyl chloride and this was reacted with the amine from Example 89c) in an analogous manner. MS: 591 (M+H).

Example 100

In analogy to Example 2, part a), from 2-pyridylcarboxylic acid azide and N-[6-(2-hydroxy-ethoxy)-5-(2-methoxyphenoxy)-pyrimidin- 4-yl]-4-methoxy-3-(2-morpholin-4-yl-2-oxo-ethoxy)-benzenesulfonamide there was obtained pyridin-2-ylcarbamic acid 2-[6-[4-methoxy-3 -[2-morpholin-4-yl-2-oxo-ethoxy)-phenylsulfonylamino]-5-(2-methoxy-phenoxy)-pyrimidin- 4-yloxy]-ethyl ester. MS: 709.2 (M–H).

Example 101

In analogy to Example 2, part a), from 4-pyridylcarboxylic acid azide and N-[6-(2-hydroxy-ethoxy)-5-(2-methoxyphenoxy)-pyrimidin- 4-yl]-4-methoxy-3-(2-morpholin-4-yl-2-oxo-ethoxy)-benzenesulfonamide there was obtained pyridin-4-ylcarbamic acid 2-[6-[4-methoxy-3 -2-morpholin-4-yl-2-oxo-ethoxy)-phenylsulfonylamino]-5-(2-methoxy-phenoxy)-pyrimidin- 4-yloxy]-ethyl ester. MS: 711.4 (M+H).

Example 102

In analogy to Example 2, pan a), from pyrazinecarboxylic acid azide and N-[6-(2-hydroxy-ethoxy)-5-(2-methoxy-phenoxy)-pyrimidin- 4-yl]-4-methoxy-3-(2-morpholin-4-yl-2-oxo-ethoxy)-benzenesulfonamide there was obtained pyrazin-2-ylcarbamic acid 2-[6-[4-methoxy- 3-[2-morpholin-4-yl-2-oxo-ethoxy)-phenylsulfonylamino]-5-(2 -methoxy-phenoxy)-pyrimidin-4-yloxy]-ethyl ester. MS: 712.5 (M+H).

Example 103 a) In analogy to Example 1, part a), from 2-fluoro-isocyanate and acetic acid 2-[4-[5-(2-chloro-5-methoxy-phenoxy)-6-(2-hydroxy-ethoxy)-pyrimidin- 4-ylaminosulfonyl]-phenoxy]-ethyl ester there was obtained acetic acid 2-[4-[5-(2-chloro-5-methoxy-phenoxy)-6-[2-(2 -fluoro-phenylcarbamoyloxy)-ethoxy]-pyrimidin-4-ylsulfamoyl]-phenoxy]-ethyl ester. MS: 691.6 (M+H).

Preparation of the starting materials b) The compound used above, MS: 554.3 (M+H), was prepared in analogy to Example 89, part c), from 6-[2-(tert-butyl-dimethyl-silanyloxy)-ethoxy]-5-(2-chloro-5-methoxy-phenoxy)-pyrimidine-4 -ylamine and the sulfonyl chloride from Example 89, part b).

c) About 500 ml of $NH_3$ were conducted into a solution of 9.9 g of 4,6-dichloro-5-(2-chloro-5-methoxy-phenoxy)-pyrimidine from Example 1e) in 400 ml of ethanol at −78°

C. Thereafter, the reaction mixture was stirred at −78° C. for 15 hours and at room temperature for 50 hours and finally evaporated. The residue was partitioned between ethyl acetate and water and the organic phase was worked-up. There were thus obtained 8.53 g of 6-chloro-5-(2-chloro-5-methoxy-phenoxy)-pyrimidin- 4-ylamine as yellow crystals. MS: 285 (M).

d) 8.53 g of the previously obtained compound were added to a solution of 0.82 g of sodium in 100 ml of ethylene glycol at 50° C. The solution was heated to 100° C. for 20 hours, thereafter partitioned between semi-saturated NH$_4$Cl solution and CH$_2$Cl$_2$ and worked-up. There were obtained 8.3 g of 2-[6-amino-5-(2-chloro-5-methoxy-phenoxy)-4-pyrimidin-4-yloxy]-1-ethanol as a white solid which was silylated without additional purification. For this purpose, the above material (8.3 g) was dissolved in 300 ml of methylene chloride, treated with 8.15 g of dimethylaminopyridine and finally at room temperature with 10.05 g of t-butyldimethylchlorosilane. The reaction solution was stirred at room temperature for 5 hours. It was then filtered, the solution was evaporated, the evaporation residue was partitioned between semi-saturated NH$_4$Cl solution and ethyl acetate and the organic phase was worked-up. Subsequent crystallization from methylene chloride/hexane yielded 6-[2-(tert-butyl-dimethyl-silanyloxy)-ethoxy]- 5-(2-chloro-5-methoxy-phenoxy)-pyrimidine-4-ylamine. MS: 410 (M−CH$_3$).

Example 104

By basic saponification of the compound prepared in Example 103a) there was obtained 2-fluoro-phenylcarbamic acid 2-[5-(2-chloro- 5-methoxy-phenoxy)-6-[4-(2-hydroxy-ethoxy)-phenylsulfonylamino]-pyrimidin-4-yloxy]-ethyl ester.

Example 105

In analogy to Example 2, part a), from acetic acid 2-[4-[5-(2 -chloro-5-methoxy-phenoxy)-6-(2-hydroxy-ethoxy)-pyrimidin-4 -ylaminosulfonyl]-phenoxy]-ethyl ester and 2-pyridylcarboxylic acid azide there was obtained acetic acid 2-[4-[5-(2-chloro-5-methoxy-phenoxy)- 6-(2-pyridin-2-ylcarbamoyloxy-ethoxy)-pyrimidin-4 -ylsulfamoyl]-phenoxy]-ethyl ester. MS: 674.5 (M+H).

Example 106

By basic saponification of the compound prepared in Example 105 there was obtained pyridin-2-ylcarbamic acid 2-[5-(2-chloro-5 -methoxy-phenoxy)-6-[4-(2-hydroxy-ethoxy)-phenylsulfonylamino]--pyrimidin-4-yloxy]-ethyl ester. MS: 632.4 (M+H).

Example 107 a) In analogy to Example 1, part a), from N-[5-(2-chloro-5-methoxy-phenoxy)- 6-(2-hydroxy-ethoxy)-pyrimidin-4-yl]-4-methoxy-3-(2 -morpholin-4-yl-2-oxo-ethoxy)-benzenesulfonamide and 2-fluoro-isocyanate there was obtained 2-fluoro-phenylcarbamic acid 2-[5-(2 -chloro-5-methoxy-phenoxy)-6-[4-methoxy-3-(2-morpholin-4-yl-2-oxo-ethoxy)-phenylsulfonylamino]-pyrimidin-4-yloxy]-ethyl ester. MS: 762.5 (M+H).

Preparation of the starting materials b) The starting compound used above, MS: 525 (M−SO$_2$Cl), was prepared in analogy to Example 89, part c), from the sulfonyl chloride of Example 99 and 6-[2-(tert-butyl-dimethyl-silanyloxy)-ethoxy]-5-(2 -chloro-5-methoxy-phenoxy)-pyrimidin-4-ylamine.

Example 108

In analogy to Example 2, part a), from N-[5-(2-chloro-5-methoxy-phenoxy)- 6-(2-hydroxy-ethoxy)-pyrimidin-4-yl]-4-methoxy-3-(2 -morpholin-4-yl-2-oxo-ethoxy)-benzenesulfonamide and 2 -pyridylcarboxylic acid azide there was obtained pyridin-2-ylcarbamic acid 2-[5-(2-chloro-5-methoxy-phenoxy)-6-[4-methoxy-3-(2 -morpholin-4-yl-2-oxo-ethoxy)-phenylsulfonylamino]-pyrimidin-4 -yloxy]-ethyl ester. MS: 745.5 (M+H).

Example 109

In analogy to Example 2, part a), from N-[5-(2-chloro-5-methoxy-phenoxy)- 6-(2-hydroxy-ethoxy)-pyrimidin-4-yl]-4-methoxy-3-(2 -morpholin-4-yl-2-oxo-ethoxy)-benzenesulfonamide and 4 -pyridylcarboxylic acid azide there was obtained pyridin-4-ylcarbamic acid 2-[5-(2-chloro-5-methoxy-phenoxy)-6-[4-methoxy-3-(2 -morpholin-4-yl-2-oxo-ethoxy)-phenylsulfonylamino]-pyrimidin-4 -yloxy]-ethyl ester. MS: 745.6 (M+H).

Example 110

In analogy to Example 2, part a), from N-[5-(2-chloro-5-methoxy-phenoxy)- 6-(2-hydroxy-ethoxy)-pyrimidin-4-yl]-4-methoxy-3-(2 -morpholin-4-yl-2-oxo-ethoxy)-benzenesulfonamide and pyrazinecarboxylic acid azide there was obtained pyrazin-2-ylcarbamic acid 2-[5-(2-chloro-5-methoxy-phenoxy)-6-[4-methoxy-3-(2 -morpholin-4-yl-2-oxo-ethoxy)-phenylsulfonylamino]-pyrimidin-4 -yloxy]-ethyl ester. MS: 746.4 (M+H).

Example 111 a) In analogy to Example 1, part a), from phenyl isocyanate and N-[6 -(2-hydroxy-ethoxy)-5-(3-methoxy-phenoxy)-pyrimidin-4-yl]-4 -methoxy-3-(2-morpholin-4-yl-2-oxo-ethoxy)-benzenesulfonamide there was obtained phenylcarbamic acid 2-[6-[4-methoxy-3-(2-morpholin-4-yl-2-oxo-ethoxy)-phenylsulfonylamino]-5-(3-methoxy-phenoxy)-pyrimidin- 4-yloxy]-ethyl ester. MS: 710.5 (M+H).

Preparation of the starting materials b) The compound used above was obtained in analogy to Example 89, part c), from the sulfonyl chloride of Example 99 and 6-[2-(tert-butyl-dimethyl-silanyloxy)-ethoxy]-5-(3-methoxy-phenoxy)-pyrimidin-4 -ylamine.

c) The amine used in b) was obtained from 4,6-dichloro-5-(3 -methoxy-phenoxy)-pyrimidine (described in EP 526708) according to Example 103, part c) and d).

Example 112 a) In analogy to Example 1, pan a), from 2-fluoro-isocyanate and 5 -[N-[5-(2-chloro-5-methoxy-phenoxy)-6-(2-hydroxy-ethoxy)-pyrimidin- 4-yl]aminosulfonyl]-2-methoxy-phenoxyacetic acid ethyl ester there was obtained [5-[5-(2-chloro-5-methoxy-phenoxy)-6-[2-(2 -fluorophenylcarbamoyloxy)-ethoxy]-pyrimidin-4-ylsulfamoyl]-2 -methoxy-phenoxyl-acetic acid ethyl ester. MS: 621 (M−SO$_2$Cl).

Preparation of the starting materials b) The starting material used above, MS: 484 (M–SO$_2$Cl), was obtained in analogy to Example 89, part c), from 6-[2-(tert-butyl-dimethyl-silanyloxy)-ethoxy]-5-(2-chloro-5-methoxy-phenoxy)-pyrimidin-4 -ylamine and (2-methoxy-5-chlorosulfonyl)phenoxyacetic acid ethyl ester (preparation described in EP 526708).

Example 113

By basic saponification of the compound prepared in Example 112a) there was obtained 5-[5-(2-chloro-5-methoxy-phenoxy)-6-[2-(2 -fluoro-phenylcarbamoyloxy)-ethoxy]-pyrimidin-4-ylsulfamoyl]-2 -methoxy-phenoxy]-acetic acid. MS: 693.4 (M+H).

Example 114 a) In analogy to Example 2, part a), from 2-pyridylcarboxylic acid azide and N-[5-(2-chloro-5-methoxy-phenoxy)-6-(2-hydroxy-ethoxy)-pyrimidin- 4-yl]-4-(2-morpholin-4-yl-2-oxo-ethoxy)-benzenesulfonamide there was obtained pyridin-2-ylcarbamic acid 2-[5 -(2-chloro-5-methoxy-phenoxy)-6-[4-(2-morpholin-4-yl-2-oxo-ethoxy]-phenylsulfonylamino]-pyrimidin-4-yloxy]-ethyl ester. MS: 715.3 (M+H).

Preparation of the starting materials b) The compound used above, MS: 495 (M–SO$_2$Cl), was obtained in analogy to Example 89, part c), from 6-[2-(tert-butyl-dimethyl-silanyloxy)-ethoxy]-5-(2-chloro-5-methoxy-phenoxy)-pyrimidin-4 -ylamine and 4-(2-morpholin-4-yl-2-oxo-ethoxy)-benzenesulfonyl chloride.

c) The sulfonyl chloride used above was obtained analogously to Example 89, part b), from 4-(phenoxyacetyl)-morpholine and chlorosulfonic acid.

Example 115

In analogy to Example 2, part a), from N-[5-(2-chloro-5-methoxy-phenoxy)- 6-(2-hydroxy-ethoxy)-pyrimidin-4-yl]-4-(2-morpholin-4-yl- 2-oxo-ethoxy)-benzenesulfonamide and pyrazinecarboxylic acid azide there was obtained pyrazin-2-ylcarbamic acid 2-[5-(2-chloro-5 -methoxy-phenoxy)-6-[4-(2-morpholin-4-yl-2-oxo-ethoxy]-phenylsulfonylamino]-pyrimidin-4-yloxy]-ethyl ester. MS: 716.4 (M+H).

Example 116 a) In analogy to Example 2, part a), from 2-pyridylcarboxylic acid azide and N-[6-(2-hydroxy-ethoxy)-5-(2-methoxy-phenoxy)-pyrimidin- 4-yl]-4-(2-morpholin-4-yl-2-oxo-ethoxy)-benzenesulfonamide there was obtained pyridin-2-ylcarbamic acid 2-[5-(2-methoxy-phenoxy)-6 -[4-(2-morpholin-4-yl-2-oxo-ethoxy)-phenylsulfonylamino]-pyrimidin-4 -yloxy]-ethyl ester. MS: 681.3 (M+H).

Preparation of the starting material b) The above starting material was prepared in analogy to Example 89, part c), using the compound from Example 114 as the sulfonyl chloride.

Example 117

In analogy to Example 2, part a), from 4-pyridylcarboxylic acid azide and N-[6-(2-hydroxy-ethoxy)-5-(2-methoxy-phenoxy)-pyrimidin- 4-yl]-4-(2-morpholin-4-yl-2-oxo-ethoxy)-benzenesulfonamide there was obtained pyridin-4-ylcarbamic acid 2-[5-(2-methoxy-phenoxy)-6 -[4-(2-morpholin-4-yl-2-oxo-ethoxy)-phenylsulfonylamino]-pyrimidin-4 -yloxy]-ethyl ester. MS: 681.5 (M+H).

Example 118 a) In analogy to Example 2, part a), from 2-pyridylcarboxylic acid azide and N-[6-(2-hydroxy-ethoxy)-5-(2-methoxy-phenoxy)-pyrimidin- 4-yl]-4-(3-morpholin-4-yl-3-oxo-propyl)-benzenesulfonamide there was obtained pyridin-2-ylcarbamic acid 2-[5-(2-methoxy-phenoxy)-6-[4-(3 -morpholin-4-yl-3-oxo-propyl)-phenylsulfonylamino]-pyrimidin-4 -yloxyl-ethyl ester. MS: 679.4 (M+H).

Preparation of the starting materials b) The above starting material, MS: 558 (M), was obtained in analogy to Example 89, part c), using 4-(3-morpholin-4-yl-3-oxo-propyl)-benzenesulfonyl chloride as the sulfonyl chloride.

c) The foregoing sulfochloride, MS: 317 (M+H), was obtained according to Example 89, part b), from 4-(1-oxo-3-phenylpropyl)-morpholine and chlorosulfonic acid.

Example 119 a) In analogy to Example 2, part a), from 2-pyridylcarboxylic acid azide and N-[5-(2-chloro-5-methoxy-phenoxy)-6-(2-hydroxy-ethoxy)-pyrimidin- 4-yl]-4-(3-morpholin-4-yl-3-oxo-propyl)-benzenesulfonamide there was obtained pyridin-2-ylcarbamic acid 2-[5 -(2-chloro-5-methoxy-phenoxy)-6-[4-(3 -morpholin-4-yl-3 -oxo-propyl)-phenylsulfonylamino]-pyrimidin-4-yloxy]-ethyl ester. MS: 713.6 (M+H).

Preparation of the starting material b) The above starting material, MS: 557 (M-Cl), was obtained in analogy to Example 89, part c), from 6-[2-(tert-butyl-dimethyl-silanyloxy)-ethoxy]-5-(2-chloro-5-methoxy-phenoxy)-pyrimidin-4 -ylamine and the sulfochloride of Example 118.

Example 120 a) In analogy to Example 2, part a), from 2-pyridylcarboxylic acid azide and N-[6-(2-hydroxy-ethoxy)-5-(2-methoxy-phenoxy)-pyrimidin- 4-yl]-4-methoxy-3-(3-morpholin-4-yl-3-oxo-propyl)-benzenesulfonamide there was obtained pyridin-2-ylcarbamic acid 2-[6-[4-methoxy-3 -(3-morpholin-4-yl-3-oxo-propyl)-phenylsulfonylamino]-5-(2-methoxy-phenoxy)-pyrimidin- 4-yloxy]-ethyl ester. MS: 709.5 (M+H).

Preparation of the starting materials b) The foregoing compound, MS: 524 (M–SO$_2$), was obtained in analogy to Example 89, part c), using 4-methoxy-3-(3-morpholin-4-yl-3 -oxo-propyl)-benzenesulfonyl chloride as the starting material.

c) The above sulfochloride was prepared analogously to Example 89b) from 3-(2-methoxy-phenyl)-1-morpholin-4-ylpropanone and chlorosulfonic acid.

Example 121 a) In analogy to Example 2, part a), from 2-pyridylcarboxylic acid azide and N-[5-(2-chloro-5-methoxy-phenoxy)-6-(2-hydroxy-ethoxy)-pyrimidin- 4-yl]-4-methoxy-3-(3-morpholin-4-yl-3-oxo-propyl)-benzenesulfonamide there was obtained pyridin-2-ylcarbamic acid 2-[5 -(2-chloro-5-methoxy-phenoxy)-6-[4-methoxy-3-(3 -morpholin-4-yl-3 -oxo-propyl)-phenylsulfonylamino]-pyrimidin-4-yloxy]-ethyl ester. MS: 743.4 (M+H).

b) The foregoing compound, MS: 623,6 (M+H), was obtained in analogy to Example 89, part c), from 6-[2-(tert-butyl-dimethyl-silanyloxy)-ethoxy]-5-(2-chloro-5-methoxy-phenoxy)-pyrimidin-4-ylamine and the sulfochloride of Example 120b).

Example 122

In analogy to Example 2, part a), from N-[5-(2-chloro-5-methoxy-phenoxy)-6-(2-hydroxy-ethoxy)-pyrimidin-4-yl]-4-methoxy-3-(3-morpholin-4-yl-3-oxo-propyl)-benzenesulfonamide and pyrazinecarboxylic acid azide there was obtained pyrimidin-2-ylcarbamic acid 2-[5-(2-chloro-5-methoxy-phenoxy)-6-[4-methoxy-3-(3-morpholin-4-yl-3-oxo-propyl)-phenylsulfonylamino]-pyrimidin-4-yloxy]-ethyl ester. MS: 744.5 (M+H).

Example 123 a) In analogy to Example 2, part a), from 2-pyridylcarboxylic acid azide and N-[6-(2-hydroxy-ethoxy)-5-(2-methoxy-phenoxy)-pyrimidin-4-yl]-4-methoxy-3-(3-oxo-3-piperidin-1-yl-propyl)-benzenesulfonamide there was obtained pyridin-2-ylcarbamic acid 2-[5-(4-methoxy-phenoxy)-6-[4-methoxy-3-(3-piperidin-1-yl-3-oxo-propyl)-phenylsulfonylamino]-pyrimidin-4-yloxy]-ethyl ester. MS: 707.5 (M+H).

Preparation of the starting materials b) The above starting material was obtained in analogy to Example 89, part c), using 4-methoxy-3-(3-oxo-3-piperidin-1-yl-propyl)-benzenesulfonyl chloride as the reaction component.

c) The foregoing sulfochloride, MS: 345 (M), was synthesized according to Example 89b) from 3-(2-methoxy-phenyl)-1-piperidin-1-yl-propanone and chlorosulfonic acid.

Example 124 a) In analogy to Example 2, part a), from 2-pyridylcarboxylic acid azide and N-[6-[2-hydroxy-ethoxy)-5-(2-methoxy-phenoxy)-2,2'-bipyrimidin-4-yl]-4-methoxy-3-(3-piperidin-1-yl-3-oxo-propyl)-benzenesulfonamide there was obtained pyridin-2-ylcarbamic acid 2-[5-(2-methoxy-phenoxy)-6-[4-methoxy-3-(3-piperidin-1-yl-3-oxo-propyl)-phenylsulfonylamino]-2,2'-bipyrimidin-4-yloxy]-ethyl ester. MS: 785.5 (M+H).

Preparation of the starting materials b) The compound used above, MS: 665.5 (M+H), was obtained in analogy to Example 89, part c), from the sulfochloride of Example 123b) and 6-[2-(tert-butyl-dimethyl-silanyloxy)-ethoxy]-5-(2-methoxy-phenoxy)-2,2'-bipyrimidin-4-ylamine.

c) The above starting material, MS: 454 (M–CH₃), was obtained from 4,6-dichloro-5-(2-methoxy-phenoxy)-2,2'-bipyrimidine according to Example 103, part c) and d).

Example 125 a) In analogy to Example 1, part a), from 2-fluoro-isocyanate and N-[6-(2-hydroxy-ethoxy)-5-(2-methoxy-phenoxy)-pyrimidin-4-yl]-4-methoxy-3-(2-oxo-2-piperidin-1-yl-ethoxy)-benzenesulfonamide there was obtained 2-fluoro-phenylcarbamic acid 2-[6-[4-methoxy-3-(2-oxo-2-piperidin-1-yl-ethoxy)-phenylsulfonylamino]-5-(2-methoxy-phenoxy)-pyrimidin-4-yloxy]-ethyl ester. MS: 726.6 (M+H).

Preparation of the starting materials b) The above starting material, MS: 524 (M–SO₂), was obtained in analogy to Example 89, part c), using 4-methoxy-3-(2-oxo-2-piperidin-1-yl-ethoxy)-benzenesulfonyl chloride as the reaction component.

c) The foregoing sulfochloride was synthesized according to Example 89b) from 2-(2-methoxy-phenoxy)-1-piperidin-1-yl-ethanone.

Example 126 a) In analogy to Example 2, part a), from 2-pyridylcarboxylic acid azide and N-[6-(2-hydroxy-ethoxy)-5-(2-methoxy-phenoxy)-pyrimidin-4-yl]-4-methoxy-2-(3-morpholin-4-yl-3-oxo-propyl)-benzenesulfonamide there was obtained pyridin-2-ylcarbamic acid 2-[6-[4-methoxy-2-(3-morpholin-4-yl-3-oxo-propyl)-phenylsulfonylamino]-5-(2-methoxy-phenoxy)-pyrimidin-4-yloxy]-ethyl ester. MS: 709,4 (M+H).

Preparation of the starting materials b) The above starting material, MS: 524 (M–SO₂), was obtained in analogy to Example 89, part c), using 4-methoxy-2-(3-morpholin-4-yl-3-oxo-propyl)-benzenesulfonamide as the reaction component.

c) The foregoing sulfochloride was synthesized analogously to Example 89b) from 3-(3-methoxy-phenyl)-1-morpholin-4-yl-propanone and chlorosulfonic acid.

Example 127 a) In analogy to Example 2, part a), from 2-pyridylcarboxylic acid azide and 4-(2-bromo-ethoxy)-N-[6-(2-hydroxyethoxy)-5-(2-methoxy-phenoxy)-4-pyrimidinyl]-benzenesulfonamide there was obtained pyridin-2-ylcarbamic acid 2-[6-[4-(2-bromo-ethoxy)-phenylsulfonylamino]-5-(2-methoxy-phenoxy)-pyrimidin-4-yloxy]-ethyl ester. MS: 660.3 (M+H).

Preparation of the starting material b) The above starting material, MS: 475 (M–SO₂), was obtained according to Example 89, part c), using 4-(2-bromo-ethoxy)-benzenesulfonyl chloride as the reaction component.

Example 128 a) In analogy to Example 2, part a), from 2-pyridylcarboxylic acid azide and acetic acid 3-[4-[6-(2-hydroxy-ethoxy)-5-(2-methoxy-phenoxy)-pyrimidin-4-ylsulfamoyl]-phenoxy]-propyl ester there was obtained acetic acid 3-[4-[5-(2-methoxy-phenoxy)-6-(2-pyridin-2-ylcarbamoyloxy-ethoxy)-pyrimidin-4-ylsulfamoyl]-phenoxy]-propyl ester. MS: 654.5 (M+H).

Preparation of the starting materials b) The compound used above, MS: 534,3 (M+H), was obtained according to Example 89, part c), using acetic acid 3-(4-chlorosulfonylphenoxy)-propyl ester as the sulfonyl chloride.

c) The foregoing sulfochloride was obtained analogously to Example 89b) from 3-phenoxy-1-propanol acetate and chlorosulfonic acid.

Example 129

By alkaline saponification of the compound prepared in Example 128a) there was obtained pyridin-2-ylcarbamic acid 2-[6-[4-(3-hydroxy-propoxy)-phenylsulfonylamino]-5-(2-methoxy-phenoxy)-pyrimidin-4-yloxy]-ethyl ester. MS: 612,4 (M+H).

Example 130 a) In analogy to Example 2, part a), from N-[6-(2-hydroxy-ethoxy)-5-(2-methoxy-phenoxy)-pyrimidin-4-yl]-4-methoxy-3-(2-morpholin-4-yl-2-oxo-ethyl)-benzene-sulfonamide and 2-pyridylcarboxylic acid azide there was obtained pyridin-2-ylcarbamic acid 2-[6-[4-methoxy-3-(2-morpholin-4-yl-2-oxo-ethyl)-phenylsulfonylamino]-5-(2-methoxy-phenoxy)-pyrimidin-4-yloxy]-ethyl ester. MS: 695.6 (M+H).

Preparation of the starting materials b) The above compound, MS: 510 (M–SO$_2$), was obtained in analogy to Example 89, part c), from 4-methoxy-3-(2-morpholin-4-yl-2-oxo-ethyl)-benzenesulfonyl chloride.

c) The sulfochloride was obtained analogously to Example 89b) from 2-(2-methoxy-phenyl)-1-(morpholin-4-yl)-ethanone and chlorosulfonic acid.

Example 131 a) In analogy to Example 1, part a), from 4-tert-butyl-N-[6-(2-amino-ethoxy)-5-(2-chloro-5-methoxy-phenoxy)-pyrimidin-4-yl]-benzene-sulfonamide and phenyl isocyanate there was obtained 4-tert-butyl-N-[5-(2-chloro-5-methoxy-phenoxy)-6-[2-(3-phenyl-ureido)-ethoxy]-pyrimidin-4-yl]-benzenesulfonamide. MS: 526 (M–SO$_2$Cl).

Preparation of the starting material b) The above starting material, MS: 407 (M–SO$_2$Cl), was prepared in analogy to Example 1h), by replacing ethylene glycol by ethanolamine and using the compound from Example 20b).

Example 132

In analogy to Example 1, part a), from 4-tert-butyl-N-[6-(2-amino-ethoxy)-5-(2-chloro-5-methoxy-phenoxy)-pyrimidin-4-yl]-benzene-sulfonamide and 2-fluoro-isocyanate there was obtained 4-tert-butyl-N-[5-(2-chloro-5-methoxy-phenoxy)-6-[2-[3-(2-fluoro-phenyl)-ureido]-ethoxy]-pyrimidin-4-yl]-benzenesulfonamide. MS: 544 (M–SO$_2$Cl).

Example 133

In analogy to Example 2, part a), from 2-pyridylcarboxylic acid azide and 4-tert-butyl-N-[6-(2-amino-ethoxy)-5-(2-chloro-5-methoxy-phenoxy)-pyrimidin-4-yl]-benzene-sulfonamide there was obtained 4-tert-butyl-N-[5-(2-chloro-5-methoxy-phenoxy)-6-[2-(3-pyridin-2-yl-ureido)-ethoxy]-pyrimidin-4-yl]-benzenesulfonamide. MS: 627.4 (M+H).

Example 134

In analogy to Example 2, part a), from 4-pyridylcarboxylic acid azide and 4-tert-butyl-N-[6-(2-amino-ethoxy)-5-(2-chloro-5-methoxy-phenoxy)-pyrimidin-4-yl]-benzene-sulfonamide there was obtained 4-tert-butyl-N-[5-(2-chloro-5-methoxy-phenoxy)-6-[2-(3-pyridin-4-yl-ureido)-ethoxy]-pyrimidin-4-yl[-benzenesulfonamide. MS: 627.5 (M+H).

Example 135

In analogy to Example 2, part a), from 3-pyridylcarboxylic acid azide and 4-tert-butyl-N-[6-(2-amino-ethoxy)-5-(2-chloro-5-methoxy-phenoxy)-pyrimidin-4-yl]-benzene-sulfonamide there was obtained 4-tert-butyl-N-[5-(2-chloro-5-methoxy-phenoxy)-6-[2-(3-pyridin-3-yl-ureido)-ethoxy]-pyrimidin-4-yl]-benzenesulfonamide. MS: 407 (M–SO$_2$—C$_6$N$_4$N$_2$O).

Example 136

In analogy to Example 38, by oxidizing the compound prepared in Example 135 there was prepared 4-tert-butyl-N-[5-(2-chloro-5-methoxy-phenoxy)-6-[2-(3-1-oxy-pyridin-4-yl)-ureido]-ethoxy]-pyrimidin-4-yl]-benzenesulfonamide.

Example 137 a) In analogy to Example 2, part a), from 4-tert-butyl-N-[6-(2-amino-ethoxy)-5-(2-methoxy-phenoxy)-2-methyl-pyrimidin-4-yl]-benzene-sulfonamide and 2-pyridylcarboxylic acid azide there was obtained 4-tert-butyl-N-[5-(2-methoxy-phenoxy)-2-methyl-6-[2-(3-pyridin-2-yl-ureido)-ethoxy]-pyrimidin-4-yl]-benzenesulfonamide. MS: 607.4 (M+H).

Preparation of the starting material b) The above compound, MS: 487.5 (M+H), was obtained in analogy to Example 1, part h), from 4-tert-butyl-N-[6-chloro-5-(2-methoxy-phenoxy)-2-methyl-pyrimidin-4-yl]-benzenesulfonamide (preparation described in EP 510526) using ethanolamine in place of ethylene glycol.

Example 138

110 mg of N-[6-(2-hydroxy-ethoxy)-5-(3,5-dimethoxy-phenoxy)-pyrimidine-4-yl]-1,3-benzodioxol-5-sulfonamide were dissolved in 3 ml of dry THF, then 3 ml of a 2M solution of COCl$_2$ in toluene were added. The mixture was left to react at room temperature for 2 days. Then, the solvent and the excess reagent were distilled off. The residue was dissolved in 2 ml of absolute dioxane and 250 mg of 2-hydroxymethyl-pyridine were added. This solution was held at 70° C. for 2 hours. Then, the volatile components were distilled off. The residue remaining behind was chromatographed on silica gel with ethyl acetate as the eluent. There were obtained 70 mg of carboxylic acid 2-[6-(1,3-benzodioxol-5-ylsulfonylamino)-5-(3,5-dimethoxy-phenoxy)-pyrimidine-4-yloxy]-ethyl ester pyridin-3-ylmethyl ester. MS: 627.3 (M+H$^+$).

Example 139

In analogy to Example 138, from 250 mg of N-[6-(2-hydroxy-ethoxy)-5-(2-chloro-5-methoxy-phenoxy)-pyrimidin-4-yl]-1,3-benzodioxol-5-sulfonamide there was obtained carboxylic acid 2-[6-(1,3-benzodioxol-5-sulfonylamino)-5-(2-chloro-5-methoxy-phenoxy)-pyrimidin-4-yloxy]-ethyl ester pyridin-2-ylmethyl ester. M.p. 148°–150° C. (from EtOH).

Example 140

In analogy to Example 138, from 250 mg of N-[6-(2-hydroxy-ethoxy)-5-(2-chloro-5-methoxy-phenoxy)-pyrimidin-4-yl]-1,3-benzodioxol-5-sulfonamide there was obtained carboxylic acid 2-[6-(1,3-benzodioxol-5-ylsulfonylamino)-5-(2-chloro-5-methoxy-phenoxy)-pyrimidin-4-yloxy]-ethyl ester pyridin-2-ylmethyl ester. MS: 629.2 (M–H$^-$).

Example 141

In analogy to Example 138, from 175 mg of 4-tert-butyl-N-[6-(2-hydroxy-ethoxy)-5-(2-chlor-5-methoxy-phenoxy)-pyrimidin-4-yl)-benzenesulfonamide and 2-hydromethyl-pyridine there was obtained carboxylic acid 2-[6-(4-tert-butyl-benzenesulfonylamino)-5-(2-chloro-5-methoxy-phenoxy)-pyrimidin-4-yloxy]-ethyl ester pyridin-2-ylmethyl ester. IR: 1751 cm$^{-1}$ (ester C=O).

Example 142

In analogy to Example 138, from 125 mg of N-[6-(2-hydroxy-ethoxy)-5-(2-chloro-5-methoxy-phenoxy)-pyrimidin-4-yl]-1,3-benzodioxol-5-sulfonamide and 3-(hydroxymethylfuran) there was obtained carboxylic acid 2-[6-(1,3-benzodioxol-5-ylsulfonylamino)-5-(2-chloro-5-methoxy-phenoxy)-pyrimidin-4-yloxy]-ethyl ester furan-3-ylmethyl ester. MS: 620 (M+H$^+$).

Example 143

0.3 ml of a solution of phosgene 20% in toluene was added to a solution of 0.1 g of 4-tert-butyl-N-[5-(2-chloro-5-methoxy-phenoxy)-6-(2-hydroxy-ethoxy)-2-methyl-pyrimidin-4-yl]-benzenesulfonamide (EP-A- 0526,708) in 1 ml of dichloromethane. The reaction mixture was stirred at 20° C. for 30 minutes and concentrated. The residue in 5 ml of toluene was treated with 0.183 ml of 3-hydroxymethylpyridine and concentrated. The residue was partitioned between chloroform and water, the organic phase was dried and concentrated. After silica gel chromatography with dichloromethane-ethyl acetate 8:2 and crystallization from ethanol there were obtained 43 mg of carboxylic acid 2-[6-(4-tert-butyl-phenylsulfonylamino)-5-(2-chloro-5-methoxy-phenoxy)-2-methyl-pyrimidine-4-yloxy]-ethyl ester pyridin-3-ylmethyl ester. M.p. 118°–119° C. MS: M=657.

Example 144

In analogy to Example 143, from 4-tert-butyl-N-[5-(2-chloro-5-methoxy-phenoxy)-6-(2-hydroxy-ethoxy)-2-methyl-pyrimidin-4-yl]-benzenesulfonamide and 2-hydroxymethylpyridine there was obtained carboxylic acid 2-[6-(4-tert-butyl-phenylsulfonylamino)-5-(2-chloro-5-methoxy-phenoxy)-2-methyl-pyrimidin-4-yloxy]-ethyl ester pyridin-2-ylmethyl ester, m.p. 122° C., MS: M=657.

Example 145

In analogy to Example 143, from 4-tert-butyl-N-[5-(2-chloro-5-methoxy-phenoxy)-6-(2-hydroxy-ethoxy)-2-methyl-pyrimidin-4-yl]-benzenesulfonamide and 4-hydroxymethylpyridine there was obtained carboxylic acid 2-[6-(4-tert-butyl-phenylsulfonylamino)-5-(2-chloro-5-methoxy-phenoxy)-2-methyl-pyrimidin-4-yloxy]-ethyl ester pyrimidin-4-ylmethyl ester, foam, MS: M=657.

Example 146

In analogy to Example 138, from 4-tert-butyl-N-[6-(2-hydroxy-ethoxy)-5-(2-methoxy-phenylsulfanyl)-2,2'-bipyrimidin-4-yl]-benzene-sulfonamide and 3-hydroxymethylpyridine there was obtained carboxylic acid 2-[6-(4-tert-butyl-phenylsulfonylamino)-5-(2-methoxy-phenylsulfanyl)-2,2'-bipyrimidin-4-yloxy]-ethyl ester pyridin-3-ylmethyl ester.

Example 147

In analogy to Example 138, from 4-tert-butyl-N-[6-(2-hydroxy-ethoxy)-5-(2-methoxy-phenylsulfanyl)-2-methyl-pyrimidin-4-yl]-benzenesulfonamide and 3-hydroxymethylpyridine there was obtained carboxylic acid 2-[6-(4-tert-butyl-phenylsulfonylamino)-5-(2-methoxy-phenylsulfanyl)-2-methyl-pyrimidin-4-yloxy]-ethyl ester pyridin-3-ylmethyl ester.

Example 148 a) In analogy to Example 2, part a), from N-[2-(2-benzyloxy-ethyl)-5-(2-chloro-5-methoxy-phenoxy)-6-(2-hydroxy-ethoxy)-pyrimidin-4-yl]- 1,3-benzodioxol-5-sulfonamide and 2-pyridylcarboxylic acid azide there was obtained pyridin-2-ylcarbamic acid 2-[6-(1,3-benzodioxol-5-ylsulfonylamino)-2-(2-benzyloxy-ethyl)-5-(2-chloro-5-methoxy-phenoxy)-pyrimidin-4-yloxy]-ethyl ester. M.p. 143° C.

b) The starting material used above was obtained according to the process of Example 1, parts d) and e), and Example 2, parts b), c) and d), replacing formamidine acetate by 2-benzyloxyethylamidine hydrochloride in Example 1 d).

Example 149 a) In analogy to Example 2, part a), from N-[5-(2-chloro-5-methoxy-phenoxy)-6-(2-hydroxy-ethoxy)-pyrimidin-4-yl]-3-isopropyl-4-methoxy-benzenesulfonamide and 2-pyridylcarboxylic acid azide there was obtained pyridin-2-ylcarbamic acid 2-[5-(2-chloro-5-methoxy-phenoxy)-6-(3-isopropyl-4-methoxy-phenylsulfonylamino)-pyrimidin-4-yloxy]-ethyl ester. M.p. 191°–193° C.

b) The starting material used above, m.p. 167°–168° C., was obtained from the compound of Example 1 e) by reaction with (4-methoxy-3-isopropyl-phenylsulfonamide) K analogously to Example 1g) and subsequent glycolysis according to Example 1h ).

Example 150 a) In analogy to Example 2, part a), from N-[5-(2-chloro-5-methoxy-phenoxy)-6-(2-hydroxy-ethoxy)-2-(3-methoxy-propyl)-pyrimidin-4-yl]-1,3-benzodioxol-5-sulfonamide and 2-pyridylcarboxylic acid azide there was obtained pyridin-2-ylcarbamic acid 2-[6-(1,3-benzodioxol-5-ylsulfonylamino)-5-(2-chloro-5-methoxy-phenoxy)-2-(3-methoxy-propyl)-pyrimidin-4-yloxy]-ethyl ester. M.p. 163°–164° C.

b) The above starting material, m.p. 137° C., was obtained in analogy to Example 10, parts b)–g), using methoxybutyronitrile in place of methoxyproprionitrile in 10b).

Example 151

In analogy to Example 2, part a), from 2-pyridinecarboxylic acid azide and 4-dimethylamino-N-[6-(2-hydroxy-ethoxy)-5-(2-methoxy-phenoxy)-2-morpholin-4-yl-pyrimidin-4-yl]-benzenesulfonamide there was obtained pyridin-2-ylcarbamic acid 2-[6-(4-dimethylaminophenylsulfonylamino)-5-(2-methoxyphenoxy)-2-morpholin-4-yloxy]-ethyl ester. MS: 664.4 (M–H).

The starting material used above was prepared according to Example 72, part b) using (4-dimethylaminobenzenesulfonamide) K as the reaction component.

Example 152

In analogy to Example 1 there were obtained:

Furan-3-ylcarbamic acid 2-[6-(1,3-benzodioxol-5-ylsulfonylamino)- 5-(2-chlor-5-methoxy-phenoxy)-pyrimidin-4-yloxy]-ethyl ester, MS: 604,9 (M+H$^+$), pyridin-2-ylcarbamic acid 2-[6-(1,3-benzodioxol-5 -ylsulfonylamino)-5 -(2-methoxy-phenoxy)-2-methylsulfanyl-pyrimidin- 4-yloxy]-ethyl ester, Mp. 171°–172° C. (from ethanol), pyridin-2-ylcarbamic acid 2-[6-(1,3-benzodioxol-5 -ylsulfonylamino)-5-(2-chlor-5-methoxy-phenoxy)-2-(4-methoxyphenyl)-pyrimidin- 4-yloxy]-ethyl ester, mp.135° C. (dec.), furan-3-ylcarbamic acid 2-[6-(1,3-benzodioxol-5-ylsulfonylamino)- 5-(2-chlor-5-methoxy-phenoxy)-2-(4-methoxyphenyl)-pyrimidin-4 -yloxy]-ethyl ester, MS: 711,2 (M+H$^\oplus$), pyridin-2-ylcarbamic acid 2-[6-(4-tert.butyl-phenylsulfonylamino)- 5-(2-methoxy-phenoxy)-2-methylsulfanyl-pyrimidin-4-yloxy]-ethyl ester, mp. 155° C. (from ethanol), pyridin-2-ylcarbamic acid 2-[6-(1,3-benzodioxol-5 -ylsulfonylamino)-5-(2-methoxy-phenoxy)-2-(3-methoxy-phenyl)-pyrimidin- 4-yloxy]-ethyl ester, mp. 199°–200° C., pyridin-2-ylcarbamic acid 2-[6-(1,3-benzodioxol-5 -ylsulfonylamino)-5-(2-chlor-5-methoxy-phenoxy)-2-morpholin-4-yl-pyrimidin- 4-yloxy]-ethyl ester, mp. 199°–200° C. (from ethanol), pyridin-2-ylcarbamic acid 2-[6-(4-tert.butyl-phenylsulfonylamino)- 5 -(2-methoxy-phenoxy)-2-(4-methoxy-phenyl)-pyrimidin-4-yloxy]-ethyl ester, mp. 168° C., pyridin-2-ylcarbamic acid 2-[6-(1,3-benzodioxol-5 -ylsulfonylamino)-5-(2-chlor-5-methoxy-phenoxy)-2-(2-methoxyethoxy)-pyrimidin- 4-yloxy]-ethyl ester, mp. 188° C., pyridin-2-ylcarbamic acid 2-[6-(4-tert.butyl-phenylsulfonylamino)- 5 -(2-chlor-5-methoxy-phenoxy)-2-morpholin-4-yl-pyrimidin-4-yloxy]-ethyl ester, mp. 219°–220° C., pyridin-2-ylcarbamic acid 2-[6-(4-tert.butyl-phenylsulfonylamino)- 5-(2-methoxy-phenoxy)-2-(3-methoxy-phenyl)-pyrimidin-4-yloxy]-ethyl ester, mp. 178°–179° C. (from ethanol), pyridin-2-ylcarbamic acid 2-[6-(1,3-benzodioxol-5 -ylsulfonylamino)-5-(2-methoxy-phenoxy)-2-(3,4,5-trimethoxyphenyl)-pyrimidin- 4-yloxy]-ethyl ester, MS: 748,4 (M+H$^\oplus$), pyridin-2-ylcarbamic acid 2-[5-(2-chlor-5-methoxy-phenoxy)-6-[4 -methylsulfanyl-3-(morpholin-4-ylcarbonyl)-phenylsulfonylamino]-pyrimidin- 4-yloxy]-ethyl ester, mp. 203° C. (dec.), pyridin-2-ylcarbamic acid 2-[6-(4-tert.butyl-phenylsulfonylamino)- 5-(2-chlor-5-methoxy-phenoxy)-2-methylsulfanyl-pyrimidin-4-yloxy]-ethyl ester, mp. 168°–169° C. (from ethanol), pyridin-2-ylcarbamic acid (RS)-2-[6-(1,3-benzodioxol-5-ylsulfonylamino)- 5-(2-chlor-5-methoxy-phenoxy)-2-(2,3-dimethoxy-propoxy)-pyrimidin- 4-yloxy]-ethyl ester, mp. 173°–174° C. (from ethanol), pyridin-2-ylcarbamic acid 2-[6-(1,3-benzodioxol-5 -ylsulfonylamino)-5-(2-chlor-5 -methoxy-phenoxy)-2-(2-methylsulfanyl-ethoxy)-pyrimidin- 4-yloxy]-ethyl ester, mp. 158°–159° C. (from ethanol), pyridin-2-ylcarbamic acid 2-[6-(4-tert.butyl-phenylsulfonylamino)- 2-furan-2-ylmethoxy-5-(2-methoxy-phenoxy)-pyrimidin-4-yloxy]-ethyl ester, MS: 690,2 (M+H$^+$), pyridin-2-ylcarbamic acid 2-[5-(2-methoxy-phenoxy)-2-(3 -methoxy-phenyl)-6-(4-methylsulfanyl-3-morpholin-4-ylcarbonyl-phenylsulfonylamino)-pyrimidin- 4-yloxy]-ethyl ester, MS: 801,4 [(M–H)$^\oplus$], pyridin-2-ylcarbamic acid (RS)-2-[6-(1,3-benzodioxol-5-ylsulfonylamino)- 5-(2-chlor-5-methoxy-phenoxy)-2-(2-methylsulfinyl-ethoxy)-pyrimidin- 4-yloxy]-ethyl ester, mp. 183° C. (from ethanol), thiophen-3-ylcarbamic acid 2-[6-(1,3-benzodioxol-5 -ylsulfonylamino)-5-(2-chlor-5-methoxy-phenoxy)-2-(2-methoxy-ethoxy)-pyrimidin- 4-yloxy]-ethyl ester, MS: 695,2 (M+H$^\oplus$), pyridin-2-ylcarbamic acid 2-[6-(4-tert.butyl-phenylsulfonylamino)- 5-(2-chlor-5-methoxy-phenoxy)-2-methylsulfanyl-pyrimidin-4-yloxy]-ethyl ester, mp. 211°–212° C. (from ethanol), thiophen-3-ylcarbamic acid (RS)-2-[6-(1,3-benzodioxol-5 -ylsulfonylamino)-5-(2-chlor-5-methoxy-phenoxy)-2-(2-methylsulfinyl-ethoxy)-pyrimidin- 4-yloxy]-ethyl ester, MS: 727,3 (M+H$^\oplus$), pyridin-2-ylcarbamic acid 2-[6-(4-methoxy-5 -phenylsulfonylamino)-5-(2-methoxy-phenoxy)-2,2'-bipyrimidin-4 -yloxy]-ethyl ester, mp. 188°–189° C. (from ethanol), thiophen-3-ylcarbamic acid 2-[6-(4-tert.butyl-phenylsulfonylamino)- 5-(2-methoxy-phenoxy)-2,2'-bipyrimidin-4 -yloxy]-ethyl ester, MS: 677,3 (M+H$^\oplus$), thiophen-2-ylcarbamic acid 2-[6-(4-tert.butyl-phenylsulfonylamino)- 5-(2-methoxy-phenoxy)-2,2'-bipyrimidin-4 -yloxyl-ethyl ester, MS: 675,3 [(M–H)$^-$], pyridin-2-ylcarbamic acid 2-[6-(1,3-benzodioxol-5 -ylsulfonylamino)-5-(3,5-dimethoxy-phenoxy)-2-phenyl-pyrimidin-4 -yloxy]-ethyl ester, pyridin-2-ylcarbamic acid 2-[6-(1,3-benzodioxol-5 -ylsulfonylamino)-5-(2-methoxy-phenoxy)-(2-methoxy-phenyl)-pyrimidin- 4-yloxy]-ethyl ester, mp. 157° C. (dec.), thiophen-3-ylcarbamic acid 2-[6-(1,3-benzodioxol-5 -sulfonylamino)-5-(2-methoxy-phenoxy)-2-(2-methoxy-phenyl)-pyrimidin- 4-yloxy]-ethyl ester, MS: 693,1 [(M+H)$^\oplus$], pyridin-2-ylcarbamic acid 2-[2-(1,3-benzodioxol-5-yl)-6-(1,3 -benzodioxol-5-ylsulfonylamino)-5-(2-methoxy-phenoxy)-pyrimidin-4 -yloxy]-ethyl ester, mp. 185°–186° C. (from ethanol), pyrimidin-2-ylcarbamic acid 2-[6-(1,3-benzodioxol-5 -ylsulfonylamino)-5-(2-chlor-5-methoxy-phenoxy)-pyrimidin-4-yloxy]-ethyl ester, MS: 615,2 [(M–H)$^\oplus$], pyrimidin-2-ylcarbamic acid 2-[5-(2-methoxy-phenoxy)-6-phenyl-sulfonylamino- 2,2'-bipyrimidin-4-yloxy]-ethyl ester, mp. 190° C. (from ethanol), pyridin-2-ylcarbamic acid 2-[5-(2-methoxy-phenoxy)-6-(4-methyl-phenylsulfonylamino)- 2,2'-bipyrimidin-4-yloxy]-ethyl ester, mp. 194° C. (from ethanol), thiophen-3-ylcarbamic acid 2-[5-(2-methoxy-phenoxy)-6-(4 -methoxy-phenylsulfonylamino)-2,2'-bipyrimidin-4-yloxy]-ethyl ester, MS: 649,4 [M–H]$^-$, pyrimidin-2-ylcarbamic acid 2-[6-(4-tert.butyl-phenylsulfonylamino)- 5-(2-methoxy-phenoxy)-2,2'-bipyrimidin-4 -yloxy]-ethyl ester, MS: 671,4 [(M–H)$^-$], furan-2-ylcarbamic acid 2-[5-(2-methoxy-phenoxy)-6-(4-methoxy-phenylsulfonylamino)- 2,2'-bipyrimidin-4-yloxy]-ethyl ester, MS: 635,4 [M+H$^+$], pyridin-2-ylcarbamic acid 2-[6-(4-isobutyl-phenylsulfonylamino)- 5-(2-methoxy-phenoxy)-2,2'-bipyrimidin-4-yloxy]-ethyl ester, mp. 176°–177° C., pyrazin-2-ylcarbamic acid 2-[5-(2-methoxy-phenoxy)-6-(4 -methoxy-phenylsulfonylamino)-2,2'-bipyrimidin-4-yloxy]-ethyl ester, mp. 182°–183 ° C., furan-2-ylcarbamic acid 2-[6-(4-tert.butyl-phenylsulfonylamino)-5 -(2-methoxy-phenoxy)-2,2'-bipyrimidin-4-yloxy]-ethyl ester, MS: 659,5 [(M–H)$^-$], pyridin-2-ylcarbamic acid (S)-2-[6-(1,3-benzodioxol-5-ylsulfonylamino)- 5-(2-chlor-5-methoxy-phenoxy)-2-(2,2-dimethyl-1,3-dioxolan- 4-ylmethoxy)-pyrimidin-4-yloxy]-ethyl ester, mp. 178° C. (from ethanol), pyridin-2-ylcarbamic acid 2-[6-(4-methoxy-3-morpholin-4-ylcarbonyl-phenylsulfonylamino)-5-(2-methoxy-phenoxy)-2-(2 -methoxy-phenyl)-pyrimidin-4-yloxy]-ethyl ester, top. 147° C. (dec.),
pyridin-2-ylcarbamic acid 2-[6-(1,3-benzodioxol-5 -ylsulfonylamino)-5-(2-methoxy-phenoxy)-2-piperidin-1-yl-pyrimidin- 4-yloxy]-ethyl ester, mp. 214°–215° C.,
pyridin-2-ylcarbamic acid 2-[6-(1,3-benzodioxol-5 -ylsulfonylamino)-5-(2-methoxy-phenoxy)-2-thiomorpholin-4-yl-pyrimidin- 4-yloxy]-ethyl ester, mp. 210° C.,
pyridin-2-ylcarbamic acid 2-[6-(1,3-benzodioxol-5 -ylsulfonylamino)-5-(2-methoxy-phenoxy)-2-prop-2-inyloxy-pyrimidin- 4-yloxy]-ethyl ester, mp. 177°–178° C.,
pyridin-2-ylcarbamic acid 2-[5-(1,3-benzodioxol-5 -ylsulfonylamino)-5 -(2-methoxy-phenoxy)-2-pyrrolidin-1 -yl-pyrimidin- 4-yloxy]-ethyl ester, mp. 236° C. (dec.),
pyridin-2-ylcarbamic acid 2-[6-(1,3-benzodioxol-5 -ylsulfonylamino)-5-(2-methoxy-phenoxy)-2-azepan-1-yl-pyrimidin-4 -yloxy]-ethyl ester, mp. 201°–202° C.

Example 153

3 ml of a 1,9 m $COCl_2$-solution in toluene were added dropwise to a solution of 125 mg of N-[6-(2-hydroxy-ethoxy)-2-(2-methoxy-phenoxy)- 2,2'-bipyrimidin-4-yl]-4-isobutyl-benzenesulfonamide in 2 ml of dichloromethane. After 1 hour at room temperature the chlorformate had formed. The excess reagent was distilled off and the residue dissolved in 5 ml of tetrahydrofuran. Thereafter, 2 ml of a 25% ammonium hydroxide solution were added with vigorous stirring. After 15 minutes at room temperature the resulting carbamate was isolated. There were obtained 100 mg of carbamic acid 2-[6-(4-isobutyl-phenylsulfonylamino)- 5-(2-methoxy-phenoxy)-2,2'-bipyrimidin-4 -yloxy]-ethyl ester. mp. 138°–140° C. (from diethyl ether).

Example 154

In analogy to Example 153 there were obtained:
Morpholin-4-carboxylic acid 2-[6-(4-isobutyl-phenylsulfonylamino)- 5-(2-methoxy-phenoxy)-2,2'-bipyrimidin-4 -yloxy]-ethyl ester, mp. 178°–179° C. (from diethyl ether),
imidazol-1-carboxylic acid 2-[6-(4-isobutyl-phenylsulfonylamino)- 5-(2-methoxy-phenoxy)-2,2'-bipyrimidin-4-yloxy] -ethyl ester, mp. 153° C. (dec.),
imidazol-2-carboxylic acid 2-[6-(4-tert.butyl-phenylsulfonyl)-5-(2 -methoxy-phenoxy)-2-methylsulfonyl-pyrimidin-4-yloxy]-ethyl ester, MS: 646,4 (M+H$^\oplus$),
pyridin-2-ylcarbamic acid 2-[6-(4-tert.butyl-phenylsulfonylamino)- 5-(2-methoxy-phenoxy)-2-methylsulfonyl-pyrimidin-4-yloxy]-ethyl ester, MS: 672,2 (M+H$^\oplus$),
(S)-2-[2-[6-(1,3-benzodioxol-5 -ylsulfonylamino)-5 -(2-methoxy-phenoxy)- 2-phenyl-pyrimidin-4-yloxy]-ethoxycarbonylamino]-3 -phenyl-propionic acid tert.butylester, MS: 785,4 (M+H$^\oplus$),
(S)-2-[2-[6-(1,3-benzodioxol-5-ylsulfonylamino)-5-(2-methoxy-phenoxy)- 2-phenyl-pyrimidin-4-yloxy]-ethoxy carbonylamino]-3 -phenyl-propionic acid ethyl ester, MS: 757 (M+H$^\oplus$),
thiazol-2-ylcarbamic acid 2-[5-(2-methoxy-phenoxy)-6-(4 -methoxy-phenylsulfonylamino)-2,2'-bipyrimidin-4-yloxy]-ethyl ester, MS: 650,3 [(M–H)$^-$].

Example 155

In analogy to Example 138 there were obtained:
Carboxylic acid 1,3-benzodioxol-5-ylmethyl ester 2-[6-(1,3 -benzodioxol-5-ylsulfonylamino)-5-(2-chlor-5-methoxy-phenoxy)-pyrimidin- 4-yloxy]-ethyl ester, mp. 154°–155° C. (from ethanol),
carboxylic acid 2-[6-(1,3-benzodioxol-5-ylsulfonylamino)- 5-(2 -methoxy-phenoxy)-2-(2-methoxy-phenyl)-pyrimdin-4-yloxy]-ethyl ester, MS: 692,4 (M+H$^\oplus$),
carboxylic acid 2-[6-(4-tert.butyl-phenylsulfonylamino)-5-(2 -methoxy-phenoxy)-2,2'-bipyrimidin-4-yloxy]-ethyl ester-pyridin-3 -ylmethyl ester, MS: 685,4 [(M–H)$^-$],
carboxylic acid 2-[6-(4-tert.butyl-phenylsulfonylamino)-5-(2 -methoxy-phenoxy)-2,2'-bipyrimidin-4-yloxy]-ethyl ester-furan-2 -ylmethyl ester, MS: 674,4 [(M–H)$^-$],
carboxylic acid 2-[6-(4-tert.butyl-phenylsulfonylamino)-5-(2 -methoxy-phenoxy)-2,2'-bipyrimidin-4-yloxy]-ethyl ester-furan-3 -ylmethyl ester, MS: 674,4 [(M–H)$^-$].

Example 156

By saponification of the ethyl ester groupf of [S]-2-[2-[6-(1,3 -benzodioxol-5-ylsulfonylamino)-5-(2-methoxy-phenoxy)-2-phenyl-pyrimidin- 4-yloxy]-ethoxycarbonylamino]-3-phenyl-propionic acid ethyl ester with KOH there was obtained (S)-2-[2-[6-(1,3-benzodioxol-5 -ylsulfonylamino)-5-(2-methoxy-phenoxy)-2-phenyl-pyrimidin-4 -yloxy]-ethoxycarbonylamino]-3-phenyl-propionic acid (white solid). MS: 729,3 (M+H$^+$).

Example 157

By treatment with 1N HCl in dioxan at 80° for 1 hour there was obtained from pyridin-2-ylcarbamic acid (S)-2-[6-(1,3-benzodioxol-5 -ylsulfonylamino)-5-(2-chlor-5-methoxy-phenoxy)-2-(2,2-dimethyl-1,3 -dioxolan-4-yl-methoxy)-pyrimidin-4-yloxy]-ethyl ester the pyridin-2 -ylcarbamic acid (R)-2-[6-(1,3-benzodioxol-5-sulfonylamino)-5-(2-chlor- 5 -methoxy-phenoxy)-2-(2,3-dihydroxy-propoxy)-6-(2-hydroxy-ethoxy)-pyrimidin- 4-yloxy]-ethyl ester, mp. 142°–143° C. (from ethanol).

Example A

Tablets containing the following ingredients can be produced in a conventional manner:

| Ingredient | Per tablet |
| --- | --- |
| Compound of formula I | 10.0–100.0 mg |
| Lactose | 125.0 mg |
| Corn starch | 75.0 mg |
| Talc | 4.0 mg |
| Magnesium stearate | 1.0 mg |

Example B

Capsules containing the following ingredients can be produced in a conventional manner:

| Ingredient | Per capsule |
| --- | --- |
| Compound of formula I | 25.0 mg |
| Lactose | 150.0 mg |
| Corn starch | 20.0 mg |
| Talc | 5.0 mg |

Example C

Injection solutions can have the following composition:

| | |
|---|---|
| Compound of formula I | 3.0 mg |
| Gelatine | 150.0 mg |
| Phenol | 4.7 mg |
| Water for injection solutions | ad 1.0 ml |

Example D 500 mg of compound of formula I are suspended in 3.5 ml of Myglyol 812 and 0.08 g of benzyl alcohol. This suspension is filled into a container having a dosage valve. 5.0 g of Freon 12 under pressure are filled into the container through the valve. The Freon is dissolved in the Myglyol-benzyl alcohol mixture by shaking. This spray container contains about 100 single doses which can be administered individually.

We claim:

1. A compound of the formula

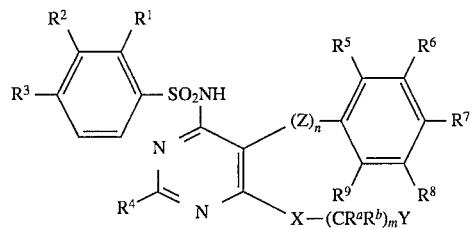

wherein $R^1$–$R^3$ each independently are hydrogen, lower-alkyl, lower-alkoxy, lower-alkylthio, lower-alkenyl, halogen, trifluoromethyl, hydroxy-lower-alkoxy, halo-lower-alkoxy, cyclo-lower-alkyl, hydroxy-lower-alkanoylamino-lower-alkoxy, alkanoylamino-lower-alkyl, carboxy-lower-alkoxy, carboxy-lower-alkyl, lower-alkoxy-carbonyl-lower-alkyl, lower-alkoxycarbonyl-lower-alkoxy, alkanoyloxy-lower-alkoxy, alkanoyloxy-lower-alkyl, alkoxycarbonyl, carboxy, amino, mono- or di-(lower-alkyl)amino or a residue $(R^c,R^d)N$—$C(O)(CH_2)_{0-4}$— or $(R^c,R^d)N$—$C(O)(CH_2)_{0-4}$—;

$R^2$ and $R^3$ together are butadienyl, methylenedioxy, ethylenedioxy or isopropylidenedioxy;

$R^4$ is hydrogen, lower-alkyl, cyclo-lower-alkyl, trifluoromethyl, lower-alkoxy, lower-alkinyloxy, lower-alkylthio, lower-alkylthio-lower-alkyl, lower-alkylthio-lower-alkoxy, hydroxy-lower-alkyl, hydroxy-lower-alkoxy, dihydroxy-lower-alkoxy, lower-alkoxy-lower-alkyl, hydroxy-lower-alkoxy-lower-alkyl, lower-alkoxy-lower-alkoxy, di(lower-alkoxy)-alkoxy, hydroxy-lower-alkoxy-lower-alkoxy, lower-alkylsulphinyl, lower-alkylsulphinyl-lower-alkoxy, lower-alkylsulphonyl, 2-methoxy- 3-hydroxypropoxy, 2-hydroxy-3-phenylpropyl, amino-lower-alkyl, lower-alkylamino-lower-alkyl, di-lower-alkylamino-lower-alkyl, amino, lower-alkylamino, di-lower-alkylamino, arylamino, aryl, arylthio, aryloxy, aryl-lower-alkyl, aryl-lower-alkoxy-lower-alkyl, aryl-lower-alkyl-lower-alkoxy, heterocyclyl, heterocyclyl-lower-alkyl or heterocyclyl-lower-alkoxy, wherein heterocyclyl is a unsubstituted heterocyclyl selected from 2-furyl, 3-furyl, 2-pyrimidinyl, 4-pyrimidinyl, 5-pyrimidinyl, 2-pyridyl, 3-pyridyl, 4-pyridyl, pyridyl N-oxide, 1,2-diazinyl, 1,4-diazinyl, morpholino, thiomorpholino, thiomorpholino-4,4-dioxide, 2,2-dimethyl-1,3-dioxolanyl, 2-thienyl, 3-thienyl, isoxazolyl, oxazolyl, thiazolyl, imidazolyl, pyrrolyl, pyrrolidinyl, piperidinyl, azepanyl, benzofuranyl, benzothienyl, indolyl, purinyl, quinolyl and isoquinolyl or heterocyclyl as defined above mono or disubstituted by lower alkyl, lower alkoxy or halogen and wherein aryl is unsubstituted phenyl or phenyl substituted with halogen, lower-alkyl, lower-alkoxy, lower-alkylenedioxy, carboxy, or trifluoromethyl;

$R^5$ to $R^9$ each independently are hydrogen, halogen, trifluoromethyl, lower-alkyl, lower-alkoxy, lower-alkylthio, lower-alkylsulphinyl or lower-alkylsulphonyl;

$R^6$ and $R^5$ or $R^7$ together are butadienyl, methylene dioxy, ethylenedioxy or isopropylidenedioxy;

$R^a$ and $R^b$ each independently are hydrogen, lower-alkyl, lower-alkoxy or lower-alkylthio;

$R^c$ and $R^d$ each independently are hydrogen, lower-alkyl or aryl; or $R^c$ and $R^d$ together with the N atom to which they are attached are a unsubstituted heterocyclyl selected from 2-furyl, 3-furyl, 2-pyrimidinyl, 4-pyrimidinyl, 5-pyrimidinyl, 2-pyridyl, 3-pyridyl, 4-pyridyl, pyridyl N-oxide, 1,2-diazinyl, 1,4-diazinyl, morpholino, thiomorpholino, thiomorpholino-4,4-dioxide, 2,2-dimethyl-1,3-dioxolanyl, 2-thienyl, 3-thienyl, isoxazolyl, oxazolyl, thiazolyl, imidazolyl, pyrrolyl, pyrrolidinyl, piperidinyl, azepanyl, benzofuranyl, benzothienyl, indolyl, purinyl, quinolyl and isoquinolyl or heterocyclyl as defined above mono or disubstituted by lower alkyl, lower alkoxy or halogen;

Y is a residue —$OC(O)NR^{10}R^{11}$, —$NHC(O)NR^{10}R^{11}$, —$OC(O)R^{10}$ or —$NHC(O)OR^{10}$;

$R^{10}$ is lower-alkyl, cyclo-lower-alkyl, hydroxy-lower alkyl, carboxy-lower-alkyl, lower-alkoxycarbonyl-lower-alkyl, lower-alkanoyloxy-lower-alkyl, aryl, aryl-lower-alkyl, arylcarbamoyl-lower-alkyl, heterocyclyl, heterocyclyl-lower-alkyl or a residue

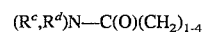

wherein heterocyclyl is a unsubstituted heterocyclyl selected from 2-furyl, 3-furyl, 2-pyrimidinyl, 4-pyrimidinyl, 5-pyrimidinyl, 2-pyridyl, 3-pyridyl, 4-pyridyl, pyridyl N-oxide, 1,2-diazinyl, 1,4-diazinyl, morpholino, thiomorpholino, thiomorpholino-4,4-dioxide, 2,2-dimethyl-1,3-dioxolanyl, 2-thienyl, 3-thienyl, isoxazolyl, oxazolyl, thiazolyl, imidazolyl, pyrrolyl, pyrrolidinyl, piperidinyl, azepanyl, benzofuranyl, benzothienyl, indolyl, purinyl, quinolyl and isoquinolyl or heterocyclyl as defined above mono or disubstituted by lower alkyl, lower alkoxy or halogen and wherein aryl is unsubstituted phenyl or phenyl substituted with halogen, lower-alkyl, lower-alkoxy, lower-alkylenedioxy, carboxy, or trifluoromethyl; and $R^{11}$ is hydrogen or a residue $R^{10}$;

Z is —O—, —S— or —$CH_2$—;

X is —O—, —S— or —NH—;

n is 0 or 1; and m is 1, 2 or 3, and a pharmaceutically usable salt thereof.

2. A compound according to claim 1, in which n=1 and Z=—O—.

3. A compound according to claim 2, in which X=—O—.

4. A compound according to claim 1, in which $R^5$ is halogen, $R^8$ is lower-alkoxy and $R^6$, $R^7$ and $R^9$ are hydrogen.

5. A compound according to claim 1, in which $R^3$ is lower-alkyl and $R^1$ and $R^2$ are hydrogen.

6. A compound according to claim 1, in which $R^4$ is hydrogen, lower alkyl, lower-alkoxy-lower-alkyl, lower-alkylthio, phenyl, lower-alkoxyphenyl, phenyl-lower-alkoxy-lower-alkyl, pyrimidinyl, morpholino, thienyl or cyclo-lower-alkyl.

7. A compound according to claim 1, in which $Y=-OC(O)NR^{10}R^{11}$.

8. A compound according to claim 7, in which $R^{10}$ is heterocyclyl and $R^{11}$ is hydrogen.

9. A compound according to claim 8, in which the heterocyclyl residue $R^{10}$ is a pyridyl residue.

10. A compound according to claim 9, pyridin-2-ylcarbamic acid 2-[6-(1,3-benzodioxol-5-ylsulfonylamino)-5-(2-chloro-5-methoxy-phenoxy)-pyrimidin-4-yloxy]-ethyl ester, pyridin-2-ylcarbamic acid 2-[6-(4-tert-butyl-phenylsulfonylamino)-5-(2-chloro-5-methoxy-phenoxy)-2-methoxymethyl-pyrimidin-4-yloxy]-ethyl ester, pyridin-2-ylcarbamic acid 2-[6-(1,3-benzodioxol-5-ylsulfonylamino)-5-(2-chloro-5-methoxy-phenoxy)-2-methoxymethyl-pyrimidin-4-yloxy]-ethyl ester, pyridin-2-ylcarbamic acid 2-[6-(1,3-benzodioxol-5-ylsulfonylamino)-5-(2-chloro-5-methoxy-phenoxy)-2-(2-methoxyethyl)-pyrimidin-4-yloxy]-ethyl ester, pyridin-2-ylcarbamic acid 2-[6-(1,3-benzodioxol-5-ylsulfonylamino)-5-(2-chloro-5-methoxy-phenoxy)-2-methylsulfanyl-pyrimidin-4-yloxy]-ethyl ester, pyridin-2-ylcarbamic acid 2-[6-(1,3-benzodioxol-5-ylsulfonylamino)-5-(2-methoxy-phenoxy)-2-(4-methoxy-phenyl)-pyrimidin-4-yloxy]-ethyl ester, pyridin-2-ylcarbamic acid 2-[6-(1,3-benzodioxol-5-ylsulfonylamino)-5-(2-methoxy-phenoxy)-2-phenyl-pyrimidin-4-yloxy]-ethyl ester, pyridin-2-ylcarbamic acid 2-[6-(1,3-benzodioxol-5-ylsulfonylamino)-5-(3,5-dimethoxy-phenoxy)-pyrimidin-4-yloxy]-ethylester, pyridin-2-ylcarbamic acid 2-[6-(4-tert-butylphenyl-sulfonylamino)-5-(2-chloro-5-methoxy-phenoxy)-pyrimidin-4-yloxy]ethyl ester, 1-oxy-pyridin-2-ylcarbamic acid 2-[6-(4-tert-butyl-phenylsulfonylamino)-5-(2-chloro-5-methoxy-phenoxy)-pyrimidin-4-yloxy]-ethyl ester, pyridin-2-ylcarbamic acid 2-[6-(4-tert-butyl-phenylsulfonyl-amino)-5-(3-methoxy-phenoxy)-pyrimidin-4-yloxy]-ethyl ester, pyridin-2-ylcarbamic acid 2-[6-(4-tert-butyl-phenylsulfonylamino)-2-isopropyl-5-(2-methoxy-phenoxy)-pyrimidin-4-yloxy]-ethyl ester, pyridin-2-ylcarbamic acid 2-[6-(4-tert-butyl-phenylsulfonylamino)-5-(2-methoxy-phenoxy)-2-propyl-pyrimidin-4-yloxyl-ethyl ester, pyridin-2-ylcarbaminc acid 2-[2-tert-butyl-6-(4-tert-butyl-phenylsulfonylamino)-5-(2-methoxy-phenoxy)-pyrimidin-4-yloxy]-ethyl ester, pyridin-2-ylcarbamic acid 2-[6-(4-tert-butyl-phenylsulfonylamino)-2-cyclopropyl-5-(2-methoxy-phenoxy)-pyrimidin-4-yloxy]-ethyl ester, pyridin-2-ylcarbamic acid 2-[6-(4-tert-butyl-phenylsulfonyl-amino)-5-(2-methoxy-phenoxy)-2-thiophen-2-yl-pyrimidin-4-yloxy]-ethyl ester, pyridin-2-ylcarbamic acid 2-[6-(4-tert-butyl-phenylsulfonylamino)-5-(2-methoxy-phenoxy)-2-methyl-pyrimidin-4-yloxy]-ethyl ester, pyridin-2-ylcarbamic acid-2-[6-(4-tert-butyl-phenylsulfonylamino)-5-(2-methoxy-phenoxy)-2,2'-bipyrimidin-4-yloxy]-ethyl ester, pyridin-2-ylcarbamic acid-2-[6-(2-tert-butyl-phenylsulfonylamino)-5-(2-methoxyphenoxy)-2-morpholin-4-yl-pyrimidin-4-yloxy]-ethyl ester, pyridin-2-yl-carbamic acid 2-[6-(4-cyclopropyl-phenyl-sulfonylamino)-5-(2-methoxy-phenoxy)-2,2'-bipyrimidin-4-yloxy]-ethyl ester, pyridin-2-ylcarbamic acid 2-[5-(2-methoxy-phenoxy)-6-(4-methylsulfanyl-phenylsulfonylamino)-2,2'-bipyrimidin-4-yloxy]-ethyl ester, pyridin-2-ylcarbamic acid 2-[5-(2-methoxy-phenoxy)-6-(4-vinyl-phenylsulfonylamino)-2,2'-bipyridin-4-yloxy]-ethyl ester, pyridyl-2-ylcarbamic acid 2-[5-(2-bromo-5-methoxy-phenoxy)-6-(4-tert-butyl-phenylsulfonylamino)-pyrimidin-4-yloxy]-ethyl ester, pyridin-2-ylcarbamic acid 2-[6-(4-tert-butyl-phenylsulfonylamino)-5-(3,4-dimethoxy-phenoxy)-pyrimidin-4-yloxy]-ethyl ester, pyridin-2-ylcarbamic acid 2-[5-(2-chloro-5-methoxy-phenoxy)-6-(3,4-dimethoxyphenylsulfonylamino)-pyrimidin-4-yloxy]-ethyl ester, acetic acid 2-[4-5-(2-methoxy-phenoxy)-6-(2-pyridin-2-ylcarbamoyloxy-ethoxy)-pyrimidin-4-ylsulfamoyl]-phenoxy]-ethyl ester, pyridin-2-ylcarbamic acid 2-[6-[4-(2-hydroxy-ethoxy)-phenyl-sulfonylamino)-5-(2-methoxy-phenoxy)-pyrimidin-4-yloxy]-ethyl ester, pyridin-2-ylcarbamic acid 2-[6-[4-methoxy-3-[2-morpholin-4-yl-2-oxo-ethoxy)-phenylsulfonylamino]-5-(2-methoxy-phenoxy)-pyrimidin-4-yloxy]-ethyl ester, acetic acid 2-[4-[5-(2-chloro-5-methoxy-phenoxy)-6-(2-pyridin-2-ylcarbamoyloxy-ethoxy)-pyrimidin-4-ylsulfamoyl]-phenoxy]-ethyl ester, pyridin-2-ylcarbamic acid 2-[5-(2-chloro-5-methoxy-phenoxy)-6-[4-(2-hydroxy-ethoxy)-phenylsulfonylamino]-pyrimidin-4-yloxy]-ethyl ester, pyridin-2-ylcarbamic acid 2-[5-(2-chloro-5-methoxy-phenoxy)-6-[4-methoxy-3-(2-morpholin-4-yl-2-oxo-ethoxy)-phenylsulfonyl-amino]-pyrimidin-4-yloxy]-ethyl ester, pyridin-2-ylcarbamic acid 2-[5-(2-chloro-5-methoxy-phenoxy)-6-[4-(2-morpholin-4-yl-2-oxo-ethoxy]-phenylsulfonylamino]-pyrimidin-4-yloxy]-ethyl ester, pyridin-2-ylcarbamic acid 2-[5-(2-methoxy-phenoxy)-6-[4-(2-morpholin-4-yl-2-oxo-ethoxy)-phenylsulfonylamino]-pyrimidin-4-yloxy]-ethyl ester, pyridin-2-ylcarbamic acid 2-[5-(2-methoxy-phenoxy)-6-[4-(3-morpholin-4-yl-3-oxo-propyl)-phenylsulfonylamino]-pyrimidin-4-yloxy]-ethyl ester, pyridin-2-ylcarbamic acid 2-[5-(2-chloro-5-methoxy-phenoxy)-6-[4-(3-morpholin-4-yl-3-oxo-propyl)-phenylsulfonylamino]-pyrimidin-4-yloxy]-ethyl ester, pyridin-2-ylcarbamic acid 2-[6-[4-methoxy-3-(3-morpholin-4-yl-3-oxo-propyl)-phenylsulfonylamino]-5-(2-methoxy-phenoxy)-pyrimidin-4-yloxy]-ethyl ester, pyridin-2-ylcarbamic acid 2-[5-(2-chloro-5-methoxy-phenoxy)-6-[4-methoxy-3-(3-morpholin-4-yl-3-oxo-propyl)-phenylsulfonylamino]-pyrimidin-4-yloxy]-ethyl ester, pyridin-2-ylcarbamic acid 2-[5-(4-methoxy-phenoxy)-6-[4-methoxy-3-(3-piperidin-1-yl-3-oxo-propyl)-phenylsulfonylamino]-pyrimidin-4-yloxy]-ethyl ester, pyridin-2-ylcarbamic acid 2-[5-(2-methoxy-phenoxy)-6-[4-methoxy-3-(3-piperidin-1-yl-3-oxo-propyl)-phenylsulfonylamino]-2,2'-bipyrimidin-4-yloxy]-ethyl ester, pyridin-2-ylcarbamic acid 2-[6-[4-methoxy-2-(3-morpholin-4-yl-3-oxo-propyl)-phenylsulfonylamino]-5-(2-methoxy-phenoxy)-pyrimidin-4-yloxy]-ethyl ester, pyridin-2-ylcarbamic acid 2-[6-[4-(2 -bromo-ethoxy)-phenylsulfonylamino]-5-(2-methoxy-phenoxy)-pyrimidin-4-yloxy]-ethyl ester,
acetic acid 3-[4-[5-(2-methoxy-phenoxy)-6-(2-pyridin-2 -ylcarbamoyloxy-ethoxy)-pyrimidin-4-ylsulfamoyl]-phenoxy]-propyl ester,
pyridin-2-ylcarbamic acid 2-[6-[4-(3 -hydroxy-propoxy)-phenyl-sulfonylamino]-5-(2-methoxy-phenoxy)-pyrimidin-4-yloxy]-ethyl ester,
pyridin-2-ylcarbamic acid 2-[6-[4-methoxy-3-(2-morpholin-4-yl- 2-oxo-ethyl)-phenylsulfonylamino]-5-(2-methoxy-phenoxy)-pyrimidin- 4-yloxy]-ethyl ester,
pyridin-2-ylcarbamic acid 2-[6-(1,3-benzodioxol-5 -ylsulfonylamino)-2-(2-benzyloxy-ethyl]-5-(2-chloro-5 -methoxy-phenoxy)-pyrimidin-4-yloxy]-ethyl ester,
pyridin-2-ylcarbamic acid 2-[5-(2-chloro-5-methoxy-phenoxy)-6 -(3-isopropyl-4-methoxy-phenylsulfonylamino)-pyrimidin-4-yloxy]-ethyl ester,
pyridin-2-ylcarbamic acid 2-[6-(1,3-benzodioxol-5 -ylsulfonylamino)-5-(2-chloro-5-methoxy-phenoxy)-2-(3 -methoxy-propyl)-pyrimidin-4-yloxy]-ethyl ester,
pyridin-2-ylcarbamic acid 2-[6-(4 -dimethylaminophenylsulfonylamino)-5-(2-methoxy-phenoxy)-2-morpholin-4-yl-pyrimidin-4 -yloxy]ethyl ester.

11. A compound according to claim 10, pyridin-2-ylcarbamic acid 2-[6-(4-tert-butyl-phenylsulfonylamino)-5-(2-methoxyphenoxy)- 2,2'-bipyrimidin-4-yloxy]-ethyl ester.

12. A compound according to claim 9,
pyridin-3-ylcarbamic acid 2-[5-(2-chloro-5-methoxy-phenoxy]-6 -(2,3-dihydro-1,4-benzodioxin-6-ylsulfonylamino)-pyrimidin-4 -yloxy]-ethyl ester,
pyridin-4-ylcarbamic acid 2-[6-(1,3-benzodioxol-5 -ylsulfonylamino)-5-(2-chloro-5-methoxy-phenoxy)-pyrimidin-4 -yloxy]-ethyl ester,
pyridin-3-ylcarbamic acid 2-[6-(1,3-benzodioxol-5 -ylsulfonylamino)-5-(2-chloro-5-methoxy-phenoxy)-pyrimidin-4 -yloxy)-ethyl ester,
pyridin-3-ylcarbamic acid 2-[6-(4 -tert-butyl-phenylsulfonylamino)-5-(2-chloro-5-methoxy-phenoxy)-2 -methoxymethyl-pyrimidin-4-yloxy]-ethyl ester,
pyridin-3-ylcarbamic acid 2-[6-(4 -tert-butylphenylsulfonylamino)-5-(2-chloro-5 -methoxy-phenoxy)-pyrimidin-4-yloxy]ethyl ester,
pyridin-4-ylcarbamic acid 2-[6-(4 -tert-butylphenylsulfonylamino)-5-(2-chloro-5 -methoxy-phenoxy)-pyrimidin-4-yloxy]ethyl ester,
1-oxy-pyridin-4-ylcarbamic acid 2-[6-(4 -tert-butyl-phenylsulfonylamino)-5-(2-chloro-5-methoxyphenoxy)-pyrimidin-4 -yloxy]-ethyl ester,
3-[2-[5-(2-chloro-5-methoxy-phenoxy)-6-(2,3-dihydro-1,4 -benzodioxin-6-ylsulfonylamino)-pyrimidin-4 -yloxy]-ethoxycarbonylamino]-1-methyl-pyridinium iodide,
N-[5-(2-chloro-5-methoxy-phenoxy)-6-[2-(1-methyl-pyridin-3 -ylcarbamoyloxy)-ethoxy]-pyrimidin-4-yl]-1,3-benzodioxol-5 -sulfonamide,
pyridin-4-ylcarbamic acid 2-[6-(4 -tert-butyl-phenylsulfonylamino)-5-(3-methoxy-phenoxy)-pyrimidin-4-yloxy]-ethyl ester,
4-[2-[6-(4-tert-butyl-phenylsulfonylamino)-5-(2-chloro-5 -methoxy-phenoxy-pyrimidin-4-yloxy]-ethoxycarbonylamino]-1 -methyl-pyridinium iodide,
pyridin-4-ylcarbamic acid 2-[6-(4 -tert-butyl-phenylsulfonylamino)-2-isopropyl-5-(2-methoxy-phenoxy)-pyrimidin- 4-yloxy]-ethyl ester,
pyridin-4-ylcarbamic acid 2-[6-(4 -tert-butyl-phenylsulfonylamino)-5-(2-methoxy-phenoxy)-2-propyl-pyrimidin-4 -yloxy]-ethyl ester,
pyridin-4-ylcarbamic acid 2-[2-tert-butyl-6-(4 -tert-butylphenylsulfonylamino)-5-(2-methoxy-phenoxy)-pyrimidin-4 -yloxy]-ethyl ester,
pyridin-4-ylcarbamic acid 2-[6-(4 -tert-butyl-phenylsulfonylamino)-2-cyclopropyl-5-(2-methoxy-phenoxy)-pyrimidin- 4-yloxy]-ethyl ester,
pyridin-4-ylcarbamic acid 2-[6-(4 -tert-butyl-phenylsulfonylamino)-5-(2-methoxy-phenoxy)-2-thiophen-2-yl-pyrimidin- 4-yloxy]-ethyl ester,
pyridin-4-ylcarbamic acid 2-[6-(4 -tert-butyl-phenylsulfonylamino)-5-(2-methoxy-phenoxy)-2-methyl-pyrimidin-4 -yloxy]-ethyl ester,
pyridin-4-ylcarbamic acid 2-[6-(4 -tert-butyl-phenylsulfonylamino)-5-(2-methoxy-phenoxy)-2,2'-bipyrimidin-4 -yloxy]-ethyl ester,
pyridin-4-ylcarbamic acid 2-[6-(2 -tert-butyl-phenylsulfonylamino)-5-(2-methoxy-phenoxy)-2-morpholin-4 -yl-pyrimidin-4-yloxy]-ethyl ester,
pyridin-3-ylcarbamic acid 2-[6-(2 -tert-butyl-phenylsulfonylamino)-5-(2-methoxy-phenoxy)-2-morpholin-4 -yl-pyrimidin-4-yloxy]-ethyl ester,
pyridin-4-ylcarbamic acid 2-[6-(4 -tert-butyl-phenylsulfonylamino)-5-(3,4-dimethoxy-phenoxy)-pyrimidin-4 -yloxy] -ethyl ester,
acetic acid 2-[4-5-(2-methoxy-phenoxy)-6-(2-pyridin-4 -ylcarbamoyloxy-ethoxy)-pyrimidin-4-ylsulfamoyl]-phenoxy]-ethyl ester,
acetic acid 2-[4-[5-(2-methoxy-phenoxy)-6-(2-pyridin-4 -ylcarbamoyloxy-ethoxy)-pyrimidin-4-ylsulfamoyl]-phenoxy]-ethyl ester,
pyridin-4-ylcarbamic acid 2-[6-[4-(2-hydroxy-ethoxy)-phenylsulfonylamino]-5-(2-methoxy-phenoxy)-pyrimidin-4-yloxy]-ethyl ester,
pyridin-3-ylcarbamic acid 2-[6-[4-(2 -hydroxy-ethoxy)-phenylsulfonylamino]-5-(2-methoxy-phenoxy)-pyrimidin-4-yloxy]-ethylester,
pyridin-4-ylcarbamic acid 2-[6-[4-methoxy-3-[2-morpholin-4 -yl-2-oxo-ethoxy)-phenylsulfonylamino]-5-(2-methoxy-phenoxy)-pyrimidin- 4-yloxy]-ethylester,
pyridin-4-ylcarbamic acid 2-[5-(2-chloro-5-methoxy-phenoxy)-6 -[4-methoxy-3-(2-morpholin-4-yl-2-oxoethoxy)-phenylsulfonylamino]-pyrimidin-4-yloxy]-ethyl ester,
pyridin-4-ylcarbamic acid 2-[5-(2-methoxy-phenoxy)-6-[4-(2 -morpholin-4-yl-2-oxo-ethoxy)-phenylsulfonylamino]-pyrimidin-4 -yloxy]-ethyl ester.

13. A compound according to claim 8,
1-methyl-pyrrol-2-ylcarbamic acid 2-[6-(1,3-benzodioxol-5 -ylsulfonylamino)-5-(2-chloro-5-methoxy-phenoxy)-pyrimidin-4-yloxy]-ethyl ester,
thiophen-3-ylcarbamic acid 2-[6-(4 -tert-butyl-phenylsulfonylamino)-5-(2-chloro-5-methoxy-phenoxy)-pyrimidin-4 -yloxy]-ethyl ester,
thiophen-3-ylcarbamic acid 2-[6-(1,3-benzodioxol-5 -ylsulfonylamino)-5-(2-chloro-5-methoxy-phenoxy)-pyrimidin-4-yloxy]-ethyl ester,
thiophen-3-ylcarbamic acid 2-[6-(1,3-benzodioxol-5 -ylsulfonylamino)-5-(2-chloro-5-methoxy-phenoxy)-2-methoxymethyl-pyrimidin- 4-yloxy]-ethyl ester,
thiophen-2-ylcarbamic acid 2-[6-(1,3-benzodioxol-5 -ylsulfonylamino)-5-(2-chloro-5-methoxy-phenoxy)-pyrimidin-4-yloxy]-ethyl ester,
thiophen-3-ylcarbamic acid 2-[6-(1,3-benzodioxol-5 -ylsulfonylamino)-5-(2-chlor-5-methoxy-phenoxy)-2-(2 -methoxy-ethyl)-pyrimidin-4-yloxy]-ethyl ester,
pyrazin-2-ylcarbamic acid 2-[6-(4 -tert-butylphenylsulfonylamino)-5-(2-chloro-5 -methoxy-phenoxy)-pyrimidin-4-yloxy]ethyl ester, quinolin-2-ylcarbamic acid 2-[6-(4-tert-butyl-phenylsulfonylamino)-5-(3-methoxy-phenoxy)-pyrimidin-4-yloxy]-ethyl ester, furan-3-ylcarbamic acid 2-[6-(1,3-benzodioxol-5-ylsulfonylamino)-5-(2-chloro-5-methoxy-phenoxy)-pyrimidin-4-yloxy]-ethyl ester, furan-2-ylcarbamic acid 2-[6-(4-tert-butyl-phenylsulfonylamino)-5-(2-methoxy-phenoxy)-2-morpholin-4-yl-pyrimidin-4-yloxy]-ethyl ester, 3-methyl-isoxazol-5-ylcarbamic acid 2-[6-(4-tert-butyl-phenylsulfonylamino)-5-(2-methoxy-phenoxy)-2-morpholin-4-ylpyrimidin-4-yloxy]-ethyl ester, 3-methyl-isoxazol-5-ylcarbamic acid 2-[5-(2-methoxy-phenoxy)-6-(4-methylsulfanyl-phenylsulfonylamino)-2,2'-bipyrimidin-4-yloxy-ethyl ester, pyrazin-2-ylcarbamic acid 2-[6-[4-methoxy-3-[2-morpholin-4-yl-2-oxo-ethoxy)-phenylsulfonylamino]-5-(2-methoxy-phenoxy)-pyrimidin-4-yloxy]-ethyl ester, pyrazin-2-ylcarbamic acid 2-[5-(2-chloro-5-methoxy-phenoxy)-6-[4-methoxy-3-(2-morpholin-4-yl-2-oxo-ethoxy)-phenylsulfonylamino]-pyrimidin-4-yloxy]-ethyl ester, pyrazin-2-ylcarbamic acid 2-[5-(2-chloro-5-methoxy-phenoxy)-6-[4-(2-morpholin-4-yl-2-oxo-ethoxy]-phenylsulfonylamino]-pyrimidin-4-yloxy]-ethyl ester, pyrimidin-2-ylcarbamic acid 2-[5-(2-chloro-5-methoxy-phenoxy)-6-[4-methoxy-3-(3-morpholin-4-yl-3-oxo-propyl)-phenylsulfonylamino]-pyrimidin-4-yloxy]-ethyl ester.

14. A compound according to claim 7, in which $R^{10}$ is aryl or cyclo-lower-alkyl and $R^{11}$ is hydrogen.

15. A compound according to claim 14, 1,3-benzodioxol-5-ylcarbamic acid 2-[6-(4-tert-butyl-phenylsulfonylamino)-5-(2-chloro-5-methoxy-phenoxy)-pyrimidin-4-yloxy]-ethyl ester, 3-fluorophenylcarbamic acid 2-[6-(4-tert-butylphenylsulfonylamino)-5-(2-chloro-5-methoxy-phenoxy)-pyrimidin-4-yloxy]-ethyl ester, 2-fluorophenylcarbamic acid 2-[(6-(4-tert-butyl-phenyl-sulfonylamino)-5-(2-chloro-5-methoxy-phenoxy)-pyrimidin-4-yloxy]-ethyl ester, phenylcarbamic acid 2-[6-(4-tert-butyl-phenylsulfonylamino)-5-(2-chloro-5-methoxy-phenoxy)pyrimidin-4-yloxy]-ethyl ester, 4-chloro-phenylcarbamic acid 2-[6-(4-tert-butyl-phenylsulfanoylamino)-5-(2-chloro-5-methoxy-phenoxy)-pyrimidin-4-yloxy]-ethyl ester, 3-methoxy-phenylcarbamic acid 2-[6-(4-tert-butyl-phenylsulfonylamino)-5-(2-chloro-5-methoxy-phenoxy)-pyrimidin-4-yloxy]-ethyl ester, 4-trifluoromethyl-phenylcarbamic acid 2-[6-(4-tert-butyl-phenylsulfonylamino)-5-(2-chloro-5-methoxy-phenoxy)-pyrimidin-4-yloxy]-ethyl ester, 2-[2-[6-(4-tert-butyl-phenylsulfonylamino)-5-(2-chloro-5-methoxy)-pyrimidin-4-yloxy]-ethoxycarbonylamino]-benzoic acid methyl ester, 3-tolylcarbamic acid 2-(6-(4-tert-butyl-phenylsulfonylamino)-5-(2-chloro-5-methoxy-phenoxy)-pyrimidin-4-yloxy]-ethyl ester, 2-methoxy-phenoxycarbamic acid 2-[6-(4-tert-butyl-phenylsulfonylamino)-5-(2-chloro-5-methoxy-phenoxy)-pyrimidin-4-yloxy]-ethyl ester, acetic acid 2-[2-[(6-tert-butyl-phenylsulfonylamino)-5-(2-chloro-5-methoxy)-pyrimidin-4-yloxy]-ethoxycarbonylamino]-phenyl ester, 2-hydroxy-phenylcarbamic acid 2-[6-(4-tert-butylphenylsulfonylamino)-5-(2-chloro-5-methoxy-phenoxy)-pyrimidin-4-yloxy]-ethyl ester, benzylcarbamic acid 2-[6-(4-tert-butylphenylsulfonylamino)-5-(2-chloro-5-methoxy-phenoxy)pyrimidin-4-yloxy]-ethyl ester, phenylcarbamic acid 2-[6-(4-tert-butyl-phenylsulfonylamino)-5-(3-methoxy-phenoxy)-pyrimidin-4-yloxy]-ethyl ester, (R)-1-phenyl-ethylcarbamic acid-2-[6-(4-tert-butyl-phenylsulfonylamino)-5-(3-methoxy-phenoxy)-pyrimidin-4-yloxy]-ethyl ester, cyclohexylcarbamic acid 2-[6-(4-tert-butyl-phenylsulfonylamino)-5-(3-methoxy-phenoxy)-pyrimidin-4-yloxy]-ethyl ester, acetic acid 2-[4-[5-(2-methoxy-phenoxy)-6-(2-phenylcarbamoyloxy-ethoxy)-pyrimidin-4-ylsulfamoyl]-phenoxy]-ethyl ester, acetic acid 2-[4-[6-[2-(2-fluoro-phenylcarbamoyloxy)-ethoxy]-5-(2-methoxy-phenoxy)-pyrimidin-4-ylsulfamoyl]-phenoxy]-ethyl ester, phenylcarbamic acid 2-[6-[4-(2-hydroxy-ethoxy)-phenylsulfonylamino]-5-(2-methoxy-phenoxy)-pyrimidin-4-yloxy]-ethyl ester, 2-fluoro-phenylcarbamic acid 2-[6-[4-(2-hydroxy-ethoxy)-phenylsulfonylamino]-5-(2-methoxy-phenoxy)-pyrimidin-4-yloxy]-ethyl ester, 2-fluoro-phenylcarbamic acid 2-[6-[4-methoxy-3-(2-morpholin-4-yl-2-oxo-ethoxy)-phenylsulfonylamino]-5-(2-methoxy-phenoxy)-pyrimidin-4-yloxy]-ethyl ester, acetic acid 2-[4-[5-(2-chloro-5-methoxy-phenoxy)-6-[2-(2-fluoro-phenylcarbamoyloxy)-ethoxy]-pyrimidin-4-ylsulfamoyl]-phenoxy]-ethyl ester, 2-fluoro-phenylcarbamic acid 2-[5-(2-chloro-5-methoxy-phenoxy)-6-[4-(2-hydroxy-ethoxy)-phenylsulfonylamino]-pyrimidin-4-yloxy]-ethyl ester, 2-fluoro-phenylcarbamic acid 2-[5-(2-chloro-5-methoxy-phenoxy)-6-[4-methoxy-3-(2-morpholin-4-yl-2-oxo-ethoxy)-phenylsulfonylamino]-pyrimidin-4-yloxy]-ethyl ester, phenylcarbamic acid 2-[6-[4-methoxy-3-(2-morpholin-4-yl-2-oxo-ethoxy)-phenylsulfonylamino]-5-(3-methoxy-phenoxy)-pyrimidin-4-yloxy]-ethyl ester,

[5-[5-(2-chloro-5-methoxy-phenoxy)-6-[2-(2-fluorophenylcarbamoyloxy)-ethoxy]-pyrimidin-4-ylsulfamoyl]-2-methoxy-phenoxy]-acetic acid ethyl ester, 5-[5-(2-chloro-5-methoxy-phenoxy)-6-[2-(2-fluoro-phenylcarbamoyloxy)-ethoxy]-pyrimidin-4-ylsulfamoyl]-2-methoxy-phenoxy]-acetic acid, 2-fluoro-phenylcarbamic acid 2-[6-[4-methoxy-3-(2-oxo-2-piperidin-1-yl-ethoxy)-phenylsulfonylamino]-5-(2-methoxy-phenoxy)-pyridin-4-yloxy]-ethyl ester.

16. A compound according to claim 7, isopropylcarbamic acid 2-[6-(4-tert-butyl-phenylsulfonylamino)-5-(2-chloro-5-methoxy-phenoxy)-pyrimidin-4-yloxy]-ethyl ester, ethylcarbamic acid 2-[6-(4-tert-butyl-phenylsulfonylamino)-5-(2-chloro-5-methoxy-phenoxy)-pyrimidin-4-yloxy]-ethyl ester,

[2-[6-(4-tert-butyl-phenylsulfonylamino)-5-(3-methoxy-phenoxy)-pyrimidin-4-yloxy-ethoxycarbonylamino]-acetic acid ethyl ester, 2-[6-(4-tert-butyl-phenylsulfonylamino)-5-(3-methoxy-phenoxy)-pyrimidin-4-yloxy]-ethoxycarbonylaminoacetic acid, 2-hydroxy-ethylcarbamic acid 2-[6-(4-tert-butyl-phenylsulfonylamino)-5-(3-methoxy-phenoxy)-pyrimidin-4-yloxy]-ethyl ester, morpholine-4-carboxylic acid 2-[6-(4-tert-butyl-phenylsulfonylamino)-5-(3-methoxy-phenoxy)-pyrimidin-4-yloxy]-ethyl ester, 2-morpholin-4-yl-2-oxo-ethylcarbamic acid 2-[6-(4-tert-butyl-phenylsulfonylamino)-5-(3-methoxy-phenoxy)-pyrimidin-4-yloxy]-ethyl ester, 2-oxo-2-pyrrolidin-1-yl-ethylcarbamic acid 2-[6-(4-tert-butyl-phenylsulfonylamino)-5-(3-methoxy-phenoxy)-pyrimidin-4-yloxy]-ethyl ester, phenylcarbamoylmethylcarbamic acid 2-[6-(4-tert-butyl-phenylsulfonylamino)-5-(3-methoxy-phenoxy)-pyrimidin-4-yloxy]ethyl ester, 2-[2-[6-(4-tert-butyl-phenylsulfonylamino)-5-(3-methoxy-phenoxy)-pyrimidin-4-yloxy]-ethoxycarbonylamino]-4-methyl-pentanoic acid ethyl ester.

17. A compound according to claim 1 in which Y is —NHC(O)NR$^{10}$R$^{11}$.

18. A compound according to claim 17, 4-tert-Butyl-N-[5-(2-chloro-5-methoxy-phenoxy)-6-[2-(3-phenyl-ureido)-ethoxy]-pyrimidin-4-yl]-benzenesulfonamide, 4-tert-butyl-N-[5-(2-chloro-5-methoxy-phenoxy)-6-[2-[3-(2-fluoro-phenyl)-ureido]-ethoxy]-pyrimidin-4-yl]-benzenesulfonamide, 4-tert-butyl-N-[5-(2-chloro-5-methoxy-phenoxy)-6-[2-(3-pyridin-2-yl-ureido)-ethoxy]-pyrimidin-4-yl]-benzenesulfonamide 4-tert-butyl-N-[5-(2-chloro-5-methoxy-phenoxy)-6-[2-(3-pyridin-4-yl-ureido)-ethoxy]-pyrimidin-4-yl]-benzenesulfonamide, 4-tert-butyl-N-[5-(2-chloro-5-methoxy-phenoxy)-6-[2-(3-pyridin-3-yl-ureido)-ethoxy]-pyrimidin-4-yl]-benzenesulfonamide, 4-tert-butyl-N-[5-(2-chloro-5-methoxy-phenoxy)-6-[2-(3-1-oxy-pyridin-4-yl)-ureido]-ethoxy]-pyrimidin-4-yl]-benzenesulfonamide, 4-tert-butyl-N-[5-(2-methoxy-phenoxy)-2-methyl-6-[2-(3-pyridin-2-yl-ureido)-ethoxy]-pyrimidin-4-yl]-benzenesulfonamide.

19. A compound according to claim 1, in which Y is —OC(O)COR$^{10}$.

20. A compound according to claim 19, carboxylic acid 2-[6-(1,3-benzodioxol-5-ylsulfonylamino)-5-(3,5-dimethoxy-phenoxy)-pyrimidin-4-yloxy]-ethyl ester pyridin-3-ylmethyl ester, carboxylic acid 2-[6-(1,3-benzodioxol-5-sulfonylamino)-5-(2-chloro-5-methoxy-phenoxy)-pyrimidin-4-yloxy]-ethyl ester pyridin-2-ylmethyl ester, carboxylic acid 2-[6-(1,3-benzodioxol-5-ylsulfonylamino)-5-(2-chloro-5-methoxy-phenoxy)-pyrimidin-4-yloxy]-ethyl ester pyridin-2-ylmethyl ester, carboxylic acid 2-[6-(4-tert-butyl-benzenesulfonylamino)-5-(2-chloro-5-methoxy-phenoxy)-pyrimidin-4-yloxy]-ethyl ester pyridin-2-ylmethyl ester, carboxylic acid 2-[6-(1,3-benzodioxol-5-ylsulfonylamino)-5-(2-chloro-5-methoxy-phenoxy)-pyrimidin-4-yloxy]-ethyl ester furan-3-ylmethyl ester, carboxylic acid 2-[6-(4-tert-butyl-phenylsulfonylamino)-5-(2-chloro-5-methoxy-phenoxy)-2-methyl-pyrimidin-4-yloxy]-ethyl ester pyridin-3-ylmethyl ester, carboxylic acid 2-[6-(4-tert-butyl-phenylsulfonylamino)-5-(2-chloro-5-methoxy-phenoxy)-2-methyl-pyrimidin-4-yloxy]-ethyl ester pyridin-2-ylmethyl ester, carboxylic acid 2-[6-(4-tert-butyl-phenylsulfonylamino)-5-(2-chloro-5-methoxy-phenoxy)-2-methyl-pyrimidin-4-yloxy]-ethyl ester pyrimidin-4-ylmethyl ester, carboxylic acid 2-[6-(4-tert-butyl-phenylsulfonylamino)-5-(2-methoxy-phenylsulfanyl)-2,2'-bipyrimidin-4-yloxy]-ethyl ester-pyridin-3-ylmethyl ester, carboxylic acid 2-[6-(4-tert-butyl-phenylsulfonylamino)-5-(2-methoxy-phenylsulfanyl)-2-methyl-pyrimidin-4-yloxy]-ethyl ester pyridin-3-ylmethyl ester.

21. A compound according to claim 1, in which n=1 and Z=—S—.

22. A compound according to claim 21, pyridin-2-ylcarbamic acid 2-[6-(4-tert-butyl-phenylsulfonylamino)-5-(2-methoxy-phenylsulfanyl)-pyrimidin-4-yloxy)-ethyl ester, pyridin-3-ylcarbamic acid 2-[6-tert-butyl-phenylsulfonylamino)-5-(2-methoxy-phenylsulfanyl)-2,2'-bipyrimidin-4-yloxy]-ethyl ester, pyridin-4-ylcarbamic acid 2-[6-(4-tert-butyl-phenylsulfonylamino)-5-(2-methoxy-phenylsulfanyl)-2-methyl-pyrimidin-4-yloxy]-ethyl ester.

23. A pharmaceutical composition comprising an effective amount of a compound of the formula wherein R$^1$–R$^3$ each independently are hydrogen, lower-alkyl, lower-alkoxy, lower-alkylthio, lower-alkenyl, halogen, trifluoromethyl, hydroxy-lower-alkoxy, halo-lower-alkoxy, cyclo-lower-alkyl, hydroxy-lower-alkanoylamino-lower-alkoxy, alkanoylamino-lower-alkyl, carboxy-lower-alkoxy, carboxy-lower-alkyl, lower-alkoxy-carbonyl-lower-alkyl, lower-alkoxycarbonyl-lower-alkoxy, alkanoyloxy-lower-alkoxy, alkanoyloxy-lower-alkyl, alkoxycarbonyl, carboxy, amino, mono- or di-(lower-alkyl)amino or a residue (R$^c$,R$^d$)N—C(O)(CH$_2$)$_{0-4}$O— or (R$^c$,R$^d$)N—C(O)(CH$_2$)$_{0-4}$—;

R$^2$ and R$^3$ together are butadienyl, methylenedioxy, ethylenedioxy or isopropylidenedioxy;

R$^4$ is hydrogen, lower-alkyl, cyclo-lower-alkyl, trifluoromethyl, lower-alkoxy, lower-alkinyloxy, lower-alkylthio, lower-alkylthio-lower-alkyl, lower-alkylthio-lower-alkoxy, hydroxy-lower-alkyl, hydroxy-lower-alkoxy, dihydroxy-lower-alkoxy, lower-alkoxy-lower-alkyl, hydroxy-lower-alkoxy-lower-alkyl, lower-alkoxy-lower-alkoxy, di(lower-alkoxy)-alkoxy, hydroxy-lower-alkoxy-lower-alkoxy, lower-alkylsulphinyl, lower-alkylsulphinyl-lower-alkoxy, lower-alkylsulphonyl, 2-methoxy- 3-hydroxypropoxy, 2-hydroxy-3-phenylpropyl, amino-lower-alkyl, lower-alkylamino-lower-alkyl, di-lower-alkylamino-lower-alkyl, amino, lower-alkylamino, di-lower-alkylamino, arylamino, aryl, arylthio, aryloxy, aryl-lower-alkyl, aryl-lower-alkoxy-lower-alkyl, aryl-lower-alkyl-lower-alkoxy, heterocyclyl, heterocyclyl-lower-alkyl or heterocyclyl-lower-alkoxy, wherein heterocyclyl is a unsubstituted heterocyclyl selected from 2-furyl, 3-furyl, 2-pyrimidinyl, 4-pyrimidinyl, 5-pyrimidinyl, 2-pyridyl, 3-pyridyl, 4-pyridyl, pyridyl N-oxide, 1,2-diazinyl, 1,4-diazinyl, morpholino, thiomorpholino, thiomorpholino-4,4-dioxide, 2,2-dimethyl-1,3-dioxolanyl, 2-thienyl, 3-thienyl, isoxazolyl, oxazolyl, thiazolyl, imidazolyl, pyrrolyl, pyrrolidinyl, piperidinyl, azepanyl, benzofuranyl, benzothienyl, indolyl, purinyl, quinolyl and isoquinolyl or heterocyclyl as defined above mono or disubstituted by lower alkyl, lower alkoxy or halogen and wherein aryl is unsubstituted phenyl or phenyl substituted with halogen, lower-alkyl, lower-alkoxy, lower-alkylenedioxy, carboxy, or trifluoromethyl;

$R^5$ to $R^9$ each independently are hydrogen, halogen, trifluoromethyl, lower-alkyl, lower-alkoxy, lower-alkylthio, lower-alkylsulphinyl or lower-alkylsulphonyl;

$R^6$ and $R^5$ or $R^7$ together are butadienyl, methylene dioxy, ethylenedioxy or isopropylidenedioxy;

$R^a$ and $R^b$ each independently are hydrogen, lower-alkyl, lower-alkoxy or lower-alkylthio;

$R^c$ and $R^d$ each independently are hydrogen, lower-alkyl or aryl; or $R^c$ and $R^d$ together with the N atom to which they are attached are a unsubstituted heterocyclyl selected from 2-furyl, 3-furyl, 2-pyrimidinyl, 4-pyrimidinyl, 5-pyrimidinyl, 2-pyridyl, 3-pyridyl, 4-pyridyl, pyridyl N-oxide, 1,2-diazinyl, 1,4-diazinyl, morpholino, thiomorpholino, thiomorpholino-4,4-dioxide, 2,2-dimethyl-1,3-dioxolanyl, 2-thienyl, 3-thienyl, isoxazolyl, oxazolyl, thiazolyl, imidazolyl, pyrrolyl, pyrrolidinyl, piperidinyl, azepanyl, benzofuranyl, benzothienyl, indolyl, purinyl, quinolyl and isoquinolyl or heterocyclyl as defined above mono or disubstituted by lower alkyl, lower alkoxy or halogen;

Y is a residue —OC(O)NR$^{10}$R$^{11}$, —NHC(O)NR$^{10}$R$^{11}$, —OC(O)R$^{10}$ or —NHC(O)OR$^{10}$;

$R^{10}$ is lower-alkyl, cyclo-lower-alkyl, hydroxy-lower alkyl, carboxy-lower-alkyl, lower-alkoxycarbonyl-lower-alkyl, lower-alkanoyloxy-lower-alkyl, aryl, aryl-lower-alkyl, arylcarbamoyl-lower-alkyl, heterocyclyl, heterocyclyl-lower-alkyl or a residue (R$^c$,R$^d$)N—C(O)(CH$_2$)$_{1-4}$ wherein heterocyclyl is a unsubstituted heterocyclyl selected from 2-furyl, 3-furyl, 2-pyrimidinyl, 4-pyrimidinyl, 5-pyrimidinyl, 2-pyridyl, 3-pyridyl, 4-pyridyl, pyridyl N-oxide, 1,2-diazinyl, 1,4-diazinyl, morpholino, thiomorpholino, thiomorpholino-4,4-dioxide, 2,2-dimethyl-1,3-dioxolanyl, 2-thienyl, 3-thienyl, isoxazolyl, oxazolyl, thiazolyl, imidazolyl, pyrrolyl, pyrrolidinyl, piperidinyl, azepanyl, benzofuranyl, benzothienyl, indolyl, purinyl, quinolyl and isoquinolyl or heterocyclyl as defined above mono or disubstituted by lower alkyl, lower alkoxy or halogen and wherein aryl is unsubstituted phenyl or phenyl substituted with halogen, lower-alkyl, lower-alkoxy, lower-alkylenedioxy, carboxy, or trifluoromethyl; and $R^{11}$ is hydrogen or a residue $R^{10}$;

Z is —O—, —S— or —CH$_2$—;

X is —O—, —S— or —NH—;

n is 0 or 1; and m is 1, 2 or 3, or a pharmaceutically usable salt thereof; and an inert carrier.

\* \* \* \* \*

UNITED STATES PATENT AND TRADEMARK OFFICE
CERTIFICATE OF CORRECTION

PATENT NO. : 5,541,186
DATED : July 30, 1996
INVENTOR(S) : Breu, et al.

It is certified that error appears in the above-indentified patent and that said Letters Patent is hereby corrected as shown below:

Claim 1, Column 51, lines 43 and 44: "$(R^c,R^d)N-C(O)(CH_2)_{0-4})$ or"

should read --- $(R^c,R^d)N-C(O)(CH_2)_{0-4}O-$ or --- .

Claim 10, Column 53, line 53: "pyridin-2-ylcarbaminc acid" should read

-- pyridin-2-ylcarbamic acid --- .

Signed and Sealed this

Twenty-second Day of October, 1996

*Attest:*

BRUCE LEHMAN

*Attesting Officer*    *Commissioner of Patents and Trademarks*